US006187552B1

(12) United States Patent
Roberds et al.

(10) Patent No.: US 6,187,552 B1
(45) Date of Patent: Feb. 13, 2001

(54) METHOD FOR IDENTIFYING INHIBITORS OF JAK2/CYTOKINE RECEPTOR BINDING

(75) Inventors: Steven L. Roberds, Mattawan, MI (US); Paul S. Kaytes, Lewiston, NY (US)

(73) Assignee: Pharmacia & Upjohn Company, Kalamazoo, MI (US)

( * ) Notice: Under 35 U.S.C. 154(b), the term of this patent shall be extended for 0 days.

(21) Appl. No.: 09/046,158

(22) Filed: Mar. 23, 1998

Related U.S. Application Data

(60) Provisional application No. 60/041,511, filed on Mar. 24, 1997.

(51) Int. Cl.[7] .................................................. G01N 33/53
(52) U.S. Cl. .......................... 435/7.93; 435/7.9; 435/7.92
(58) Field of Search ............................. 436/501; 530/350, 530/351; 435/7.93, 7.92, 7.9

(56) References Cited

U.S. PATENT DOCUMENTS 5,691,147 * 11/1997 Draetta et al. ........................ 435/7.1

FOREIGN PATENT DOCUMENTS

| 655786 | 1/1995 | (AU) | ............................. C12N/15/54 |
| WO 95/03701 | 2/1995 | (WO) | ............................. A01N/43/04 |

OTHER PUBLICATIONS

Zhao et al., The Amino–terminal Portion of the JAK2 Protein Kinase is Necessary for Binding and Phosphorylation of the Granulocyte–Macrophage Colony–stimulating Factor Receptor Bc Chain. J. Biol. Chem. vol. 270, No. 23, pp. 13814–13818, Jun. 9. 1995.*
Altschul SF, Gish W, Miller W, Myers EW, Lipman DJ. "Basic Local Alignment Search Tool." *J Mol Biol* 1990; 215, 403–410.*
Barany G., Merrifield RB. "Solid–Phase Peptide Synthesis." *The Peptides* 1979; 2:1–284.*
Bates ME, Bertics PJ, Busse WW. "IL–5 activates a 45–kilodalton mitogen–activated protein (MAP) kinase and JAK–2 tyrosine kinase in hyman eosinophils." *J Immunol* 1996; 156:711–8.*
Bousquet J, Chanez P, Lacoste JY, Barneon G, Ghavanian N, Enander I, et al. "Eosinophilic inflammation in asthma." *N Engl J Med* 1990; 323:1033–9.*
Brizzi MF, Zini MG, Aronica MG, Blechman JM, Yarden Y, Pegoraro L. "Convergence of signaling by interleukin–3, granulocyte–macrophage colony–stimulating factor, and mast cell growth factor on JAK2 tyrosine kinase." *J Biol Chem* 1994; 269:31680–4.*
Caldenhoven E, van Dijk T, Raaijmakers JAM, Lammers J–WJ, Koenderman L, de Groot RP. "Activation of the STAT3/Acute Phase Response Factor Transcription Factor by Interleukin–5*," *J. Biol. Chem.* 1995;270: 25778–25784.*

Collins PD, Marleau S, Griffiths–Johnson DA, Jose PJ, Williams TJ. "Cooperation between interleukin–5 and the chemokine eotaxin to induce eosinophl accumulation in vivo." *J Exp Med* 1995; 182:1169–74.*
Devos R, Plaetinck G, Cornelis S, Guisez Y, Van der Heyden J, Tavernier J. "Interleukin–5 and its receptor: a drug target for eosinophilia associated with chronic allergic disease." *J Leukoc Biol* 1995; 57:813–9.*
Duhé RJ, Farrar WL. "Characterization of active and inactive forms of the JAK2 protein–tyrosine kinase produced via the baculovirus expression vector system." *J Biol Chem* 1995; 270:23084–9.*
Duhé RJ, Rui H, Greenwood JD, Garvey K & Farrar WL. "Cloning of the gene encoding rat JAK2, a protein tyrosine kinase." *Gene* 158:281–285 (1995).*
Frank SJ, Yi W, Zhao Y, Goldsmith JF, Gilliland G, Jiang J, et al. "Regions of the JAK2 tyrosine kinase required for coupling to the growth hormone receptor." *J Biol Chem* 1995; 270:14776–85.*
Griffiths–Johnson DA, Collins PD, Rossi AG, Jose PJ, Williams TJ. "The chemokine, eotaxin, activates guinea–pig eosinophils in vitro and causes their accumulation into the lung in vivo." *Biochem Biophys Res Comm* 1993; 197(3):1167–72.*
Harpur AG, Andres A–C, Ziemiecki A, Aston RR, Wilks AF. "JAK2, a third member of the JAK family of protein tyrosine kinases." *Oncogene* 1992; 7:1347–53.*
Hayashida K, Kitamura T, Gorman DM, Arai K–I, Yokota T, Miyajima A. "Molecular cloning of a second subunit of the receptor for human granulocyte–macrophage colony–stimulating factor (GM–CSF): reconstitution of a high–affinity GM–CSF receptor." *Proc Natl Acad Sci USA* 1990; 87:9655–9.*
Hoshi H, Ohno I, Honma M, Tanno Y, Yamauchi K, Tamura G, et al. "IL–5, IL–8 and GM–CSF immunostaining of sputum cells in bronchial asthma and chronic bronchitis." *Clin Exp Allergy* 1995; 25:720–8.*
Howarth P. "The airway inflammatory response in allergic asthma and its relationship to clinical disease." *Allergy* 1995; 50 (suppl. 22):13–21.*

(List continued on next page.)

*Primary Examiner*—Elizabeth Kemmerer
*Assistant Examiner*—Eileen B. O'Hara
(74) *Attorney, Agent, or Firm*—James D. Darnley, Jr.; Edward F. Rehberg

(57) ABSTRACT

The invention provides a method of identifying a therapeutic useful for treating or preventing asthma, which method includes the steps of contacting a identify compounds that inhibit the binding of human JAK2 protein to the $\beta_c$ first molecule comprising at least the N terminal 294 residues of JAK2 protein as shown in SEQ ID NO: 5 with a second molecule comprising at least 13 membrane proximal cytoplasmic amino acid residues of the $\beta_c$ subunit of the IL-3, IL-5, and GM-CSF receptors as shown in SEQ ID NO: 3 in the presence of a candidate compound to subunit of the IL-3, IL-5 and GM-CSF receptors. Compounds that block the signalling pathways of the IL-3, IL-5 and GM-CSF receptors may be of use in the treatment of asthma.

22 Claims, 45 Drawing Sheets

OTHER PUBLICATIONS

Ihle JN. "Cytokine receptor signalling." *Nature* 1995; 377:591–4.*

Ihle JN, Witthuhn BA, Quelle FW, Yamamoto K, Thierfelder WE, Kreider B, et al. "Signaling by the cytokine receptyor superfamily: JAKs and STATs." *Trends Biochem Sci* 1994; 19:222–7.*

Ihle JN. "STATs: Signal Transducers and Activators of Transcription." *Cell* 1996; 84:331–334.*

Kitamura T, Tange T, Terasawa T, Chiba S, Kuwaki T, Miyagawa K, et al. "Establishment and characterization of a unique human cell line that proliferates dependently on GM–CSF, IL–3, or erythropoietin." *J Cell Phys* 1989; 140:323–34.*

Kummer U, Thiel E. Doxiadis I, Eulitz M. Sladoljev S, Thierfelder S. "Tritium Radiolabeling of Antibodies to High Specific Activity with N–Succinimidyl[2,3–$^3$H] Propionate: Use in Detecting Monoclonal Antibodies." *J Immunol Methods* 1981; 367–374.*

Kung TT, Stelts DM, Zurcher JA, Adams GK, III, Egan RW, Kreutner W, et al. "Involvement of IL–5 in a murine model of allergic pulmonary inflammation: prophylactic and therapeutic effect of an anti–IL–5 antibody." *Am J Respir Cell Mol Biol* 1995: 13:360–5.*

Laemmli UK. "Cleavage of structural proteins during the assembly of the head of bacteriophage T4." *Nature* 1970; 227:680–5.*

Mauser PJ, Pitman A, Witt A, Fernandez X, Zurcher J, Kung T, et al. "Inhibitory effect of the TRFK–5 anti–IL–5 antibody in a guinea pig model of asthma." *Am Rev Respir Dis* 1993; 148:1623–7.*

Mauser PJ, Pitman AM, Fernandez X, Foran SK, Adams GK, III, Kreutner W, et al. "Effects of an antibody to interleukin–5 in a monkey model of asthma." *Am J Respir Crit Care Med* 1995; 152:467–72.*

Miyajima A, Mui AL–F, Ogorochi T, Sakamaki K. "Receptors for granulocyte–macrophage colony–stimulating factor, interleukin–3, and interleukin–5." *Blood* 1993; 82:1960–74.*

Monahan J, Siegel N, Keith R, Caparon M, Christine L, Compton R, Cusik S, Hirsch J, Huynh M, Devine C, Polazzi J, Rangwala S, Tsai B, and Portanova J. "Attenuation of IL–5–Mediated signal transduction, eosinophil survival, and inflammatory mediator release by a soluble human IL–5 receptor." *J. of Immunology* 1997; 159:4024–34.*

Möröy T, Grzeschiczek A, Petzold S, Hartmann K–U. "Expression of a Pim–1 transgene accelerates lymphoproliferation and inhibits apoptosis in lpr/lpr mice." *Proc Natl Acad Sci USA* 1993; 90:10734–8.*

Mui Al–F, Wakao H, Harada N, O'Farrell A–M, Miyajima A. "Interleukin–3, granulocyte–macrophage colony–stimulating factor, and interleukin–5 transduce signals through two forms of STAT5." *J Leukoc Biol* 1995; 57:799–803.*

National Heart, Lung, and Blood Institute. Guidelines for the diagnosis and management of asthma. National Asthma Education Program Expert Panel Report. *Pediatric Asthma, Allergy, and Immunology* 1991; 5:57.*

O'Reilly DR, Miller LK, Luckow VA. "Baculovirus Expression Vectors: A Laboratory Manual." New York: W.H. Freeman and Company, 1992.*

Ohlendieck K, Ervasti JM, Snook JB, Campbell KP. "Dystrophin–glycoprotein complex is highly enriched in isolated skeletal muscle sarcolemma." *J Cell Biol* 1991; 112:135–48.*

Pazdrak K, Stafford S, Alam R. "The activation of the JAK–STAT1 signaling pathway by IL–5 in eosinophils." *J Immunol* 1995; 155:397–402.*

Peeters P, Raynard SD, Cools J, Wlodarska I, et al. "Fusion of TEL, the ETS–Variant Gene 6 (ETV6), to the Receptor–Associated Kinase JAK2 as a Result of t(9;12) in a Lymphoid and t(9; 15; 12) in a Myeoid Leukemia." *Blood* 1997; 90:2535–2540.*

Quelle FW, Sato N, Witthuhn BA, Inhorn RC, Eder M, Miyajima A, et al. "JAK2 associates with the bc chain of the receptor for granulocyte–macrophage colony–stimulating factor, and its activation requires the membrane–proximal region." *Mol Cell Biol* 1994; 14:4335–41.*

Robinson DS, Ying S, Bentley Am, Meng Q, North J, Durham SR, et al. "Relationships among numbers of bronchoalveolar lavage cells expressing messenger ribonucleic acid for cytokines, asthma symptoms, and airway methacholine responsiveness in atopic asthma." *J Allergy Clin Immunol* 1993; 92:397–403.*

Sakamaki K, Miyajima I, Kitamura T, Miyajima A. "Critical cytoplasmic domains of the common b subunit of the human GM–CSF, IL–3 and IL–5 receptors for growth signal transduction and tyrosine phosphorylation." *EMBO J* 1992; 11:3541–9.*

Sakamaki K, Yonehara S. "Serum alleviates the requirement of the granulocyte–macrophage colony–stimulating factor (GM–CSF)–induced RAS activation for proliferation of BaF3 cells." *FEBS Lett* 1994; 353:133–7.*

Sakamoto KM, Mignacca RC, Gasson JC. "Signal transduction by granulocyte–macrophage colony–stimulating factor and interleukin–3 receptors." *Receptors Channels* 1994; 2:175–81.*

Sato N, Sakamaki K, Terada N, Arai K, Miyajima A. "Signal transduction by the high–affinity GM–CSF receptor: two distinct cytoplasmic regions of the common b subunit responsible for different signaling." *EMBO J* 1993; 12:4181–9.*

Sehmi R, Wardlaw AJ, Cromwell O, Kurihara K, Waltmann P, Kay AB. "Interleukin–5 selectively enhances the chemotactic response of eosinophils obtained from normal but not eosinophilic subjects." *Blood* 1992; 79:2952–9.*

Seminario M–C, Gleich GJ. "The role of eosinophils in the pathogenesis of asthma." *Curr Opinion Immunol* 1994; 6:860–4.*

Silvennoinen O, Witthuhn BA, Quelle FW, Cleveland JL, Yi T, Ihle JN. "Structure of the murine JAK2 protein–tyrosine kinase and its role in interleukin 3 signal transduction." *Proc Natl Acad Sci USA* 1993; 90:8429–33.*

Tanner JW, Chen W, Young RL, Longmore GD, Shaw AS. "The conserved Box 1 motif of cytokine receptors is required for Association with JAK Kinases*." *J. Biol. Chem.* 1995; 270:6523–6530.*

Teixeria MM, Williams TJ, Hellewell PG. "Mechanisms and pharmacological manipulation of eosinophil accumulation in vivo." *Trends Pharmacol Sci* 1995; 16:418–23.*

Tomioka K, MacGlashan DW, Jr., Lichtenstein LM, Bochner BS, Schleimer RP. "GM–CSF regulates human eosinophil responses to F–Met peptide and platelet activating factor." *J Immunol* 1993; 151:4989–97.*

Towbin H, Staehelin T, Bordon J. "Electrophoretic transfer of proteins from polyacrylamide gels to nitrocellulose sheets: procedure and some applications." *Proc Natl Acad Sci* 1979; 76:4350–4.*

Vinella D, D'Ari R. "Thermoinducible filamentation in *Escherichia coli* due to an altered RNA polymerase beta subunit is suppressed by high levels of ppGpp." *J Bacteriol* 1994; 176:966–72.*

Wallaert B, Desreumaux P, Copin MC, Tillie I, Benard A, Colombel JF, et al. "Immunoreactivity for interleukin 3 and 5 and granulocyte/macrophage colony–stimulating factor of intestinal mucosa in bronchial asthma." *J Exp Med* 1995; 182:1897–904.*

Yamaguchi Y, Hayashi Y, Sugama Y, Miura Y, Kasahara T, Kitamura S, et al. "Highly purified murine interleukin 5 (IL–5) stimulates eosinophil function and prolongs in vitro survival." *J Exp Med* 1988; 167:1737–42.*

Yamaguchi Y, Suda T, Ohta S, Tominaga K, Miura Y, Kasahara T. "Analysis of the survival of mature human eosinophils: interleukin–5 prevents apoptosis in mature human eosinophils." *Blood* 1991; 78:2542–7.*

Zhao Y, Wagner F, Frank SJ, Kraft AS. "The amino–terminal portion of the JAK2 protein kinase is necessary for binding and phosphorylation of the granulocyte–macrophage colony–stimulating factor receptor bc chain". *J Biol Chem* 1995; 270:13814–8.*

Zhuang H, Patel SV, He T–C, Sonsteby SK, Niu Z, Wojchowski DM. "Inhibition of erythropoietin–induced mitogenesis by a kinase–deficient form of JAK2." *J Biol Chem* 1994; 269:21411–4.*

Zhuang H, Niu Z, He T–C, Patel SV, Wojchowski DM. "Erythropoietin–dependent inhibition of apoptosis is supported by carboxyl–truncated receptor forms and blocked by dominant–negative forms of JAK2." *J Biol Chem* 1995; 270:14500–4.*

* cited by examiner

FIGURE 5 B

```
TACCTGGGGCCGCCCCACAGCCGCTCCCTACCTGACATCCTGGGCCAG
                                                        432
 Y   L   G   P   P   H   S   R   S   L   P   D   I   L   G   Q

CCGGAGCCCCCACAGGAGGGTGGGAGCCAGAAGTCCCCACCTCCAGGG
                                                        480
 P   E   P   P   Q   E   G   G   S   Q   K   S   P   P   P   G

TCCCTGGAGTACCTGTGTCTGCCTGCTGGGGGGCAGGTGCAACTGGTC
                                                        528
 S   L   E   Y   L   C   L   P   A   G   G   Q   V   Q   L   V

CCTCTGGCCCAGGCGATGGGACCGGGACAGGCCGTGGAAGTGGAGAGA
                                                        576
              Ras/MAPK activation domain
 P   L   A   Q   A   M   G   P   G   Q   A   V   E   V   E   R AGGCCGAGCCAGGGGGCTGCAGGGAGTCCCTCCCTGGAGTCCGGGGGA
                                                        624
              Ras/MAPK activation domain
 R   P   S   Q   G   A   A   G   S   P   S   L   E   S   G   G GGCCCTGCCCCTCCTGCTCTTGGGCCAAGGGTGGGAGGACAGGACCAA
                                                        672
              Ras/MAPK activation domain
 G   P   A   P   P   A   L   G   P   R   V   G   G   Q   D   Q
                          Sac I AAGGACAGCCCTGTGGCTATACCCATGAGCTCTGGGGACACTGAGGAC
                                                        720
              Ras/MAPK activation domain
 K   D   S   P   V   A   I   P   M   S   S   G   D   T   E   D CCTGGAGTGGCCTCTGGTTATGTCTCCTCTGCAGACCTGGTATTCACC
                                                        768
              Ras/MAPK activation domain
 P   G   V   A   S   G   Y   V   S   S   A   D   L   V   F   T
```

FIGURE 5 C

```
CCAAACTCAGGGGCCTCGTCTGTCTCCCTAGTTCCCTCTCTGGGCCTC
─────────────────────────────────────────────── 816
              Ras/MAPK activation domain
 P  N  S  G  A  S  S  V  S  L  V  P  S  L  G  L CCCTCAGACCAGACCCCCAGCTTATGTCCTGGGCTGGCCAGTGGACCC
─────────────────────────────────────────────── 864
              Ras/MAPK activation domain
 P  S  D  Q  T  P  S  L  C  P  G  L  A  S  G  P CCTGGAGCCCCAGGCCCTGTGAAGTCAGGGTTTGAGGGCTATGTGGAG
─────────────────────────────────────────────── 912
              Ras/MAPK activation domain
 P  G  A  P  G  P  V  K  S  G  F  E  G  Y  V  E Sac I CTCCCTCCAATTGAGGGCCGGTCCCCCAGGTCACCAAGGAACAATCCT
─────────────────────────────────────────────── 960
              Ras/MAPK activation domain
 L  P  P  I  E  G  R  S  P  R  S  P  R  N  N  P GTCCCCCCTGAGGCCAAAAGCCCTGTCCTGAACCCAGGGGAACGCCCG
─────────────────────────────────────────────── 1008
              Ras/MAPK activation domain
 V  P  P  E  A  K  S  P  V  L  N  P  G  E  R  P GCAGATGTGTCCCCAACATCCCCACAGCCCGAGGGCCTCCTTGTCCTG
─────────────────────────────────────────────── 1056
              Ras/MAPK activation domain
 A  D  V  S  P  T  S  P  Q  P  E  G  L  L  V  L CAGCAAGTGGGCGACTATTGCTTCCTCCCCGGCCTGGGGCCCGGCCCT
─────────────────────────────────────────────── 1104
 Ras/MA
 Q  Q  V  G  D  Y  C  F  L  P  G  L  G  P  G  P
```

FIGURE 5 D

Sma I

```
CTCTCGCTCCGGAGTAAACCTTCTTCCCCGGGACCCGGTCCTGAGATC
                                                   1152
 L   S   L   R   S   K   P   S   S   P   G   P   G   P   E   I

AAGAACCTAGACCAGGCTTTTCAAGTCAAGAAGCCCCCAGGCCAGGCT
                                                   1200
 K   N   L   D   Q   A   F   Q   V   K   K   P   P   G   Q   A

GTGCCCCAGGTGCCCGTCATTCAGCTCTTCAAAGCCCTGAAGCAGCAG
                                                   1248
 V   P   Q   V   P   V   I   Q   L   F   K   A   L   K   Q   Q

GACTACCTGTCTCTGCCCCCTTGGGAGGTCAACAAGCCTGGGGAGGTG
                                                   1296
 D   Y   L   S   L   P   P   W   E   V   N   K   P   G   E   V

TGTTGA
         1302
 C   .
```

FIGURE 9

```
ATGGGAATGG CCTGCCTTAC AATGACAGAA ATGGAGGGAA CATCCACCTC    50
TTCTATATAT CAGAATGGTG ATATTTCTGG AAATGCCAAT TCTATGAAGC   100
AAATAGATCC AGTTCTTCAG GTGTATCTTT ACCATTCCCT TGGGAAATCT   150
GAGGCAGATT ATCTGACCTT TCCATCTGGG GAGTATGTTG CAGAAGAAAT   200
CTGTATTGCT GCTTCTAAAG CTTGTGGTAT CACACCTGTG TATCATAATA   250
TGTTTGCTTT AATGAGTGAA ACAGAAAGGA TCTGGTATCC ACCCAACCAT   300
GTCTTCCATA TAGATGAGTC AACCAGGCAT AATGTACTCT ACAGAATAAG   350
ATTTTACTTT CCTCGTTGGT ATTGCAGTGG CAGCAACAGA GCCTATCGGC   400
ATGGAATATC TCGAGGTGCT GAAGCTCCTC TTCTTGATGA CTTTGTCATG   450
TCTTACCTCT TTGCTCAGTG GCGGCATGAT TTTGTGCACG GATGGATAAA   500
AGTACCTGTG ACTCATGAAA CACAGGAAGA ATGTCTTGGG ATGGCAGTGT   550
TAGATATGAT GAGAATAGCC AAAGAAAACG ATCAAACCCC ACTGGCCATC   600
TATAACTCTA TCAGCTACAA GACATTCTTA CCAAAATGTA TTCGAGCAAA   650
GATCCAAGAC TATCATATTT TGACAAGGAA GCGAATAAGG TACAGATTTC   700
GCAGATTTAT TCAGCAATTC AGCCAATGCA AAGCCACTGC CAGAAACTTG   750
AAACTTAAGT ATCTTATAAA TCTGGAAACT CTGCAGTCTG CCTTCTACAC   800
AGAGAAATTT GAAGTAAAAG AACCTGGAGG TGGTCCTTCA GGTGAGGAGA   850
TTTTTGCAAC CATTATAATA ACTGGAAACG GT                      882
```

FIGURE 10

```
MGMACLTMTE MEGTSTSSIY QNGDISGNAN SMKQIDPVLQ VYLYHSLGKS    50

EADYLTFPSG EYVAEEICIA ASKACGITPV YHNMFALMSE TERIWYPPNH   100

VFHIDESTRH NVLYRIRFYF PRWYCSGSNR AYRHGISRGA EAPLLDDFVM   150

SYLFAQWRHD FVHGWIKVPV THETQEECLG MAVLDMMRIA KENDQTPLAI   200

YNSISYKTFL PKCIRAKIQD YHILTRKRIR YRFRRFIQQF SQCKATARNL   250

KLKYLINLET LQSAFYTEKF EVKEPGGGPS GEEIFATIII TGNG         294
```

FIGURE 11

```
     RKWEEKIPNP SKSHLFQNGS AELWPPGSMS AFTSGSPPHQ GPWGSRFPEL    50
5
     EGVFPVGFGD SE                                             62
```

A  Use of $^3$H Full Length JAK2 with Peptides

Conditions
0 - beads only
1-6 - peptides 1-6
7 - peptide 4 using 5-fold excess JAK2

B  Use of 3H NJAK2 with Peptides

Conditions
0 - beads only
1-6 - peptides 1-6
7 - peptide 4 using 10-fold excess JAK2

Titration with Different Amounts of Peptide 4 and Three Different Concentrations of Labeled JAK2

A  Test of Effect of Several Detergents in SPA

Conditions
0, 2, 4, 6, 8 - beads only
0 & 1 - no detergent
2 & 3 - 0.01 % Triton X-100
4 & 5 - 0.003 % Tween 20
6 & 7 - 0.0025 % Brij 35
8 & 9 - 0.01 % digitonin B  Effect of Brij 35 and Dithiothreitol on SPA Conditions
0, 2, 4 - beads only
0 & 1 - no detergent or DTT
2 & 3 - 0.0025 % Brij 35 plus 0.1 mM DTT
4 & 5 - 0.0025 % Brij 35 plus 1.0 mM DTT

A  Competition with Peptide 4/Streptavidin

Conditions
- 0 - beads only
- 1 - peptide 4 bound to beads only
- 2 - plus soluble peptide 4/streptavidin at 1:1
- 3 - plus soluble peptide 4/streptavidin at 4:1
- 4 - plus 20 uM peptide 4
- 5 - plus 20 uM streptavidin B  Competition with Peptide 1/Streptavidin and Peptide 4/Streptavidin Conditions
0 - beads only
1 - peptide 4 bound to beads only
2 - plus peptide 1/streptavidin at 4:1
3 - plus peptide 4/streptavidin at 4:1

FIGURE 22 A

```
CCCGGGGGAA TGGCCTGCCT TACGATGACA GAAATGGAGG GAACATCCAC CTCTTCTATA    60
TATCAGAATG GTGATATTTC TGGAAATGCC AATTCTATGA AGCAAATAGA TCCAGTTCTT   120
CAGGTGTATC TTTACCATTC CCTTGGGAAA TCTGAGGCAG ATTATCTGAC CTTTCCATCT   180
GGGGAGTATG TTGCAGAAGA AATCTGTATT GCTGCTTCTA AAGCTTGTGG TATCACACCT   240
GTGTATCATA ATATGTTTGC TTTAATGAGT GAAACAGAAA GGATCTGGTA TCCACCCAAC   300
CATGTCTTCC ATATAGATGA GTCAACCAGG CATAATGTAC TCTACAGAAT AAGATTTTAC   360
TTTCCTCGTT GGTATTGCAG TGGCAGCAAC AGAGCCTATC GGCATGGAAT ATCTCGAGGT   420
GCTGAAGCTC CTCTTCTTGA TGACTTTGTC ATGTCTTACC TCTTTGCTCA GTGGCGGCAT   480
GATTTTGTGC ATGGATGGAT AAAAGTACCT GTGACTCATG AAACACAGGA AGAATGTCTT   540
GGGATGGCAG TGTTAGATAT GATGAGAATA GCCAAAGAAA ACGATCAAAC CCCACTGGCC   600
ATCTATAACT CTATCAGCTA CAAGACATTC TTACCAAAAT GTATTCGAGC AAAGATCCAA   660
GACTATCATA TTTTGACAAG GAAGCGAATA AGGTACAGAT TTCGCAGATT TATTCAGCAA   720
TTCAGCCAAT GCAAAGCCAC TGCCAGAAAC TTGAAACTTA AGTATCTTAT AAATCTGGAA   780
ACTCTGCAGT CTGCCTTCTA CACAGAGAAA TTTGAAGTAA AGAACCTGG  AAGTGGTCCT   840
TCAGGTGAGG AGATTTTTGC AACCATTATA ATAACTGGAA ACGGTGGAAT TCAGTGGTCA   900
AGAGGGAAAC ATAAAGAAAG TGAGACACTG ACAGAACAGG ATTTACAGTT ATATTGCGAT   960
TTTCCTAATA TTATTGATGT CAGTATTAAG CAAGCAAACC AAGAGGGTTC AAATGAAAGC  1020
CGAGTTGTAA CTATCCATAA GCAAGATGGT AAAAATCTGG AAATTGAACT TAGCTCATTA  1080
AGGGAAGCTT TGTCTTTCGT GTCATTAATT GATGGATATT ATAGATTAAC TGCAGATGCA  1140
CATCATTACC TCTGTAAAGA AGTAGCACCT CCAGCCGTGC TTGAAAATAT ACAAAGCAAC  1200
TGTCATGGCC CAATTTCGAT GGATTTTGCC ATTAGTAAAC TGAAGAAAGC AGGTAATCAG  1260
```

FIGURE 22 B

```
ACTGGACTGT ATGTACTTCG ATGCAGTCCT AAGGACTTTA ATAAATATTT TTTGACTTTT    1320

GCTGTCGAGC GAGAAAATGT CATTGAATAT AAACACTGTT TGATTACAAA AAATGAGAAT    1380

GAAGAGTACA ACCTCAGTGG GACAAAGAAG AACTTCAGCA GTCTTAAAGA TCTTTTGAAT    1440

TGTTACCAGA TGGAAACTGT TCGCTCAGAC AATATAATTT CCAGTTTAC TAAATGCTGT     1500

CCCCCAAAGC CAAAAGATAA ATCAAACCTT CTAGTCTTCA GAACGAATGG TGTTTCTGAT    1560

GTACCAACCT CACCAACATT ACAGAGGCCT ACTCATATGA ACCAAATGGT GTTTCACAAA    1620

ATCAGAAATG AAGATTTGAT ATTTAATGAA AGCCTTGGCC AAGGCACTTT ACAAAGATT    1680

TTTAAAGGCG TACGAAGAGA AGTAGGAGAC TACGGTCAAC TGCATGAAAC AGAAGTTCTT    1740

TTAAAAGTTC TGGATAAAGC ACACAGAAAC TATTCAGAGT CTTTCTTTGA AGCAGCAAGT    1800

ATGATGAGCA AGCTTTCTCA CAAGCATTTG GTTTTAAATT ATGGAGTATG TGTCTGTGGA    1860

GACGAGAATA TTCTGGTTCA GGAGTTTGTA AAATTTGGAT CACTAGATAC ATATCTGAAA    1920

AAGAATAAAA ATTGTATAAA TATATTATGG AAACTTGAAG TTGCTAAACA GTTGGCATGG    1980

GCCATGCATT TTCTAGAAGA AAACACCCTT ATTCATGGGA ATGTATGTGC CAAAAATATT    2040

CTGCTTATCA GAGAAGAAGA CAGGAAGACA GGAAATCCTC CTTTCATCAA ACTTAGTGAT    2100

CCTGGCATTA GTATTACAGT TTTGCCAAAG GACATTCTTC AGGAGAGAAT ACCATGGGTA    2160

CCACCTGAAT GCATTGAAAA TCCTAAAAAT TTAAATTTGG CAACAGACAA ATGGAGTTTT    2220

GGTACCACTT TGTGGGAAAT CTGCAGTGGA GGAGATAAAC CTCTAAGTGC TCTGGATTCT    2280

CAAAGAAAGC TACAATTTTA TGAAGATAGG CATCAGCTTC CTGCACCAAA GTGGGCAGAA    2340

TTAGCAAACC TTATAAATAA TTGTATGGAT TATGAACCAG ATTTCAGGCC TTCTTTCAGA    2400

GCCATCATAC GAGATCTTAA CAGTTTGTTT ACTCCAGATT ATGAACTATT AACAGAAAAT    2460

GACATGTTAC CAAATATGAG GATAGGTGCC CTAGGGTTTT CTGGTGCCTT TGAAGACCGG    2520
```

FIGURE 22 C

```
GATCCTACAC AGTTTGAAGA GAGACATTTG AAATTTCTAC AGCAACTTGG CAAGGGTAAT    2580

TTTGGGAGTG TGGAGATGTG CCGGTATGAC CCTCTACAGG ACAACACTGG GGAGGTGGTC    2640

GCTGTAAAAA AGCTTCAGCA TAGTACTGAA GAGCACCTAA GAGACTTTGA AAGGGAAATT    2700

GAAATCCTGA AATCCCTACA GCATGACAAC ATTGTAAAGT ACAAGGGAGT GTGCTACAGT    2760

GCTGGTCGGC GTAATCTAAA ATTAATTATG GAATATTTAC CATATGGAAG TTTACGAGAC    2820

TATCTTCAAA AACATAAAGA ACGGATAGAT CACATAAAAC TTCTGCAGTA CACATCTCAG    2880

ATATGCAAGG GTATGGAGTA TCTTGGTACA AAAAGGTATA TCCACAGGGA TCTGGCAACG    2940

AGAAATATAT TGGTGGAGAA CGAGAACAGA GTTAAAATTG GAGATTTTGG GTTAACCAAA    3000

GTCTTGCCAC AAGACAAAGA ATACTATAAA GTAAAGAAC CTGGTGAAAG TCCCATATTC    3060

TGGTATGCTC CAGAATCACT GACAGAGAGC AAGTTTTCTG TGGCCTCAGA TGTTTGGAGC    3120

TTTGGAGTGG TTCTGTATGA ACTTTTCACA TACATTGAGA AGAGTAAAAG TCCACCAGCG    3180

GAATTATGC GTATGATTGG CAATGACAAA CAAGGACAGA TGATCGTGTT CCATTTGATA    3240

GAACTTTTGA AGAATAATGG AAGATTACCA AGACCAGATG GATGCCCAGA TGAGATCTAT    3300

ATGATCATGA CAGAATGCTG GAACAATAAT GTAAATCAAC GCCCCTCCTT TAGGGATCTA    3360

GCTCTTCGAG TGGATCAAAT AAGGGATAAC ATGGCTGGAG ATTATAAAGA TGATGATGAT    3420

AAAAATTAGC CCGGG                                                   3435
```

FIGURE 23 A

```
    Met Ala Cys Leu Thr Met Thr Glu Met Glu Gly Thr Ser Thr Ser Ser
    1               5                   10                  15

Ile Tyr Gln Asn Gly Asp Ile Ser Gly Asn Ala Asn Ser Met Lys Gln
                20                  25                  30

Ile Asp Pro Val Leu Gln Val Tyr Leu Tyr His Ser Leu Gly Lys Ser
                35                  40                  45

Glu Ala Asp Tyr Leu Thr Phe Pro Ser Gly Glu Tyr Val Ala Glu Glu
                50                  55                  60

Ile Cys Ile Ala Ala Ser Lys Ala Cys Gly Ile Thr Pro Val Tyr His
    65              70                  75                      80

Asn Met Phe Ala Leu Met Ser Glu Thr Glu Arg Ile Trp Tyr Pro Pro
                    85                  90                  95

Asn His Val Phe His Ile Asp Glu Ser Thr Arg His Asn Val Leu Tyr
                    100                 105                 110

Arg Ile Arg Phe Tyr Phe Pro Arg Trp Tyr Cys Ser Gly Ser Asn Arg
                    115                 120                 125

Ala Tyr Arg His Gly Ile Ser Arg Gly Ala Glu Ala Pro Leu Leu Asp
                    130                 135                 140

Asp Phe Val Met Ser Tyr Leu Phe Ala Gln Trp Arg His Asp Phe Val
    145                 150                 155                 160

His Gly Trp Ile Lys Val Pro Val Thr His Glu Thr Gln Glu Glu Cys
                    165                 170                 175

Leu Gly Met Ala Val Leu Asp Met Met Arg Ile Ala Lys Glu Asn Asp
                    180                 185                 190

Gln Thr Pro Leu Ala Ile Tyr Asn Ser Ile Ser Tyr Lys Thr Phe Leu
                    195                 200                 205

Pro Lys Cys Ile Arg Ala Lys Ile Gln Asp Tyr His Ile Leu Thr Arg
                    210                 215                 220
```

FIGURE 23 B

Lys Arg Ile Arg Tyr Arg Phe Arg Arg Phe Ile Gln Gln Phe Ser Gln
225             230             235             240

Cys Lys Ala Thr Ala Arg Asn Leu Lys Leu Lys Tyr Leu Ile Asn Leu
            245             250             255

Glu Thr Leu Gln Ser Ala Phe Tyr Thr Glu Lys Phe Glu Val Lys Glu
            260             265             270

Pro Gly Ser Gly Pro Ser Gly Glu Glu Ile Phe Ala Thr Ile Ile Ile
            275             280             285

Thr Gly Asn Gly Gly Ile Gln Trp Ser Arg Gly Lys His Lys Glu Ser
            290             295             300

Glu Thr Leu Thr Glu Gln Asp Leu Gln Leu Tyr Cys Asp Phe Pro Asn
305             310             315             320

Ile Ile Asp Val Ser Ile Lys Gln Ala Asn Gln Glu Gly Ser Asn Glu
            325             330             335

Ser Arg Val Val Thr Ile His Lys Gln Asp Gly Lys Asn Leu Glu Ile
            340             345             350

Glu Leu Ser Ser Leu Arg Glu Ala Leu Ser Phe Val Ser Leu Ile Asp
            355             360             365

Gly Tyr Tyr Arg Leu Thr Ala Asp Ala His His Tyr Leu Cys Lys Glu
            370             375             380

Val Ala Pro Pro Ala Val Leu Glu Asn Ile Gln Ser Asn Cys His Gly
385             390             395             400

Pro Ile Ser Met Asp Phe Ala Ile Ser Lys Leu Lys Lys Ala Gly Asn
            405             410             415

Gln Thr Gly Leu Tyr Val Leu Arg Cys Ser Pro Lys Asp Phe Asn Lys
            420             425             430

FIGURE 23 C

```
Tyr Phe Leu Thr Phe Ala Val Glu Arg Glu Asn Val Ile Glu Tyr Lys
        435             440             445

His Cys Leu Ile Thr Lys Asn Glu Asn Glu Glu Tyr Asn Leu Ser Gly
        450             455             460

Thr Lys Lys Asn Phe Ser Ser Leu Lys Asp Leu Leu Asn Cys Tyr Gln
465             470             475             480

Met Glu Thr Val Arg Ser Asp Asn Ile Ile Phe Gln Phe Thr Lys Cys
            485             490             495

Cys Pro Pro Lys Pro Lys Asp Lys Ser Asn Leu Leu Val Phe Arg Thr
            500             505             510

Asn Gly Val Ser Asp Val Pro Thr Ser Pro Thr Leu Gln Arg Pro Thr
        515             520             525

His Met Asn Gln Met Val Phe His Lys Ile Arg Asn Glu Asp Leu Ile
        530             535             540

Phe Asn Glu Ser Leu Gly Gln Gly Thr Phe Thr Lys Ile Phe Lys Gly
545             550             555             560

Val Arg Arg Glu Val Gly Asp Tyr Gly Gln Leu His Glu Thr Glu Val
            565             570             575

Leu Leu Lys Val Leu Asp Lys Ala His Arg Asn Tyr Ser Glu Ser Phe
        580             585             590

Phe Glu Ala Ala Ser Met Met Ser Lys Leu Ser His Lys His Leu Val
        595             600             605

Leu Asn Tyr Gly Val Cys Val Cys Gly Asp Glu Asn Ile Leu Val Gln
        610             615             620

Glu Phe Val Lys Phe Gly Ser Leu Asp Thr Tyr Leu Lys Lys Asn Lys
625             630             635             640

Asn Cys Ile Asn Ile Leu Trp Lys Leu Glu Val Ala Lys Gln Leu Ala
            645             650             655
```

FIGURE 23 D

Trp Ala Met His Phe Leu Glu Glu Asn Thr Leu Ile His Gly Asn Val
            660             665                 670

Cys Ala Lys Asn Ile Leu Leu Ile Arg Glu Glu Asp Arg Lys Thr Gly
        675             680                 685

Asn Pro Pro Phe Ile Lys Leu Ser Asp Pro Gly Ile Ser Ile Thr Val
        690             695                 700

Leu Pro Lys Asp Ile Leu Gln Glu Arg Ile Pro Trp Val Pro Pro Glu
705             710                 715                 720

Cys Ile Glu Asn Pro Lys Asn Leu Asn Leu Ala Thr Asp Lys Trp Ser
                725             730                 735

Phe Gly Thr Thr Leu Trp Glu Ile Cys Ser Gly Gly Asp Lys Pro Leu
            740             745                 750

Ser Ala Leu Asp Ser Gln Arg Lys Leu Gln Phe Tyr Glu Asp Arg His
        755             760                 765

Gln Leu Pro Ala Pro Lys Trp Ala Glu Leu Ala Asn Leu Ile Asn Asn
        770             775                 780

Cys Met Asp Tyr Glu Pro Asp Phe Arg Pro Ser Phe Arg Ala Ile Ile
785             790                 795                 800

Arg Asp Leu Asn Ser Leu Phe Thr Pro Asp Tyr Glu Leu Leu Thr Glu
                805             810                 815

Asn Asp Met Leu Pro Asn Met Arg Ile Gly Ala Leu Gly Phe Ser Gly
            820             825                 830

Ala Phe Glu Asp Arg Asp Pro Thr Gln Phe Glu Glu Arg His Leu Lys
        835             840                 845

Phe Leu Gln Gln Leu Gly Lys Gly Asn Phe Gly Ser Val Glu Met Cys
        850             855                 860

Arg Tyr Asp Pro Leu Gln Asp Asn Thr Gly Glu Val Val Ala Val Lys
865             870                 875                 880

FIGURE 23 E

```
Lys Leu Gln His Ser Thr Glu Glu His Leu Arg Asp Phe Glu Arg Glu
            885             890             895

Ile Glu Ile Leu Lys Ser Leu Gln His Asp Asn Ile Val Lys Tyr Lys
            900             905             910

Gly Val Cys Tyr Ser Ala Gly Arg Arg Asn Leu Lys Leu Ile Met Glu
            915             920             925

Tyr Leu Pro Tyr Gly Ser Leu Arg Asp Tyr Leu Gln Lys His Lys Glu
            930             935             940

Arg Ile Asp His Ile Lys Leu Leu Gln Tyr Thr Ser Gln Ile Cys Lys
945             950             955             960

Gly Met Glu Tyr Leu Gly Thr Lys Arg Tyr Ile His Arg Asp Leu Ala
            965             970             975

Thr Arg Asn Ile Leu Val Glu Asn Glu Asn Arg Val Lys Ile Gly Asp
            980             985             990

Phe Gly Leu Thr Lys Val Leu Pro Gln Asp Lys Glu Tyr Tyr Lys Val
            995             1000            1005

Lys Glu Pro Gly Glu Ser Pro Ile Phe Trp Tyr Ala Pro Glu Ser Leu
            1010            1015            1020

Thr Glu Ser Lys Phe Ser Val Ala Ser Asp Val Trp Ser Phe Gly Val
            1025            1030            1035            1040

Val Leu Tyr Glu Leu Phe Thr Tyr Ile Glu Lys Ser Lys Ser Pro Pro
            1045            1050            1055

Ala Glu Phe Met Arg Met Ile Gly Asn Asp Lys Gln Gly Gln Met Ile
            1060            1065            1070

Val Phe His Leu Ile Glu Leu Leu Lys Asn Asn Gly Arg Leu Pro Arg
            1075            1080            1085

Pro Asp Gly Cys Pro Asp Glu Ile Tyr Met Ile Met Thr Glu Cys Trp
            1090            1095            1100
```

FIGURE 23 F

```
     Asn Asn Asn Val Asn Gln Arg Pro Ser Phe Arg Asp Leu Ala Leu Arg
5    1105            1110            1115                    1120

Val Asp Gln Ile Arg Asp Asn Met Ala Gly Asp Tyr Lys Asp Asp Asp
                     1125            1130                1135

10   Asp Lys Asn
```

METHOD FOR IDENTIFYING INHIBITORS OF JAK2/CYTOKINE RECEPTOR BINDING

This application claims the benefit of U.S. Provisional application Ser. No. 60/041511, filed Mar. 24, 1997.

FIELD OF THE INVENTION

The present invention relates to an in vitro method for identifying compounds that inhibit the binding of human JAK2 protein to cytokine receptors.

BACKGROUND OF THE INVENTION

Asthma is characterized by reversible airway obstruction, airway inflammation, and increased airway responsiveness to various stimuli. [1] Increases in the numbers and activation state of eosinophils and mast cells in asthmatic bronchial epithelium are well documented. [2] Additionally, the activation state of airway T lymphocytes is increased. [2] Inhaled β2-adrenergic receptor agonists control acute airway hyperresponsiveness in some individuals but do not affect the underlying chronic inflammation. When used chronically, glucocorticoids decrease eosinophil accumulation in the lung and reduce symptoms in most, but not all, patients with asthma. However, glucocorticoids inhibit the activation of all inflammatory cells, which results in potential side effects due to immunosuppression. [3]

In patients with asthma, but not in normal individuals, degranulated eosinophils are found below the basement membrane among lung epithelial cells. [4] Also in asthmatics, the number of eosinophils in bronchoalveolar lavage fluid and peripheral blood are elevated, and these levels are correlated with the severity of the disease. [4] When activated, eosinophils release cytotoxic mediators including eosinophil cationic protein, major basic protein, eosinophil peroxidase, and eosinophil-derived neurotoxin. [5] The resulting damage to lung epithelium leads to chronic inflammation and the symptoms of asthma.

The number of cells expressing IL-3, IL-4, IL-5, and GM-CSF mRNA is increased in asthmatic airways. [6] As a result, levels of IL-3, IL-5, and GM-CSF protein are increased in abundance in asthmatic airways. [7,8]The functions of these three cytokines overlap in many ways. IL-3 and GM-CSF are important in the development and maturation of eosinophils in the bone marrow. [9] IL-5 and GM-CSF induce release of eosinophils from the bone marrow and prolong the survival of eosinophils in vitro by preventing apoptosis. [10,11] GM-CSF and IL-5 prime eosinophils to respond more strongly to activators such as platelet activating factor and formyl-Met-Leu-Phe [12,13] and eotaxin [14], which was discovered in the airway of animal models of lung inflammation. [15] Antibodies against IL-5 have been tested for anti-inflammatory effects in animal models of acute lung inflammation. In guinea pigs, anti-IL-5 antibody completely inhibited eosinophil influx into the lungs following antigen challenge [16], but the antibody only partially decreased eosinophilia in similar experiments using mice and monkeys. [17,18] The effect of anti-IL-5 antibodies or IL-5 receptor antagonists [19] in chronic asthma in humans is unknown.

IL-3, IL-5, and GM-CSF receptors are heterodimers consisting of an α subunit unique to each cytokine receptor and a common β subunit ($β_c$) [20] Both subunits are required for high-affinity ligand binding. [20] The α subunit of these receptors is almost entirely extracellular, leaving the membrane-spanning $β_c$ subunit responsible for transducing cytoplasmic signals following cytokine binding. Activation of $β_c$ signaling by IL-3, IL-5, or GM-CSF leads to autophosphorylation of the tyrosine kinase JAK2 and activation of the mitogen-activated protein (MAP) kinase pathway. [21–25]

The $β_c$ subunit does not contain a consensus protein kinase domain [26]; however, $β_c$ binds directly to JAK2 [21,27], suggesting that this is the most proximal kinase involved in signaling. Binding of IL-3, IL-5, or GM-CSF to their receptor complexes likely leads to aggregation of the receptors and activation of JAK2. [28] This is a reasonable hypothesis given that overexpression of JAK2 using baculovirus vectors in insect cells leads to autophosphorylation of JAK2 once the amount of protein accumulates to a critical level. [29]

After JAK2 is activated by autophosphorylation, it phosphorylates the $β_c$ subunit of the receptor. This leads to recruitment of signal transducers and activators of transcription (STATs) via binding of their SH2 domains to tyrosine phosphates on the receptor complex (FIG. 1). The STATs are in turn phosphorylated, probably by JAK2, form dimers with other phosphorylated STATs, and are translocated to the nucleus where they bind directly to DNA. [30,31] Using this mechanism, IL-3, IL-5, and GM-CSF can activate STAT1, STAT3, and two forms of STAT5. [21,32,33]

Truncation and deletion mutagenesis has shown that separate regions of the $β_c$ cytoplasmic domain are responsible for activating the JAK2 and MAP kinase pathways. [24,27,34] For example, 62 membrane-proximal cytoplasmic amino acids [SEQ ID NO:3] are necessary and sufficient for activating JAK2 and upregulating transcription of c-myc and pim-1. [24] Pim-1 is a serine/threonine kinase that has anti-apoptotic activity. [35] The more C-terminal region of $β_c$ including amino acids 626–763 is necessary for activation of the MAP kinase pathway and increased transcription of c-fos and c-jun. [24] Only the 62 membrane-proximal residues of $β_c$ as shown in [SEQ ID NO:3] are required for cell survival and proliferation when other growth factors activate the MAP kinase pathway. [36] This membrane proximal region contains two motifs known as Box 1 and Box 2, which are loosely conserved among many cytokine receptors. Box 1 may be necessary for JAK binding, as deletion of Box 1 or mutation of specific prolines in the motif can decrease JAK binding. [37]

JAK2 is also activated by other cytokine receptors, including those for IL-6 and IL-10 [28], as well as erythropoietin and growth hormone. [38,39] The N-terminal region of JAK2 is necessary for binding to the growth hormone receptor [39] and probably other receptors, as well. JAK2 deletion mutagenesis demonstrated that the N-terminal 239 amino acids are required for binding $β_c$ and that the N-terminal 294 residues are sufficient to bind $β_c$. [40] Deletion of the N-terminus does not affect the kinase activity of JAK2 expressed in insect cells. [29] The tyrosine kinase domain of JAK2 is present near the C-terminus of the protein [41], and this domain must be functional to support IL-3- and erythropoietin-induced proliferation and survival. [38,42]

In view of the continuing need for the identification of potential therapeutics for the treatment of asthma, a binding assay which identifies compounds that effect the binding of $β_c$ with JAK2 would be a valuable tool.

SUMMARY OF THE INVENTION

A method of screening for compounds potentially useful for treating or preventing asthma, the method comprising contacting a first molecule comprising at least the N-terminal 294 residues of JAK2 protein as shown in [SEQ ID NO:5] with a second molecule comprising at least 62 membrane-proximal cytoplasmic amino acids of $\beta_c$ subunit of the IL-3, IL-5 and GM-CSF receptors as shown in [SEQ ID NO:3] in the presence of a candidate compound. Following this contacting step, a detection step is conducted to determine whether a complex forms between the first and second molecules to determine whether the candidate compound inhibits the formation of the complex, the inhibition being an indication that the candidate compound is potentially useful for treating asthma.

A second method of screening for compounds potentially useful for treating or preventing asthma, the method comprising contacting a first molecule comprising at least the N-terminal 294 residues of JAK2 protein as shown in [SEQ ID NO:5] with a second molecule comprising at least 13 cytoplasmic amino acids of $\beta_c$ subunit of the IL-3, IL-5 and GM-CSF receptors as shown in [SEQ ID NOS:13–19] in the presence of a candidate compound. Following this contacting step, a detection step is conducted to determine whether a complex forms between the first and second molecules to determine whether the candidate compound inhibits the formation of the complex, the inhibition being an indication that the candidate compound is potentially useful for treating asthma.

In preferred embodiments, either the first or the second molecule may be labeled to facilitate the identification of candidate compounds. Examples of labeling techniques which can be used in the present invention include fluorescent labeling or radioisotope labeling

DESCRIPTION OF THE FIGURES

FIG. 9 illustrates the nucleotide sequence [SEQ ID NO:4] of the subcloned JAK2 fragment used in the present invention.

FIG. 10 illustrates the deduced amino acid sequence [SEQ ID NO:5] of JAK2 fragment used in the present invention.

FIG. 11 illustrates 62 membrane-proximal cytoplasmic amino acids [SEQ ID NO:3] of the $\beta_c$ that are necessary and sufficient for activating JAK2.

FIGS. 22 A and B and C illustrate the nucleotide sequence [SEQ ID NO:21] of the subcloned full-length JAK2 cDNA used in the present invention.

FIGS. 23 A–F illustrate the deduced amino acid sequence [SEQ ID NO:22] of the full-length JAK2 protein used in the present invention.

DETAILED DESCRIPTION OF THE INVENTION

Figure 1:
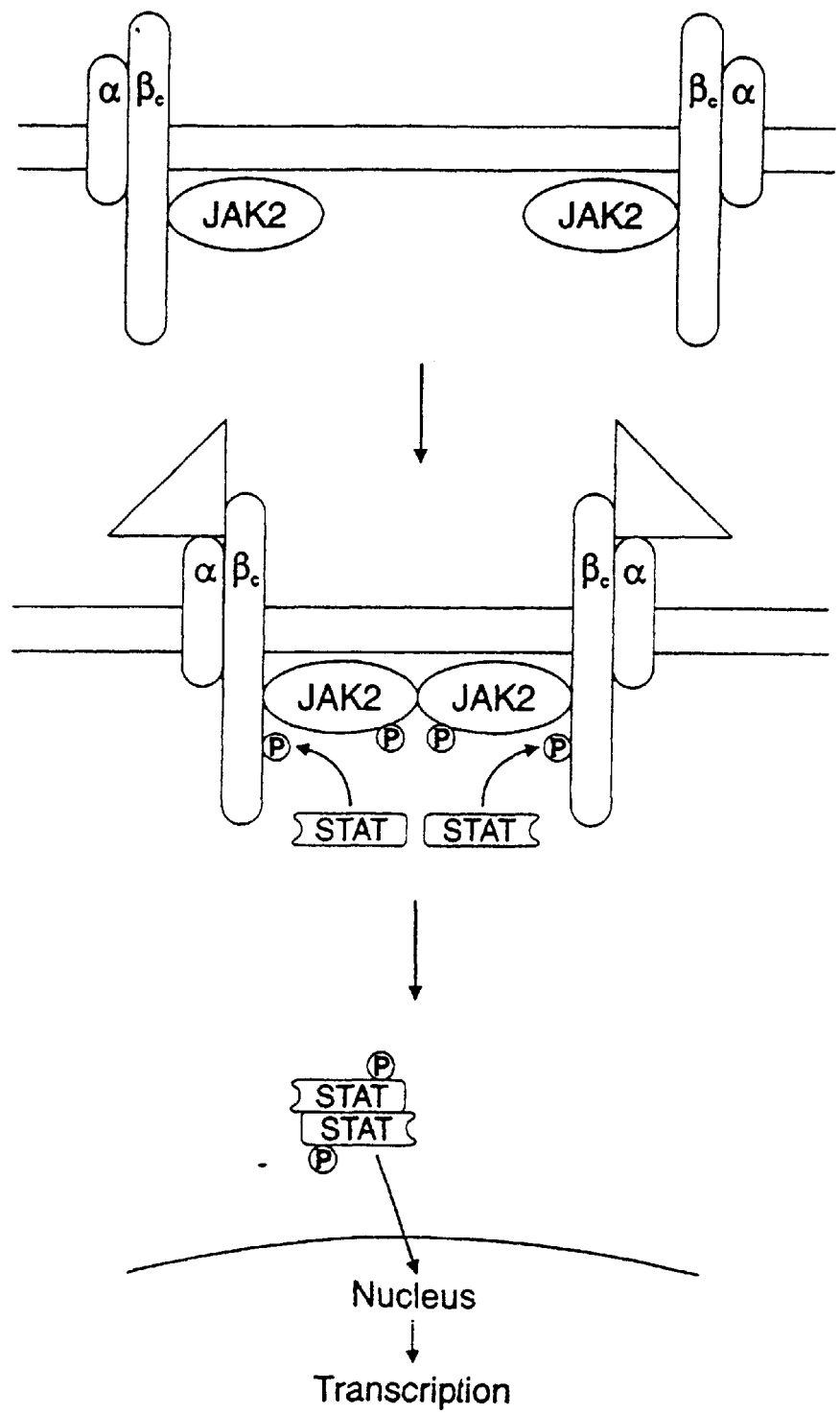
FIG. 1 illustrates a model of $\beta_c$/JAK/STAT signal transduction through IL-3, IL-5, and GM-CSF receptors. Specifically, following binding of cytokine (triangle) to its receptor, the receptors are thought to cluster, bringing $\beta_c$-bound JAK2 molecules into close proximity and allowing them to phosphorylate one another. The $\beta_c$ subunit is then phosphorylated, leading to recruitment of STATs to the receptor complex. Phosphorylated STATs form dimers which are translocated to the nucleus where they bind directly to DNA to affect transcription of specific genes.

Eosinophils appear to play a key role in the pathogenesis of asthma and the JAK2 signaling pathway appears to be critical to the activity of the eosinophil-activating cytokines IL-3, IL-5, and GM-CSF. As noted above, there are many points in the pathway that could be targeted to decrease the ability of these cytokines to recruit and activate eosinophils, which would be useful in the treatment of asthma. At the receptor level, antagonists could be developed, but because all three cytokines are present in asthmatic airways, a single antagonist would allow the two remaining cytokines to continue activating eosinophils. Inhibitors of JAK2 kinase activity would inhibit the activity of all three cytokines, but because JAK2 is used by other receptors for signaling, such inhibitors could have untoward effects. Additional mediators (eg, STATs, pim-1) are activated further downstream which, like JAK2, are utilized by other signaling pathways, making them less desirable targets.

The common point in this pathway that is required only for IL-3, IL-5, and GM-CSF function, however, is the activation of JAK2 by $\beta_c$. Because JAK2 is thought to be activated by autophosphorylation following clustering of $\beta_c$ subunits to which it is bound, disruption of $\beta_c$/JAK2 binding should disrupt signaling by all three cytokines. Although IL-3, IL-5, and GM-CSF have effects on other cells, no cell type other than eosinophils is known to be dependent upon them for survival. Therefore, it is expected that such an approach would selectively lead to earlier apoptosis in eosinophils. JAK2 is activated by other receptors containing Box 1 and Box 2 motifs, but these motifs are sufficiently dissimilar among receptors that identification of binding inhibitors specific for $\beta_c$/JAK2 appears likely.

We view blocking the interaction between $\beta_c$ and JAK2 as a new molecular mechanism for the treatment of asthma. To assist us in demonstrating the value of this discovery, we first identified the biochemical endpoints demonstrating the activity of the $\beta_c$/JAK2 signaling pathway in eosinophils and in an IL-3, IL-5, or GM-CSF-dependent cell line. We then developed a binding assay to demonstrate that recombinant forms of $\beta_c$ and JAK2 can bind one another in vitro using, e.g., scintillation proximity assay (SPA), fluorescence polarization or ELISA. This information allows for the development of a high-volume screen to identify blocking compounds.

Confirmation of Activity of $\beta_c$/JAK2 Pathway

EXAMPLE 1

Isolation of Human Peripheral Blood Eosinophils

Eosinophils were isolated from human whole blood or granulocyte leukapheresis packs obtained from Pharmacia and Upjohn Clinical Research Unit—Kalamazoo, Mich. Only blood from donors who had >5% peripheral blood eosinophils was used, while leukapheresis donors usually had 3–5% eosinophils. One unit of whole blood was divided among 50-ml polypropylene centrifuge tubes and centrifuged for 20 minutes at 300×g at room temperature (RT). The plasma was removed and 50 ml were centrifuged at 2500×g for 15 minutes at RT to remove platelets. The resulting platelet poor plasma (ppp) was diluted 1:4 in normal saline.

The blood cell pellets from the first centrifugation were each suspended in 5 ml 6% Dextran T500 (Pharmacia Biotech, Uppsala, Sweden) in normal saline, and sufficient normal saline was added to make 50 ml. Tubes were mixed well, and red blood cells (rbc) were allowed to sediment for 60 minutes at RT. The white blood cells (wbc) were recovered and centrifuged at 300×g for 10 minutes at RT. When the starting material was a leukapheresis pack, it was not necessary to add the dextran because the starch in the leukapheresis medium caused rbcs to sediment in a similar fashion.

The cells were distributed to centrifuge tubes and immediately allowed to sediment for 60 minutes at RT. The recovered wbc were centrifuged and washed once in saline, centrifuging at 300×g for 5 minutes at RT to remove platelets. The wbc pellets from either blood or leukapheresis packs were resuspended in ppp (diluted 1:4 as described above), pooled and distributed to four 50 ml conical centrifuge tubes of 20 ml each. Each tube was underlayered with 12.5 ml LSM (Lymphocyte Separation Medium=Ficoll/Hypaque solution, density 1.0770–1.0800g/ml, Organon Teknika Corporation, Durham, N.C.) and centrifuged at 750×g for 25 minutes at RT. The mononuclear cells at the interface and all LSM down to the pellet were removed.

If the starting cells were from a leukapheresis pack, the LSM gradient step was repeated to avoid contamination from the much larger mononuclear cell interface. The pelleted granulocytes were resuspended in a total pooled volume of 5 ml phosphate buffered saline (PBS) and placed in an ice bath. Rbc were lysed by the addition of 20 ml ice cold water, followed in 30 seconds by the addition of 20 ml 2× PBS. The granulocytes were pelleted by centrifugation at 300×g for 5 minutes at RT, resuspended in 20 ml modified Hanks Balanced Salt Solution [Modified HBSS=10 ml 10× HBSS without calcium and magnesium, 1 ml 1 M HEPES pH 7.3, 0.47 ml 7.5% sodium bicarbonate, 1 ml 200 mM L-glutamine (all from GibcoBRL Life Technologies, Grand Island, N.Y.), 10 ml heat-inactivated fetal bovine serum (Irvine Scientific, Irvine, Calif.), 77.5 ml distilled water], washed once by centrifugation, resuspended in 20 ml modified HBSS and counted.

To remove neutrophils, the cell concentration was adjusted to $8 \times 10^7$ granulocytes/ml and 1:50 3G8 anti-CD16 antibody (hybridoma cell line a gift of Dr. David Segal, NCI, now available through ATCC, Rockville, Md.) was added. The cells were rocked with the antibody at 4° C. for 30 to 60 minutes, centrifuged and washed twice with modified HBSS. Cells were resuspended in modified HBSS, and washed magnetic beads coated with anti-mouse IgG (PerSeptive Biosystems, Framingham, Mass.) were added at a ratio of 10 beads/granulocyte and a final concentration of $8 \times 10^7$ granulocytes/ml. Cells and beads were rocked at 4° C. for 30 minutes. The neutrophil/bead complexes were removed with strong magnets (Advanced Magnetics, Cambridge, Mass.) in two 5-minute separations.

A cytospin slide was prepared, stained with Diff-Quik (Baxter Scientific Products, McGaw Park, Ill.), and a differential count was done. The resulting purified eosinophil preparation contained 90 to 95% eosinophils. Approximately 50–100 million eosinophils were obtained from a unit of blood or 100–400 million from a leukapheresis pack.

EXAMPLE 2

Cytokine Stimulation of Cells and Immunoblotting

Immediately after purification, eosinophils were resuspended at $2 \times 10^7$ cells/ml in RPMI 1640 medium (GibcoBRL, Gaithersburg, Md.) supplemented with 1% fetal bovine serum (FBS, GibcoBRL, Gaithersburg, Md.) and incubated 2 min at 37°. Recombinant human IL-5 (Biosource, Camarillo, Calif.) diluted in PBS with 0.1% bovine serum albumin was added at 12.5 ng/ml for various times using $1 \times 10^7$ cells per data point. Tubes were placed on ice and 10 volumes of PBS with 0.1 mM sodium orthovanadate were added to each tube. Eosinophils were pelleted by centrifugation at 300×g and resuspended in 0.6 ml lysis buffer (20 mM Tris-Cl, pH 7.4, 100 mM NaCl, 10 mM sodium pyrophosphate, 2 mM EDTA, 50 mM NaF, 1 mM sodium orthovanadate, 3% Triton X-100) with protease inhibitors (10 $\mu$g/ml aprotinin, 10 $\mu$g/ml leupeptin, and 0.2 mM phenylmethylsulfonyl fluoride).

After incubation on ice for 15 min, debris was pelleted by centrifugation at 16,000×g. $\beta_c$ was immunoprecipitated from the lysate by rotating overnight at 4° with a 1:300 dilution of anti-$\beta_c$ antibody (Upstate Biotechnology, Lake Placid, N.Y.). Twenty microliters of protein A-Sepharose (Pharmacia Biotech, Uppsala, Sweden) were added to each lysate, and the incubation was continued one hour.

The beads were washed three times by centrifugation with 1 ml cold lysis buffer, resuspended in sodium dodecyl sulfate-polyacrylamide gel electrophoresis (SDS-PAGE) loading buffer [44], boiled 10 min, and separated by electrophoresis on 4–20% acrylamide gradient gels (Integrated Separation Systems, Natick, Mass.). Proteins were transferred by the method of Towbin et al [45] to Optitran (Schleicher & Schuell, Keene, N.H.). After blocking in TBS-T (20 mM Tris, pH 7.4, 100 mM NaCl, and 0.05% Tween-20) with 1% bovine serum albumin at 37° for one hour, peroxidase-conjugated anti-phosphotyrosine antibody RC20 (Transduction Laboratories, Lexington, Ky.) was added at a dilution of 1:3000 and incubation continued for two hours at room temperature. The blot was washed three times for 10 min at room temperature in TBS-T and developed using SuperSignal HRP (Pierce Chemical, Rockford, Ill.).

The human erythroleukemia cell line TF-1 [46] was obtained from the American Type Culture Collection and grown in RPMI 1640 supplemented with 10% FBS, 100 U/ml penicillin (GibcoBRL, Gaithersburg, Md.), 100 $\mu$g/ml streptomycin (GibcoBRL, Gaithersburg, Md.), and 2.5 ng/ml recombinant human IL-3 (Biosource, Camarillo, Calif.). Before experiments, TF-1 cells were grown overnight in RPMI 1640 medium with 1% PBS in the absence of IL-3. Cells were then resuspended at $2 \times 10^7$ cells/ml in fresh RPMI 1640 with 1% FBS and treated as described for eosinophils above, except 20 ng/ml IL-3 was used and the lysis buffer was 20 mM Tris, pH 7.6, 50 mM NaCl, 50 mM NaF, 1 mM sodium orthovanadate, 5 mM EGTA, and 1% Triton X-100. For cells treated without IL-3, PBS+0.1% BSA was added instead.

JAK2 was immunoprecipitated from the lysate by rotating overnight at 4° with a 1:300 dilution of anti-JAK2 antibody (Upstate Biotechnology, Lake Placid, N.Y.). Twenty microliters of protein A-Sepharose (Pharmacia Biotech, Uppsala, Sweden) were added to each lysate, and the incubation was continued one hour.

The beads were washed three times by centrifugation with 1 ml cold lysis buffer, resuspended in sodium dodecyl sulfate-polyacrylamide gel electrophoresis (SDS-PAGE) loading buffer [44], boiled 10 min, and separated by electrophoresis on 4–20% acrylamide gradient gels (Integrated Separation Systems, Natick, Mass.). Proteins were transferred by the method of Towbin et al [45] to Optitran (Schleicher & Schuell, Keene, N.H.). After blocking in TBS-T (20 mM Tris, pH 7.4, 100 mM NaCl, and 0.05% Tween-20) with 1% bovine serum albumin at 37° for one hour, peroxidase-conjugated anti-phosphotyrosine antibody RC20 (Transduction Laboratories, Lexington, Ky.) was added at a dilution of 1:3000 and incubation continued for two hours at room temperature. The blot was washed three times for 10 min at room temperature in TBS-T and developed using SuperSignal HRP (Pierce Chemical, Rockford, Ill.).

EXAMPLE 3

The $\beta_c$/JAK2 Pathway is Active in Eosinophils and TF-1 Cells

Figure 2:
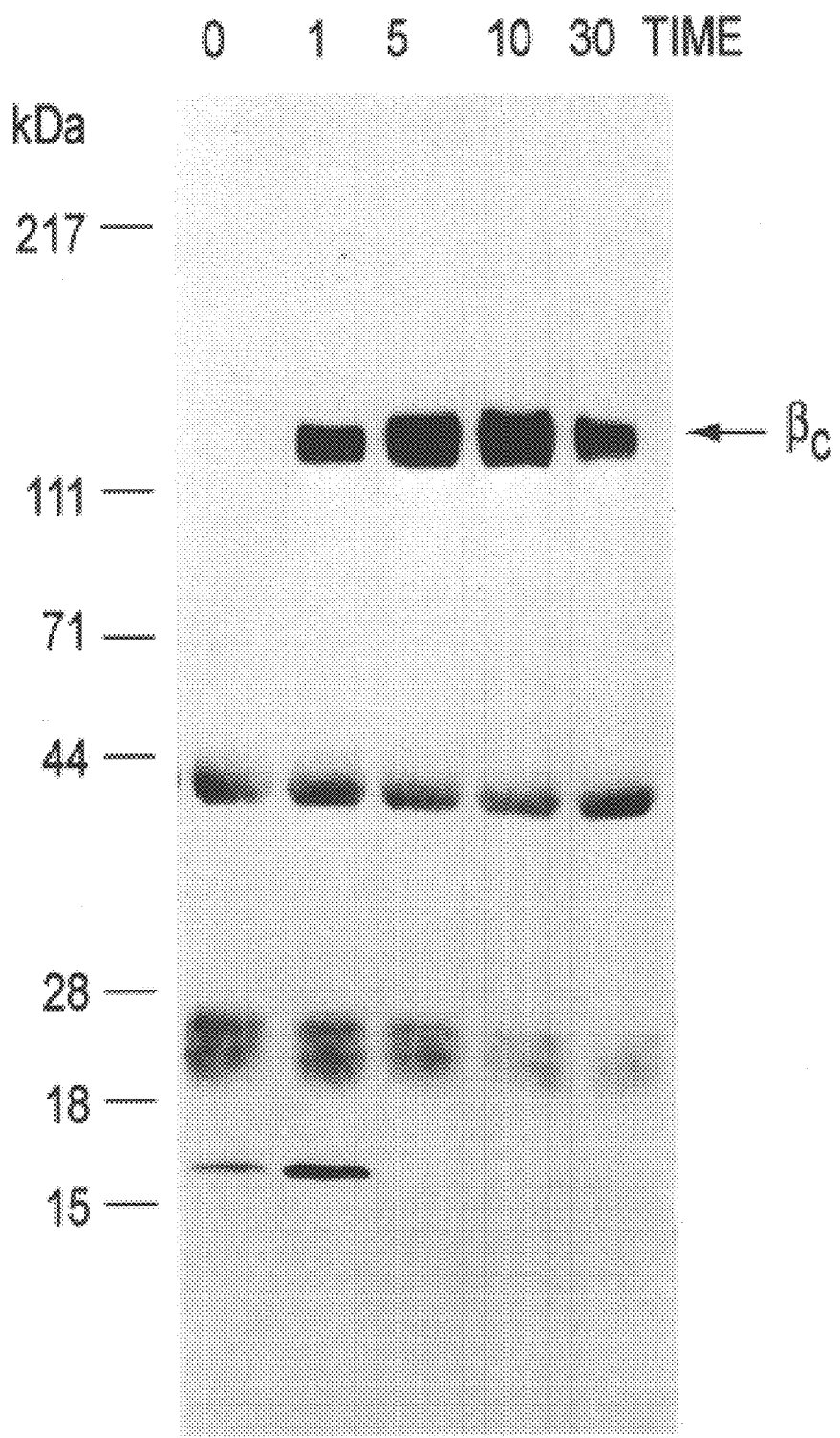
FIG. 2 illustrates the tyrosine phosphorylation of $\beta_c$ in human eosinophils after stimulation with IL-5. Shown is an anti-phosphotyrosine immunoblot of $\beta_c$ immunoprecipitated from human eosinophils stimulated with IL-5 for the time (in minutes) shown. Molecular weight standards ($M_r \times 10^{-3}$) are indicated. Bands below 44 kDa represent nonspecific binding of the anti-phosphotyrosine antibody to the heavy and light chains of the immunoprecipitating antibody.

As noted above, some of the resuspended purified eosinophils were exposed to human IL-5 for various times using $1 \times 10^7$ cells per data point. This stimulation of purified human eosinophils with 12.5 ng/ml human IL-5 at 37° C. resulted in tyrosine phosphorylation of $\beta_c$ within 1 min (FIG. 2). The level of tyrosine phosphorylation peaked at 5–10 min after stimulation, and dephosphorylation was evident by 30 min despite the continued presence of IL-5. Similar experiments have been attempted to look at JAK2 tyrosine phosphorylation in response to IL-5, but the relatively low level of JAK2 in eosinophils has hampered these efforts.

Figure 3:
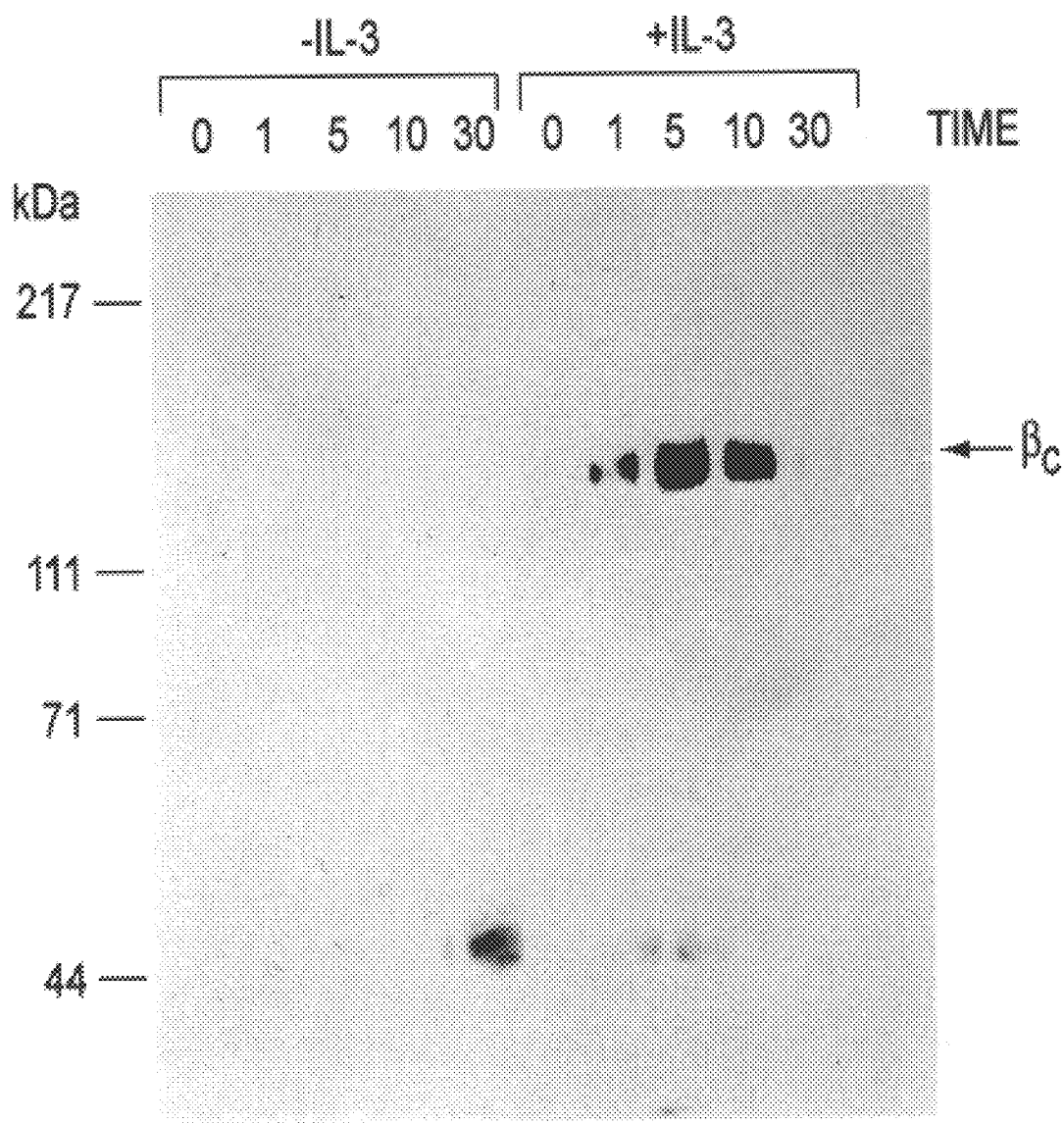
FIG. 3 illustrates the tyrosine phosphorylation of $\beta_c$ in human TF-1 cells. Shown is an anti-phosphotyrosine immunoblot of $\beta_c$ immunoprecipitated from human TF-1 cells stimulated with IL-3 (+IL-3) or vehicle (−IL-3) for the time (in minutes) shown. A 7.5% acrylamide gel was used. Molecular weight standards ($M_r \times 10^{-3}$) are indicated.
Figure 4:
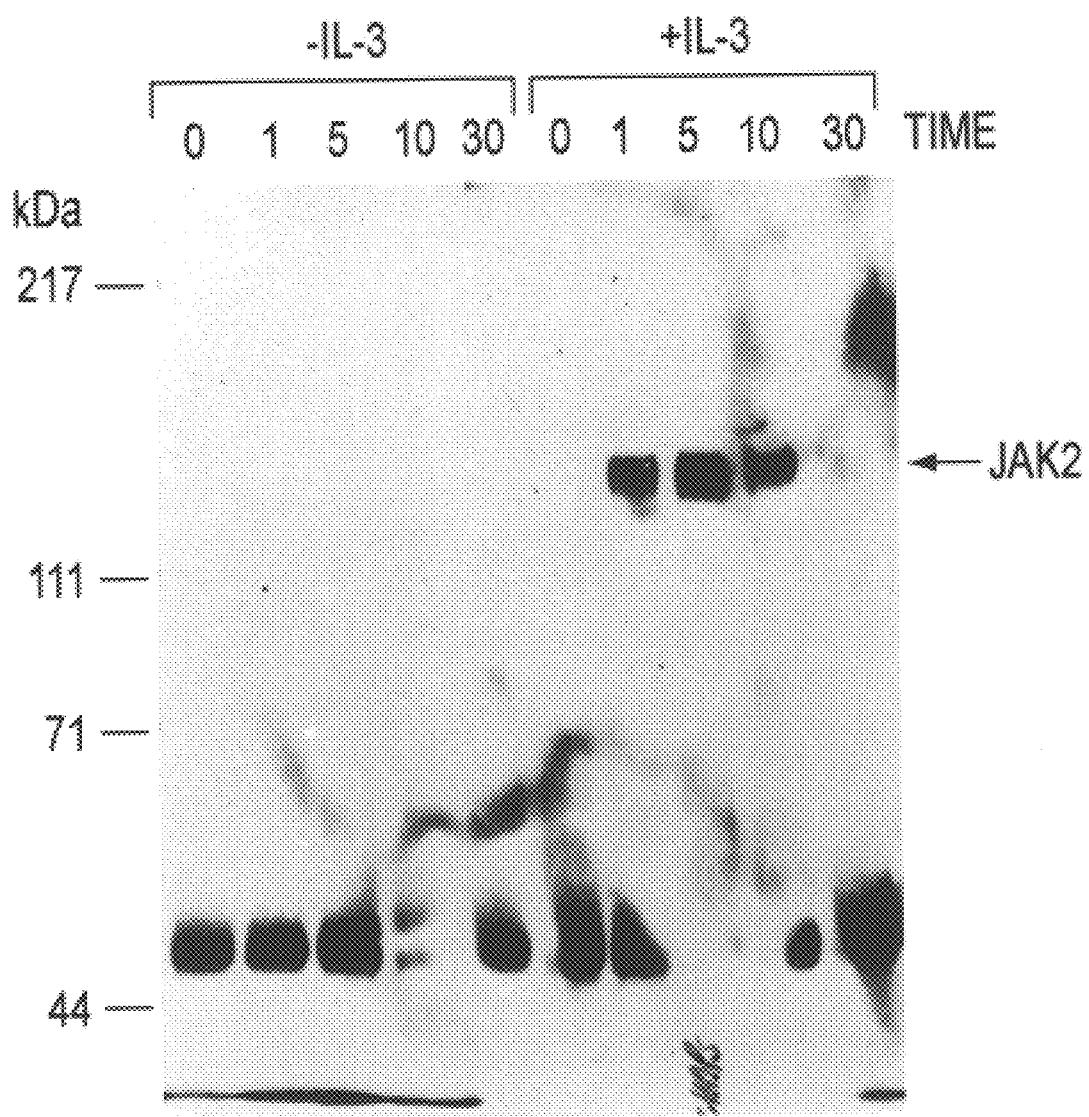
FIG. 4 illustrates tyrosine phosphorylation of JAK2 in human TF-1 cells. Shown is an anti-phosphotyrosine immunoblot of JAK2 immunoprecipitated from human TF-1 cells stimulated with IL-3 (+IL-3) or vehicle (−IL-3) for the time (in minutes) shown. A 7.5% acrylamide gel was used. Molecular weight standards ($M_r \times 10^{-3}$) are indicated.

Similar experiments have been performed in TF-1 cells, a human erythroleukemia cell line that is dependent upon IL-3, IL-5, or GM-CSF for proliferation. [46] Stimulation of TF-1 cells with 20 ng/ml IL-3 at 37° results in tyrosine phosphorylation of $\beta_c$ with a time course matching that seen in eosinophils (FIG. 3). Additionally, JAK2 tyrosine phosphorylation was easily detectable in TF-1 cells (FIG. 4), and its time course paralleled that of $\beta_c$. The response time is dose-dependent, as 200 ng/ml IL-3 results in peak phosphorylation of both proteins in 1 min. Addition to cells of PBS+0.1% BSA, the diluent used for IL-3, in the absence of IL-3 failed to induce tyrosine phosphorylation of $\beta_c$ or JAK2 (FIGS. 3 and 4).

These experiments confirm that the $\beta_c$/JAK2 signaling pathway is active in eosinophils and TF-1 cells. Because both are dependent upon IL-3, IL-5, or GM-CSF for survival, either cell type could theoretically be used in a screen to identify compounds that would block cytokine-stimulated survival and proliferation. Any screen based on inhibition of proliferation, however, would also identify cytotoxic compounds resulting in falsely identifying cytotoxic compounds as positives in the inhibition of cell proliferation. Therefore, to avoid these problems, we decided to develop a cell-free assay having a defined molecular endpoint. Such an assay required that fragments of human $\beta_c$ and JAK2 be cloned and expressed.

$\beta_c$/JAK2 Binding Assay

EXAMPLE 4

Generation of $\beta_c$ Protein and Construction of $\beta_c$-Containing Plasmids Human $\beta_c$ cDNA has been cloned by Hayashida et al from TF-1 cells. [26] To generate protein for use in a binding assay, cDNA encoding the entire cytoplasmic domain of human $\beta_c$ was subcloned into a pGEX vector, creating a glutathione-S-transferase (GST) fusion protein when expressed in *E. coli*.

Specifically, the human erythroleukemia cell line TF-1 [46] was obtained from the American Type Culture Collection, Rockwell, Md. (ATTC Accession No. CRL-2003) and grown in RPMI 1640 supplemented with 10% FBS, 100 U/ml penicillin, 100 µg/ml streptomycin (Gibco/BRL, Gaithersburg, Md.), and 2.5 ng/ml recombinant human IL-3 (Biosource International, Inc., Camarillo, Calif.).

RNA was prepared from the IL-3-dependent TF-1 cell line using Tri-Reagent according to the manufacturer's instructions (Molecular Research Center, Inc., Cincinnati, Ohio). Total RNA (2.5 µg/reaction) was used to synthesize cDNA using the Superscript Preamplification System for First Strand cDNA Synthesis (Gibco BRL, Gaithersburg, Md.). Separate reactions were performed using either oligo (dT) or random hexamers as primers, and then combined.

The cDNA encoding the cytoplasmic portion of $\beta_c$ was amplified from TF-1 cell cDNA using a sense primer corresponding to nucleotides 1421–1438 (5' TCGAATTCATC-TACGGGTACAGGCTG 3' [SEQ ID NO:6]) and an antisense primer complementary to nucleotides 2715–2732 (5' TAGCGGCCGCTCAACACACCTCCCCAGG 3' [SEQ ID NO:7]) of human $\beta_c$ [26]. The sense primer was designed to add an EcoRI restriction site to the 5' end of the amplified $\beta_c$ cDNA and the antisense primer was designed to add a NotI restriction site to the 3' end of the amplified $\beta_c$ cDNA. PCR was performed using Taq Extender (Stratagene, La Jolla, Calif.) according to the manufacturer's instructions and a cycle profile of 94° for five minutes followed by 35 cycles of 94° for 30 seconds, 60° for 30 seconds, and 72° for 3 minutes followed by a single incubation at 72° for 10 minutes.

The fragment was then cloned between the EcoRI and NotI sites of pGEX5X-1 (Pharmacia Biotech, Uppsala, Sweden), creating pGEX5X-$\beta_c$, an in-frame fusion of the cytoplasmic domain of $\beta_c$ with glutathione-S-transferase. The sequence was verified by fluorescent dye termination sequencing using an Applied Biosystems Sequencer Model No. ABI373A.

The transformed *E. coli* were diluted 1:100 from an overnight culture into either L Broth or Terrific Broth (Gibco BRL, Gaithersburg, Md.) supplemented with 100 µg/ml ampicillin, and grown at 30° C. to an $OD_{550}$ of approximately 0.5. IPTG was added to a final concentration of 1 mM, and the culture was further grown for 2–4 hours. Cells were collected by centrifugation and stored as frozen cell pellets until needed.

The cell pellets were dissolved in SDS loading buffer and subjected to SDS-PAGE after which all proteins were transferred to nitrocellulose (Optitran, Schleicher & Scheull, Keene, N.H.) using the method of Towbin et al [45] at approximately 0.2 ODU of cell lysate per lane. The nitrocellulose filters were incubated with anti-$\beta_c$-GST (UBI, Lake Placid, N.Y.) and peroxidase-coupled goat anti-rabbit IgG (Boehringer-Mannheim, Indianapolis, Ind.), and bands representing GST or GST/$\beta_c$ fusion proteins were visualized using hydrogen peroxide and 4-chloro-1-napthol as described. [48]

Unfortunately, expression of the cytoplasmic domain of human $\beta_c$ using a GST fusion protein resulted in the protein being badly degraded in total *E. coli* extracts. The degradation was not improved by changing *E. coli* strains, by changing growth temperature, or by using an alternative expression system utilizing a T7 promoter to drive expression of a thioredoxin-$\beta_c$ fusion protein (data not shown).

Because the membrane-proximal 62 amino acids of $\beta_c$ [SEQ ID NO:3] are necessary and sufficient for GM-CSF-induced activation of JAK2 and stimulation of proliferation

Figure 5:
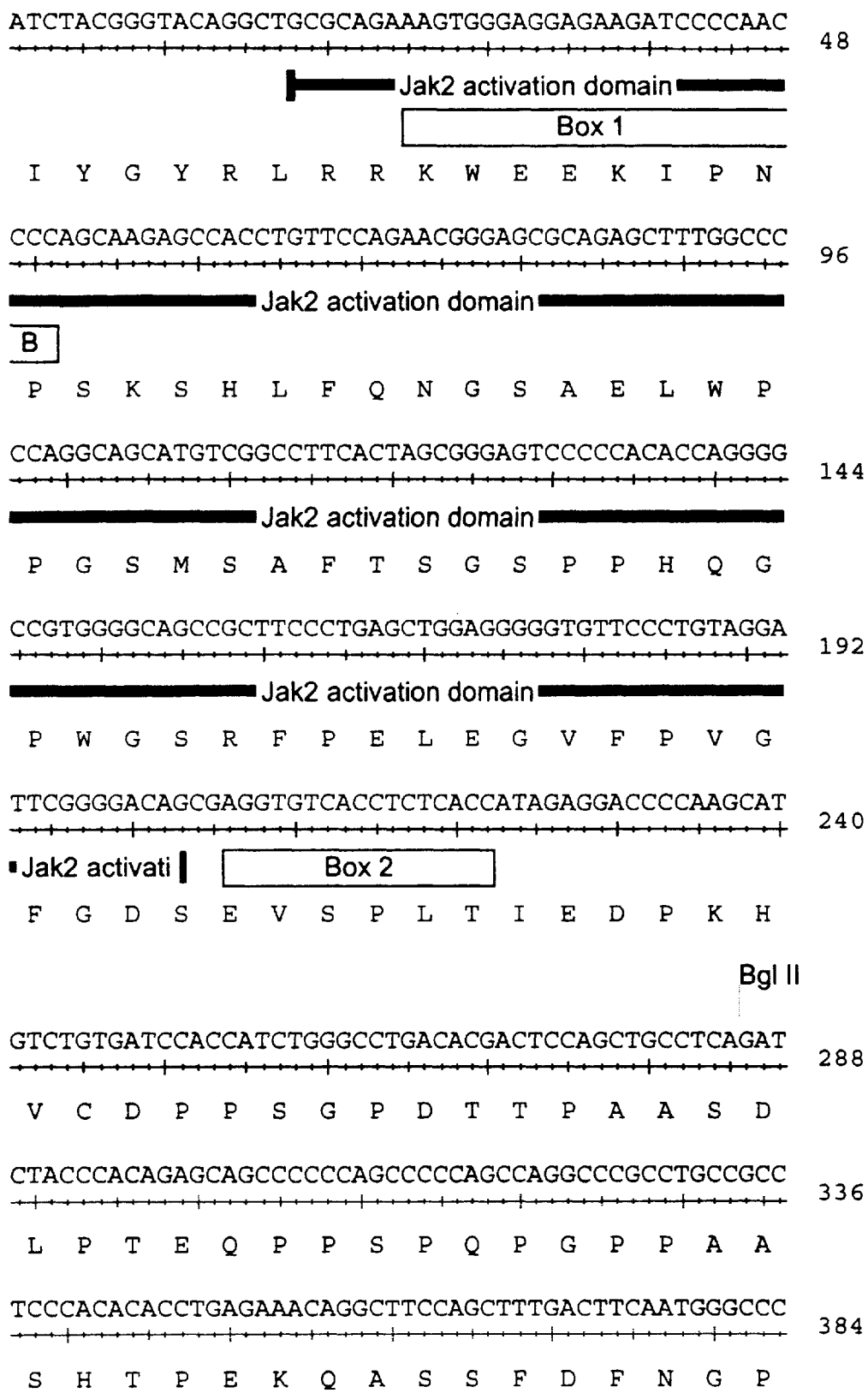
FIGS. 5 A, B, C and D illustrate the nucleotide [SEQ ID NO:1] and amino acid sequence [SEQ ID NO:2] of human $\beta_c$ cytoplasmic domain. Regions of the protein necessary for activation of JAK2 [SEQ ID NO:3] or activation of the Ras/MAP kinase pathway [24] and Box 1 and Box 2 domains are shown. BglII, SacI, and SmaI restriction sites used to generate truncated GST-$\beta_c$ fusion protein constructs are indicated. The GST-$\beta_c\Delta$SacI construct ends at the first of the two SacI sites shown. Numbering of nucleotides is from the first nucleotide used in each of the GST-$\beta_c$ fusion protein constructs.

[34], three smaller fusion protein constructs were made. Each construct contains the Box 1 and Box 2 domains (FIG. 5). [30] Because it was not known whether amino acids C-terminal of the Box 2 domain might be important for optimum binding of JAK2 to $\beta_c$, three constructs were made simultaneously so as to obtain the largest fusion protein that could be purified intact.

Three distinct 3' truncated minigenes for $\beta_c$ were constructed from pGEX5X-$\beta_c$ by digestion with BglII and NotI, SacI and NotI, and SmaI and NotI, respectively, (shown in FIG. 5), blunt-ending with T4 DNA Polymerase (BRL) and recircularization. The three resulting plasmid constructs are denoted pGST-$\beta_c$ΔBglII, pGST-$\beta_c$ΔSacI, and pGST-$\beta_c$ΔSmaI.

Figure 6:
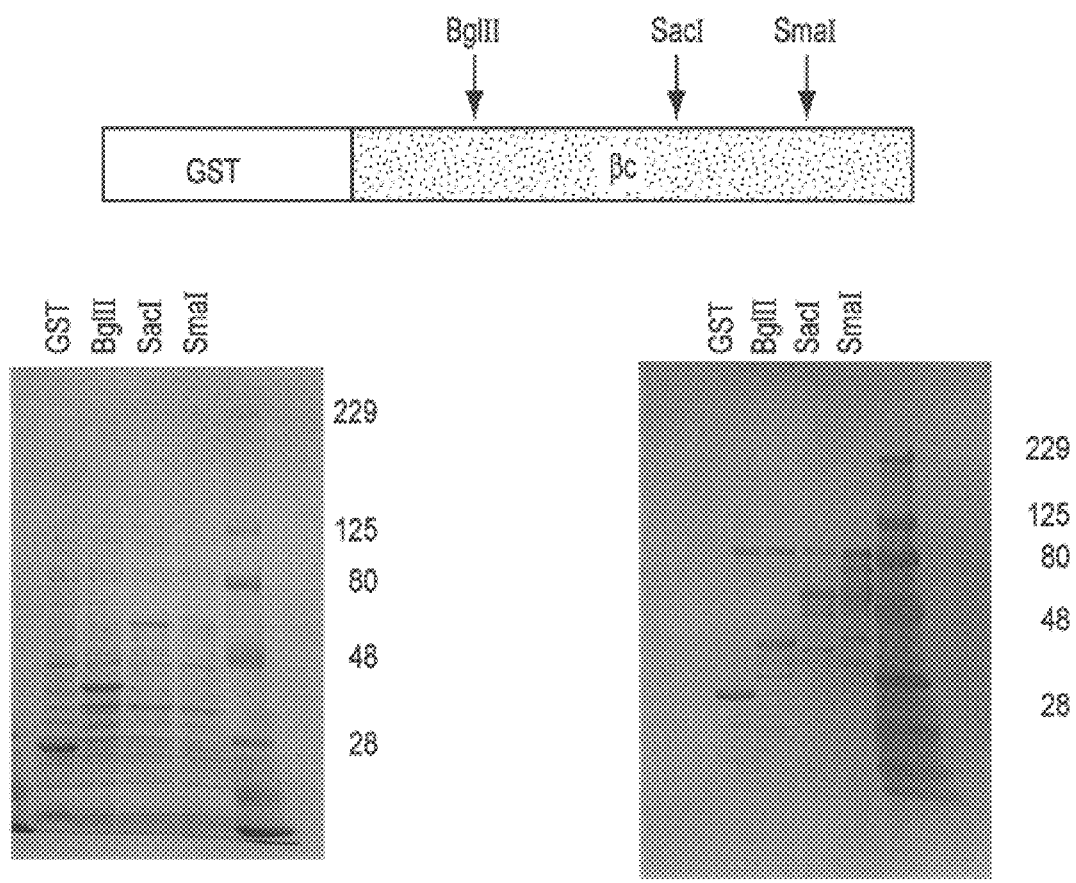
FIG. 6 illustrates GST-$\beta_c$ fusion proteins expressed in *E. coli*. Top, a schematic diagram of the three GST-$\beta_c$ fusion proteins. Left panel, a Coomassie Blue-stained polyacrylamide gel of total *E. coli* extracts shows that GST alone, GST-$\beta_c\Delta$BglII, and GST-$\beta_c\Delta$SacI are the major cellular proteins. Right panel, an immunoblot of a gel identical to that on the left stained with anti-GST-$\beta_c$ antibody shows that GST-$\beta_c\Delta$SmaI is produced but is degraded into smaller forms. Molecular weight standards are visible in the right-hand lane of each panel, and their molecular weights ($M_r \times 10^{-3}$) are indicated.

Analysis of expression cultures by SDS-PAGE showed Coomassie-staining bands for the GST-Δ$\beta_c$BglII and GST-$\beta_c$ΔSacI constructs of the correct size, amounting to 5–10 percent of total cell protein (FIG. 6). The GST-$\beta_c$ΔSma construct expressed a smaller amount of intact protein detectable only by western blotting. Western blotting also showed that all three of the expressed proteins were subject to proteolysis in vivo, and the extent of proteolysis correlated roughly with the size of the expressed protein. Attempts (as described above) to limit the extent of proteolysis by varying the culture temperature, time of induction, concentration of IPTG, and use of protease deficient host strains were unsuccessful.

Figure 7:
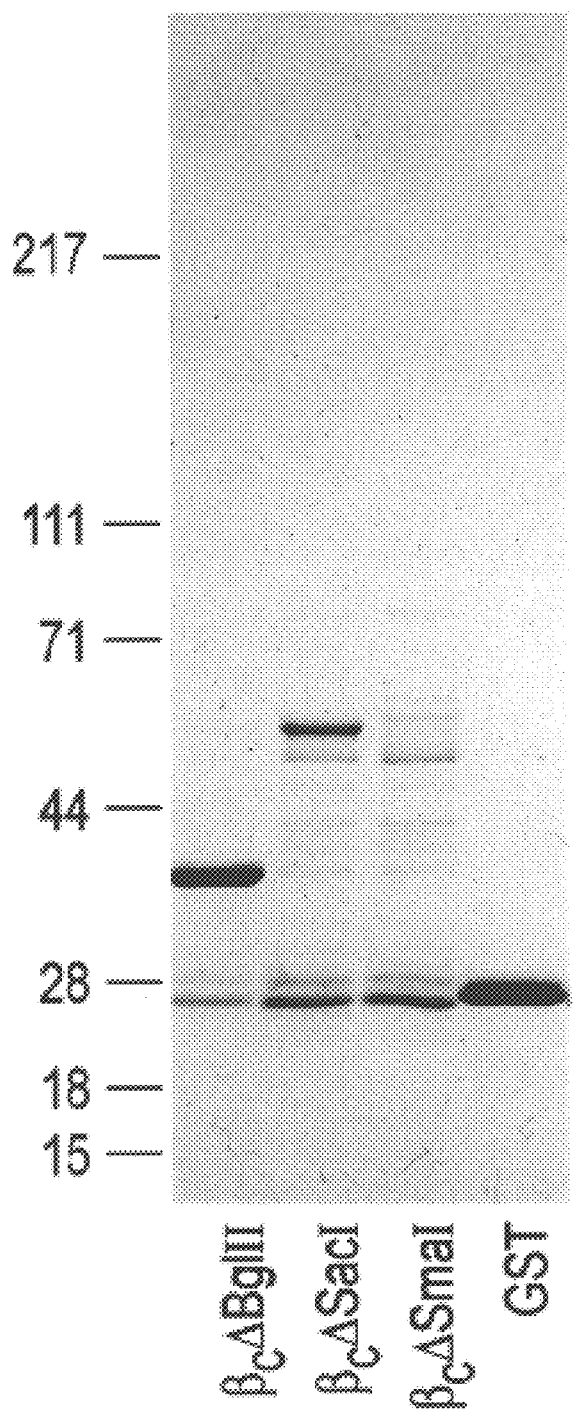
FIG. 7 illustrates purified GST-$\beta_c$ fusion proteins. Two micrograms of purified GST-$\beta_c$ fusion proteins and GST alone were separated by SDS-PAGE and stained with Coomassie Blue. Molecular weight standards ($M_r \times 10^{-3}$) are indicated.

All three fusion proteins were easily purified by glutathione-Sepharose affinity chromatography (FIG. 7). The yield was approximately 1–2 mg(L of culture. No additional degradation was observed over that seen in *E. coli* lysates. Because these fragments can bind to and be eluted from glutathione-Sepharose, they must result from clipping within the C-terminal $\beta_c$ portion of the fusion. If the N-terminus, which consists of the GST portion, were degraded, the proteins would not bind to glutathione-Sepharose.

EXAMPLE 5

Expression and Purification of Recombinant Proteins

To create a suitable strain of *E. coli* constructed for expression of the above-identified plasmid constructs, an *E. coli* progenitor strain was obtained from the American Type Culture Collection and was designated ATCC e23716. This strain is lysogenic for the bacteriophage lambda and also harbors the F plasmid (Bachmann, B. J., Bact. Rev. 36:525–557 (1972)).

The lambda lysogen was removed from the strain. This was accomplished by the P1vir bacteriophage transduction technique as described by Miller, J. H. in Experiments in Molecular Genetics, Cold Spring Harbor Laboratory (1972). The P1vir bacteriophage is available as a part of the "Experiments with Gene Fusion Strain Kit" from the Cold Spring Harbor Laboratories, Cold Spring Harbor, N.Y.

Bacteriophage P1vir was grown up on *E. coli* strain CGSC 6180 which is available from the Coli Genetic Stock Center, c/o Dr. Barbara Bachmann, Yale University, New Haven, Conn. This strain is not lysogenic for the bacteriophage lambda, and contains a Tn10 element inserted into the nadA gene (which encodes the A protein of the quinolinate synthetase) and is located adjacent to the integration site of the bacteriophage lambda. The Tn10 element destroys the nadA gene and causes the cell to be dependent on an exogenous source of nicotinamide. The Tn10 element carries a gene which codes for resistance to tetracycline. The P1vir lysate from CGSC 6180 (nadA::Tn10) was used to transduce the nadA::Tn10 allele into the ATCC e23716 by selecting for resistance to tetracycline. A number of colonies from the selection were tested for recombinational loss of the adjacent lambda phage by sensitivity to bacteriophage T4rII (Benzer, S., Proc. Natl. Acad. Sci. USA, 47:403–408 (1961)). The nadA::Tn10 allele was removed by growing P1vir on W3110 strain (available from the Coli Genetic Stock Center, New Haven, Conn.) which has the normal nada gene and is not lysogenic for lambda. Selection for the normal nadA allele was performed by plating the cells on a medium that was not supplemented with nicotinamide.

Next the F plasmid was removed by growing cells in the presence of 4 μg/ml rifampicin for multiple generations. Cells that had lost the F plasmid were identified by their inability to support the growth of the F plasmid-specific bacteriophages (Caro, L. G. and M. Schnos, Proc. Natl. Acad. Sci. USA, 56:126–131 (1966)). The resultant strain was designated K12S.

Plasmids encoding either GST (as a negative control) and the three plasmid constructs from Example 4 (pGST-$\beta_c$ΔBglII, pGST-$\beta_c$ΔSacI, and pGST-$\beta_c$ΔSmaI) were transformed into competent K12S cells by selecting for ampicillin resistance. [47] Cells expressing these three proteins were diluted 1:100 from an overnight culture into either L Broth or Terrific Broth (Gibco BRL, Gaithersburg, Md.) supplemented with 100 μg/ml ampicillin, and grown at 30° C. to an $OD_{550}$ of approximately 0.5. IPTG was added to a final concentration of 1 mM, and the culture was further grown for 2–4 hours. Cells were collected by centrifugation and stored as frozen cell pellets until needed.

The cell pellets were dissolved in SDS loading buffer and subjected to SDS-PAGE after which all proteins were transferred to nitrocellulose (Optitran, Schleicher & Scheull) using the method of Towbin et al [45] at approximately 0.2 ODU of cell lysate per lane. The nitrocellulose filters were incubated with anti-$\beta_c$-GST (UBI) and peroxidase-coupled goat anti-rabbit IgG (Boehringer-Mannheim, Indianapolis, Ind.), and bands representing GST or GST/$\beta_c$ fusion proteins were visualized using hydrogen peroxide and 4-chloro-1-napthol as described. [48]

Fusion proteins were purified by affinity chromatography on glutathione-Sepharose using the Bulk GST Purification Module (Pharmacia Biotech, Uppsala, Sweden). *E. coli* cell pastes were lysed by sonication and 1% Triton X-100 treatment as described by Pharmacia Biotech, Uppsala, Sweden, or by treatment with 100 μg/ml lysozyme, 1% Triton X-100, and 100 μg/ml DNase for 10–30 minutes at room temperature.

EXAMPLE 6

Generation of JAK2 Protein and Cloning of a Human JAK2 cDNA Fragment

Figure 8:
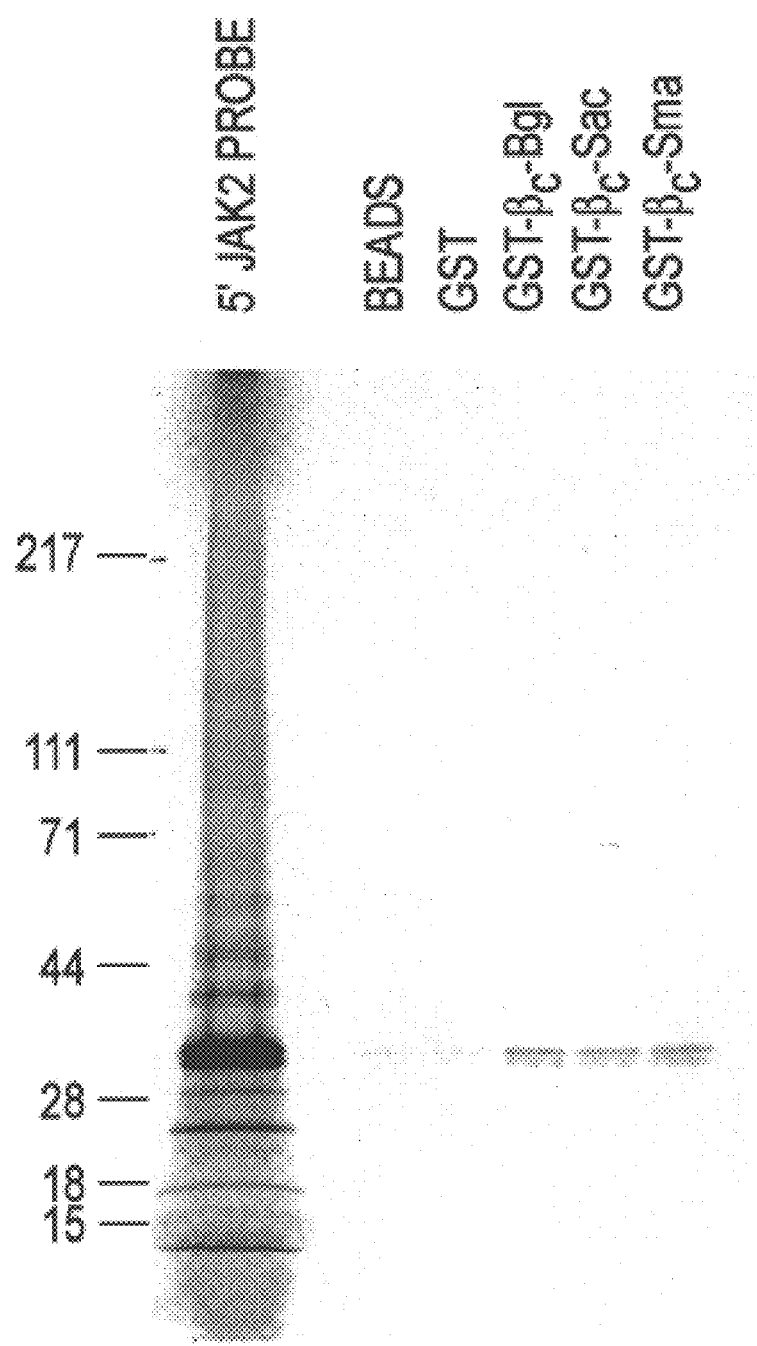
FIG. 8 illustrates $^{35}$S-JAK2 binding to GST-$\beta_c$ fusion proteins. Shown is an autoradiograph of an SDS-PAGE gel with 5 μl of in vitro-translated $^{35}$-JAK2 in the left lane. The remaining lanes contain solubilized glutathione-Sepharose beads alone (Beads) or beads bound to GST or GST-$\beta_c$ fusion proteins, as indicated, after incubation with 5 μl of $^{35}$S-JAK2 followed by washing. This autoradiograph was exposed for six days.

The N-terminal 294 amino acids of JAK2 are sufficient for binding of JAK2 to $\beta_c$. [40] JAK2 cDNA encoding the first 294 amino acids was amplified from human TF-1 cell cDNA using PCR primers based on mouse JAK2 sequence. Following subcloning into a suitable vector (i.e., any vector containing an SP6, T3 or T7 RNA polymerase promoter site), the JAK2 cDNA was transcribed and translated in vitro in the presence of $^{35}$S-methionine to yield $^{35}$S-labeled N-terminal JAK2 (FIG. 8).

As in Example 4, RNA was prepared from the IL-3-dependent TF-1 cell line (obtained from American Type Tissue Collection, Rockwell, Md., ATTC Accession No. CRL-2003) [46] using Tri-Reagent according to the manufacturer's instructions (Molecular Research Center, Inc., Cincinnati, Ohio). Total RNA (2.5 µg/reaction) was used to synthesize cDNA using the Superscript Preamplification System for First Strand cDNA Synthesis (Gibco BRL, Gaithersburg, Md.). Separate reactions were performed using either oligo (dT) or random hexamers as primers, and then combined.

The cDNA encoding the N-terminal 294 amino acids of human JAK2 were amplified from TF-1 cell cDNA using primers based on the published mouse JAK2 cDNA sequence [23] corresponding to nucleotides 94–123 (sense) and complementary to nucleotides 957–975 (antisense). Respectively, the following primers were used: MJ2F1 (5' AGGAATTCATGGGAATGGCCTGCCTTA-CAATGACAGAA 3') [SEQ ID NO:8] and MJ2R1 (5' TAGCGGCCGCACCGTTTCCAGTTAT-TATAATGGTTGCAA 3') [SEQ ID NO:9]. Conditions for PCR were the same as for the $\beta_c$ fragment, described above. The resulting fragment was cloned into pCRII using the T/A Cloning Kit (Invitrogen, San Diego, Calif.) to yield plasmid phjak2–5'.

Nucleotide sequencing of the subcloned PCR fragment using fluorescent dye termination sequencing on an Applied Biosystems Sequencer Model No. ABI373A yielded the nucleotide sequence [SEQ ID NO:4] shown in FIG. 9 and the deduced amino acid sequence [SEQ ID NO:5] shown in FIG. 10. This region of human JAK2 nucleotide sequence is 87 percent identical to rat JAK2 sequence, and human JAK2 amino acid sequence is 97 percent identical to rat JAK2 in this region [49]. The orientation of the JAK2 clone in pCRII is such that transcription from the T7 promoter yields sense strand RNA.

EXAMPLE 7

$\beta_c$/JAK2 In Vitro Binding Assay

A $^{35}$S-labeled N-terminal JAK2 protein fragment was generated by coupled in vitro transcription and translation of the phjak2–5' plasmid using a T7 RNA polymerase TNT kit (Promega, Madison, Wis.) in the presence of 35S-methionine (Amersham Life Sciences, Arlington Heights, Ill.). Purified GST or each of the three GST-$\beta_c$ fusion proteins were bound non-covalently to glutathione-Sepharose (Pharmacia Biotech, Uppsala, Sweden) by incubating 0.5 mg protein per 1 ml packed beads for 30 minutes at room temperature. After washing and equilibration in binding buffer (150 mM NaCl, 10 mM HEPES, pH 7.4, 0.1% Tween-20) with protease inhibitors, 25 µl of beads and 5 µl of 35S-JAK2 translation product were incubated in 600 µl binding buffer with protease inhibitors overnight at 4° C. After beads were washed three times with 1 ml cold binding buffer, bound fusion proteins and 35S-JAK2 were solubilized in SDS-PAGE loading buffer and boiled for 10 minutes.

The amount of 35S-JAK2 bound to each type of bead was revealed following SDS-PAGE and autoradiography. All three $\beta_c$ fusion proteins reproducibly bound more 35S-JAK2 than did GST-Sepharose or Sepharose beads alone (FIG. 8). Specific binding of $^{35}$S-JAK2 to GST-$\beta_c$ relative to GST alone was reproducible in the presence of various binding buffers (data not shown). The GST-$\beta_c\Delta$SmaI fusion protein degradation products bound JAK2 as well as the intact GST-$\beta_c\Delta$BglII or GST-$\beta_c\Delta$SacI proteins, presumably because only 62 or fewer amino acids of $\beta_c$ are required to bind JAK2 [24]. With these results in hand, we set out to adapt them to a high-volume screening assay where the JAK2 is used in combination with GST-$\beta_c$ fusion proteins in a scintillation proximity, fluorescence polarization, or similar assay to rapidly screen for small-molecule inhibitors of JAK2-$\beta_c$ binding.

EXAMPLE 8

$\beta_c$/JAK2 In Vitro High-Throughput Binding Assay

A. Materials and Methods

1. Generation of full-length JAK2 expression construct

A search of the Incyte database using BLAST [50] found clone 179527 to have high homology (87% over 217 bp) to rat JAK2 sequence [49]. Using methods described in WO 96/38591, this sequence information was used to create a full-length human JAK2 cDNA clone in the plasmid vector pSPORT. Nucleotide sequencing found a single nucleotide mutation that altered, relative to native JAK2 sequence, the codon of a conserved tyrosine residue at position 918 to asparagine. Native JAK2 [54] (GenBank accession number AF005216) [SEQ ID NO:21] sequence was determined by sequencing JAK2 cDNA isolated independently from human TF-1 cells.

To remove the 5' untranslated sequence for expression of JAK2, primers PSK567 (5'-GGATCCCCCGGGGGAATGGCCTGCCTTACGATGAC-3') [SEQ ID NO:23] and PSK 568 (5'-CATCAAGAAGAGGAGCTTCAGCAC-3') [SEQ ID NO:24] and were used to amplify using PCR the 5' end of JAK2 coding sequence from the full-length clone. This product was digested with SmaI and XhoI and subcloned into the JAK2-pSPORT construct that had also been digested with SmaI and XhoI. To remove the 3' untranslated region of JAK2 and add a C-terminal FLAG tag (Asp-Tyr-Lys-Asp-Asp-Asp-Asp-Lys), (SEQ ID NO: 20), primers PSK569 (5'-GTTTTCTGGTGCCTTTGAAAGACCG-3') [SEQ ID NO:25] and PSK578 (5'-GGCTATGGATCCCCCGGGCTAATTTT-TATCATCATCATCTTTATAATCTCCAGCCA TGTTATCCCTTATTTG3') [SEQ ID NO:26] were used to amplify using PCR the 3' end of JAK2 coding sequence from the full-length clone. This product was digested with BamHI and subcloned into the 5'-modified JAK2-pSPORT construct that had also been digested with BamHI.

Using U.S.E. mutagenesis (Pharmacia Biotech, Uppsala, Sweden), nucleotides 2752–2757 were altered to restore the codon for tyrosine while maintaining the amino acid composition of all other residues using oligonucleotides Y918Pvu2 (5'-GATTACGCCGACCAGCtgaaTaGCACACTCCCTTGTAC) [SEQ ID NO:27] to correct the mutation and SphI (5¹-GCTATGACGTCGCATCCACGCGTACGTAAGC) [SEQ ID NO: 28] to eliminate the SphI restriction site. This approach successfully yielded a plasmid in which the tyrosine/asparagine mutation was changed back to tyrosine.

To generate a baculovirus expression construct, PCR primers (MKO-5 5'-GATGATGATAAAAATTAGCCCGGCCGCTGCAGA TCTGATCC-3' [SEQ ID NO:29] and MKO-6 5'-GTAAGGCAGGCCATTCCCCCGGCCGCTCCGGAA TTCTAG-3) [SEQ ID NO:30] were used to amplify the transfer vector pVL1393 such that 5' and 3' JAK2 cDNA sequences were tagged onto either end of the pVL1393 multiple cloning site. PCR conditions were 95° C., for 5 min; 10 cycles of 94° C. for 10 sec, 65° C. for 30 sec, 68° C. for 8 min; then 20 cycles of 94° C. for 10 sec, 65° C. for 30 sec, 68° C. for 8 min with each cycle being extended 20 sec; then 68° C. 7 min followed by 4° C. indefinitely using Expand PCR Kit with buffer 1 (Boehringer Mannheim, Indianapolis, Ind.). This product was digested with ScaI to produce two pieces, with the 5' and 3' baculovirus recombination sequences residing in separate halves. These products and 5' and 3'-modified JAK2 cDNA that had been digested with SmaI and purified away from pSPORT vector were phosphorylated with T4 polynucleotide kinase and subjected to PCR (same conditions as above) to generate a linear piece of DNA containing JAK2 cDNA flanked by baculovirus recombination sequences.

This product was used with BaculoGold baculovirus (Pharmingen, San Diego, Calif.) to co-transfect adherent Sf9 insect cells using a standard Lipofectin (GIBCO-BRL, Gaithersburg, Md.) transfection protocol [51].

The transfection supernatant was harvested 5 days later followed by a plaque assay to isolate individual plaques [51]. Ten of these plaques (viruses) were amplified and used to infect Sf21 cells and screened by PCR and western blotting for JAK2 DNA and protein expression. Baculoviruses shown to have JAK2 inserts and JAK2 protein expression were scaled up to I liter and viral DNA isolated for DNA sequencing.

Budded virus was isolated for viral DNA purification by pelleting virus particles from 90 ml of 1.0 liter virus stock by centrifugation at 80,000×g for 90 min at 4° C. (24,000 rpm, SW28 rotor). Viral DNA was purified using a Qiagen Genomic DNA Purification Kit (QIAGEN), Santa Clara, Calif.) with the following modifications: the budded virus pellet was resuspended in 5 ml Buffer G2 by vortexing 10–30 sec (maximum speed) then 95 ul Qiagen Protease was added and incubation was a 50° C. for 60 min to remove proteins and expose the viral DNA. Column purification was per the manufacturers protocol on a midi prep column Qiagen tip-100/G. Yield was ~0.5 ug viral DNA/ml virus stock as determined by $A_{260nm}$. This DNA was sequenced to verify the authenticity of the final baculovirus construct.

2. Ultracentrifugation of immunoaffinity purified recombinant human JAK2

Recombinant JAK2 protein containing the Flag affinity label (DYKDDDDK) [SEQ ID NO:20] was expressed in either SF9 or HI-5 cells as described. Cells were lysed by dounce homogenization (20 strokes) in 1X phosphate buffered saline (PBS), pH 7.5 at 4 C. Clarified extract was passed through an anti-Flag immunoaffinity column (Kodak, New Haven, Conn.) and purified recombinant JAK2 was eluted by competition with a solution of Flag peptide at a concentration of 250 ug/ml in 1×PBS. Purity was characterized by a single band on SDS polyacrylamide gels. For some experiments, the JAK2 protein (0.15 mg/ml), aliquoted into 7 equivalent tubes, was then subjected to ultracentrifugation in an Airfuge using an A-110 rotor at an average of 164,000×g for a period of 6 hours at ambient temperature. At zero time, and at each subsequent hour thereafter, a tube of JAK2 was removed for analyses (ELISA, SDS polyacrylamide gel electrophoresis, and Western blotting).

3. Determination of recombinant JAK2 protein remaining soluble following ultracentrifugation Aliquots of the above supernatants were removed and subjected to an ELISA assay. Each solution was diluted 1:50 with 0.1M sodium carbonate, pH 9.0, and applied in multiple concentrations to a 96 well plate. After an overnight incubation, each well was washed with 0.1% BSA in 1×PBS, pH 7.5 (wash buffer), followed by continued incubation for an additional hour at 4 C. The wells were then incubated with 150 ul of C20 anti-JAK2 antibody (Santa Cruz Biotechnology, Santa Cruz, Calif.) in wash buffer for 1 hour at 4 C., followed by extensive washes with wash buffer. Secondary antibody (150 ul of alkaline phosphatase labeled goat anti-rabbit IgG (Promega, Madison, Wis.) at a dilution of 1:2000) was applied for 1 hour at 4 C., followed by extensive washes with buffer. Finally, wells were incubated with 0.1 M Tris HCl, 5 mM MgCl2, pH 9.5, and then with the same buffer (150 ul) containing 5 mg/ml p-nitrophenylphosphate (pNPP). Color formation was read by a SpectraMax 250 plate reader set at an absorbance of 405 nm. The linear phase of each concentration curve was chosen for each of the time points (0,1,2,3,4,5,and 6 hours of ultracentrifugation) in order to calculate the relative amount of recombinant JAK2 remaining in the supernatant of each fraction.

4. Labeling of JAK2 with $^3$H

Three different labeling reactions were done using $^3$H-N-succinimidyl propionate ($^3$H-NSP, Amersham Life Sciences, Arlington Heights, Ill.). One reaction was done using 0.5 mg of purified JAK2 in 0.1 M borate buffer, pH 8.5, with a reaction volume of 150 $\mu$l and an incubation time of one hour on ice with dried 1 mCi of $^3$H-NSP (toluene was removed using a stream of nitrogen) [52]. It yielded labeled JAK2 with a specific activity of about 18 Ci/mmole. Another reaction was done using the buffer 0.1 M sodium phosphate, pH 8.0, and a similar volume as before. One milligram of JAK2 in 1.2 ml of phosphate buffer was incubated for three hours on ice. This reaction yielded a specific activity of 23 Ci/mmole. A third reaction was done using 2.5 mg of purified JAK2 in 0.1 m sodium phosphate, pH 8.0, and 2.5 ml volume. It was incubated with 5 mCi of dried $^3$H-NSP on ice for 2 hours. It yielded a specific activity of 39 Ci/mmole. All three products were separated from unincorporated label using PD-10 columns (Pharmacia Biotech, Uppsala, Sweden) pre-equilibrated with 20 mM Tris, pH 8.0, 0.15 M NaCl. From the results of these three labelings, the conclusions were drawn that use of the phosphate buffer yields as good a labeling if not better than the borate buffer and that incubating for greater than one hour did not increase the specific activity. Doubling the amount of $^3$H-NSP used doubled the resulting specific activity.

The protein concentration of the labeled JAK2 was determined using Micro BCA protein assay (Pierce Chemical, Rockford, Ill.) as per manufacturer instructions in a 96-well plate which was sealed and read on a Molecular Devices Thermo Max plate reader.

5. Synthesis of Biotinylated Peptides a. Synthesis of peptides from Boc-protected amino acids Stepwise, solid-phase peptide synthesis [53] was performed on an Applied Biosystems (Foster City, Calif.) 430A Peptide Synthesizer. The t-butyloxycarbonyl (Boc) group was used as the $N^\alpha$-amino protecting group, temporary side-chain protecting groups were as follows: Arg(Tos), Cys(4-CH$_3$Bzl), Glu(OBzl), His(Bom), Lys(Cl—Z), Ser (Bzl), Trp(CHO), and Tyr(Br—Z). The side-chains of the other amino acids were not protected. Each residue was double coupled then capped with acetic anhydride before the next double couple cycle. After removal of the N-terminal Boc group the resin bound peptides were biotinylated using NHS-Biotin (Pierce Chemical, Rockford, Ill.) and DIEA in DMF for 24 hours at room temperature. The biotinylated resin bound peptides were then cleaved from the resin and temporary side-chain protecting groups removed by treatment with HF/anisole/1,4-butanedithiol (10:2:1) for 1 hr at −5° C. The crude peptides were purified by preparative reverse phase chromatography on a Vydac C-18 column (27.5×250mm) using a water/acetonitrile gradient, each phase containing 0.1% TFA (Vydac, Hesperia, Calif.). Clean fractions as determined by analytical HPLC, were pooled and the acetonitrile was evaporated under reduced pressure. The aqueous solutions were then lyophilized. The purified peptides were characterized by open access electrospray mass spectroscopy.

b. Synthesis of peptides from Fmoc-protected amino acids

Stepwise, solid-phase peptide synthesis was performed as above. The 9-fluorenylmethyoxycarbonyl (Fmoc) group was used as the $N^a$-amino protecting group. Temporary side-chain protecting groups were: Arg(Pmc), Asn(Trt), Glu (OtBu), Lys(Boc), Ser(tBu), Trp(Boc), Tyr(tBu). The side-chains of the other amino acids were not protected. Each residue was single coupled using a HBTU/NMP protocol. After removal of the N-terminal Fmoc group the resin bound peptides were biotinylated as above except NHS-LCBiotin was used. The biotinylated resin bound peptides were cleaved from the resins and temporary side-chain protecting groups were removed by treatment with 95% TFA/5% scavengers (ethylmethylsulfide/anisole/1,2-ethanedithiol, 1:3:1) for 2 hours at room temperature. The crude peptides were precipitated from the cleavage solution with cold diethyl ether. The precipitated peptides were collected on sintered glass funnels, washed with diethyl ether, dissolved in dilute acetic acid and evaporated to dryness under reduced pressure. The residue was dissolved in acetic acid and lyophilized. The crude peptides were then purified and characterized as described above.

6. SPA Assay

The assay was set up in 96-well plates (Wallac, catalog # 1450-401), Turku, Finland, using a total assay volume of 200, µl/well. Triplicate reactions were done for each data point. The buffer used in all the assays was 35 mM sodium phosphate, 150 mM NaCl, pH 8.0, 10% glycerol. Biotinylated peptides were allowed to bind to streptavidin-coated SPA beads (Amersham Life Sciences, Arlington Heights, Ill., catalog # RPNQ0006) with either less than saturating peptide or excess peptide. For 400 µg SPA beads used per reaction, there was the capacity to bind 49 pmole of biotin (given the binding capacity of 121 pmole biotin/mg bead). Under less than saturating conditions, beads and 40 pmole peptide were added to the assay plate well and incubated for one hour with gentle shaking on a Titer plate shaker (Lab-Line Instruments, Inc., Melrose Park, Ill.) at 600 rpm and not washed. Under conditions of excess peptide, beads and peptide (80 pmole of peptide per 400 µg of bead) were mixed in batch with or without 1 mg/ml K-casein added as described in Results and Discussion, incubated for one hour with rotation, washed three times with buffer and aliquotted into wells. $^3$H-JAK2 or $^3$H-NJAK2 and any other components to be tested were added and the reactions were mixed and incubated for one hour in the dark at room temperature. The plates were then read on a MicroBeta (Wallac) set to read scintillation due to tritium.

7. ELISA Method $\beta_c$ peptides corresponding to the proposed JAK2 binding domain (Table 1) were serially diluted and bound 16 hours at room temperature to streptavidin coated 96-well plates (Boehringer-Mannheim, Indianapolis, Ind.) and blocked at 37° with 1% fetal bovine serum in PBS. JAK2 protein was serially diluted on the plate and allowed to bind for 1 hour at room temperature. Plates were washed between incubations with ELISA wash (PBS with 0.04% TWEEN 20). Detection was via anti-FLAG antibody (10 µg/ml, Kodak, New Haven, Conn.) followed by anti-mouse Ig conjugated to peroxidase (1:5000 dilution, Boehringer Mannheim) and 1 mg/ml 2,2'-azinobis(3-ethylbenzthiazolinesulfonic acid) (Sigma), 0.003% $H_2O_2$, 28 mM citric acid, 44 mM $Na_2HPO_4$.

B. Results and Discussion

1. Optimization of SPA

Figure 12:
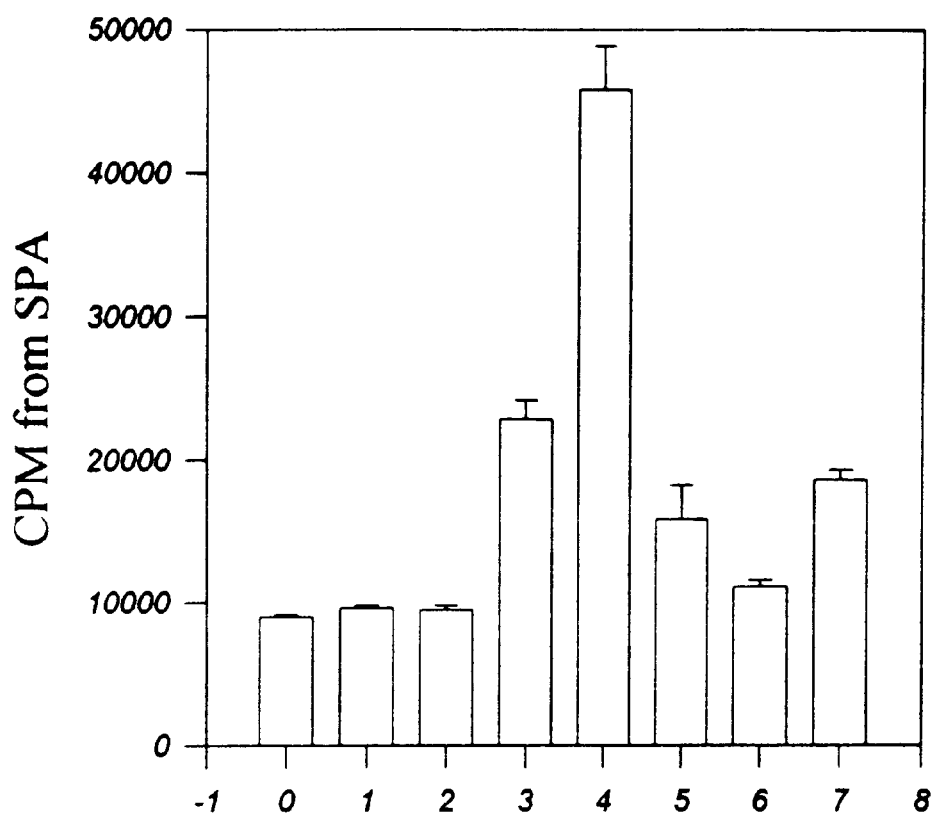
FIGS. 12 A and B illustrate results of SPA using tritium labeled full-length JAK2 [SEQ ID NO:22] (A) or NJAK2 [SEQ ID NO:5] (B) and N-terminal truncations of $\beta_c$ peptides 1–6 [SEQ ID NOS:11–16]. For both graphs, #0 is a beads only control and #1–6 are reactions with peptides 1–6 [SEQ ID NOS:11–16]. For graph A, #7 is a reaction with peptide 4 [SEQ ID NO: 14] and with 5-fold excess unlabeled JAK2. For graph B, #7 is a reaction with peptide 4 [SEQ ID NO:14] and with 10-fold excess unlabeled JAK2.
Figure 12:
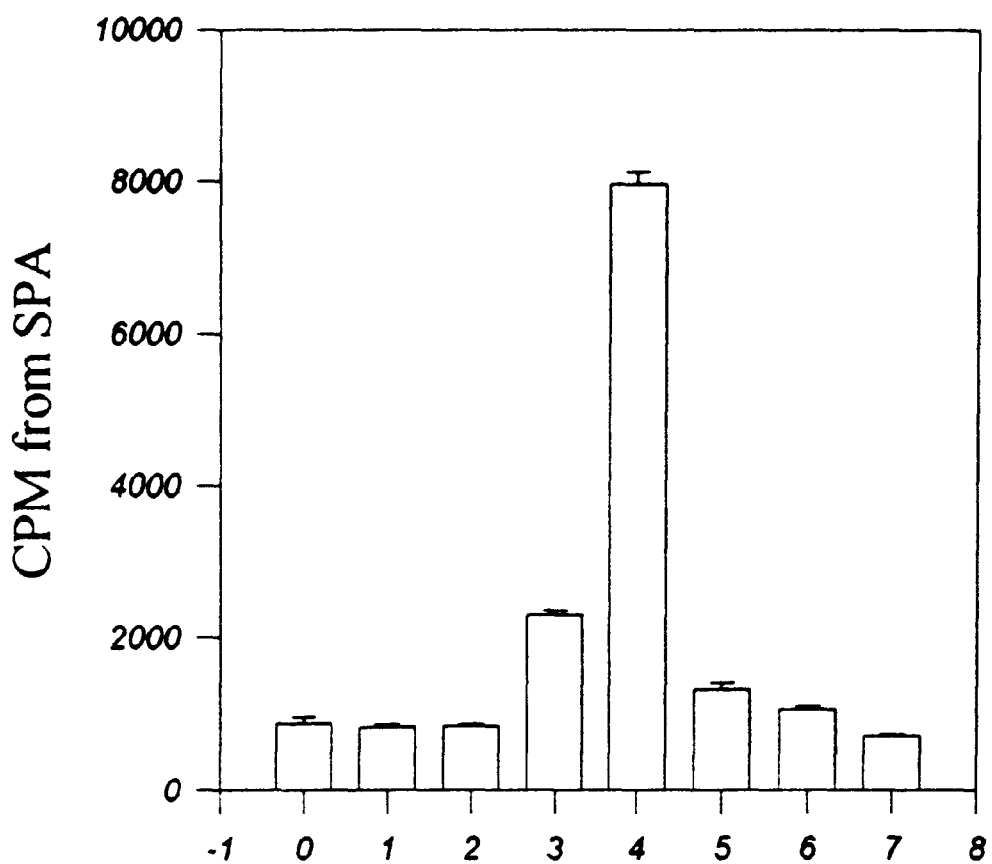

Two SPAs were done to compare the activity of $^3$H-JAK2 and $^3$H-NJAK2 in binding the $\beta_c$ peptides numbered 1 through 6 (Table 1)[SEQ ID NOS:11 through 16]. In these SPAS, beads and peptides (40 pmole per reaction) were mixed in wells of the plate and incubated as described in Materials and Methods. Either $^3$H-JAK2 or $^3$H-NJAK2 was added to the wells and, after incubation, the signals measured. The results are shown in FIG. 12. These results show that both forms of JAK2 bind the peptides with the same activity profile (that is; peptide 4>peptide 3>peptide 5>peptide 6>peptides 1 and 2 which gave no signal)[SEQ ID NOS:14, 13, 15, 16, 11 and 12, respectively]. This supports the conclusion that the N-terminal portion of JAK2 contains the region that binds $\beta_c$. A competition reaction was also done by adding 5 to 10-fold excess unlabeled JAK2 in those reactions. The results shown in FIG. 12 also illustrate that the binding of labeled JAK2 is competed significantly by 5-fold unlabeled JAK2 and labeled NJAK2 binding is reduced almost to background by 10-fold unlabeled JAK2. This shows that the binding can be competed, demonstrating that the beads with peptides bound do not just adsorb all the JAK2 nonspecifically.

Figure 13:
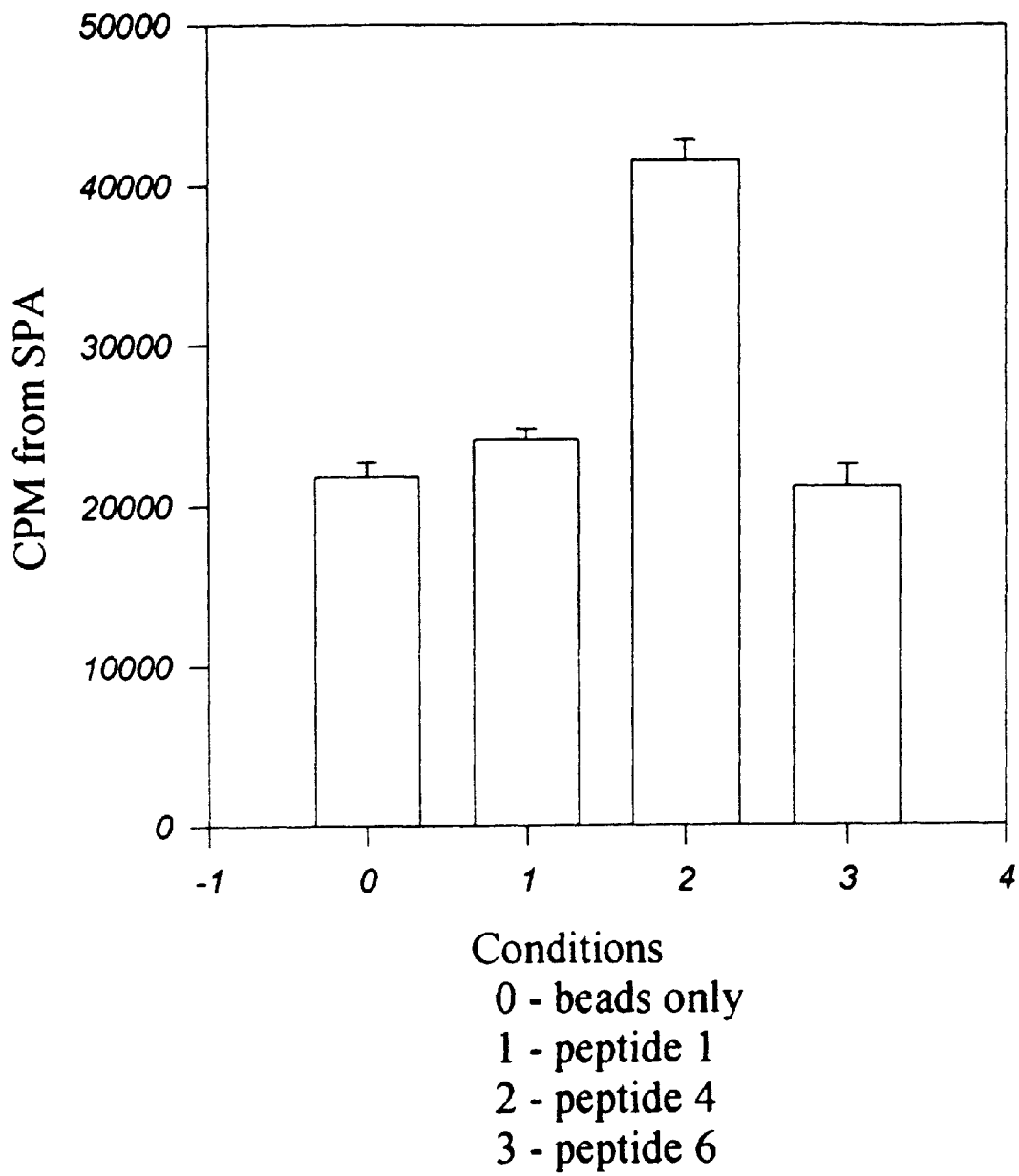
FIG. 13 illustrates results of SPA performed by mixing 3H-JAK2 and $\beta_c$ peptide prior to adding beads. #0 is a beads only control, #1 is a reaction with peptide 1 [SEQ ID NO:11], #2 is a reaction with peptide 4 [SEQ ID NO:14] and #3 is a reaction with peptide 6 [SEQ ID NO:16] as described in the specification.

Mixing peptide and labeled JAK2 for one hour prior to adding SPA beads was tested and compared to binding peptide to bead for one hour prior to adding labeled JAK2. Control reactions were set up as described in Materials and Methods and test reactions were set up by mixing peptides with labeled JAK2 prior to adding beads. These were incubated for one hour without continuous mixing then beads were added, mixed, and incubated one hour as for standard setup. The results are shown in FIG. 13. Mixing peptide and JAK2 first gave the same activity profile for peptides 1, 4 and 6 [SEQ ID NOS:11, 14 and 16] but gave lower overall signals and signal-to-noise ratios. Therefore, the protocol described in Materials and Methods was adopted as standard.

Figure 14:
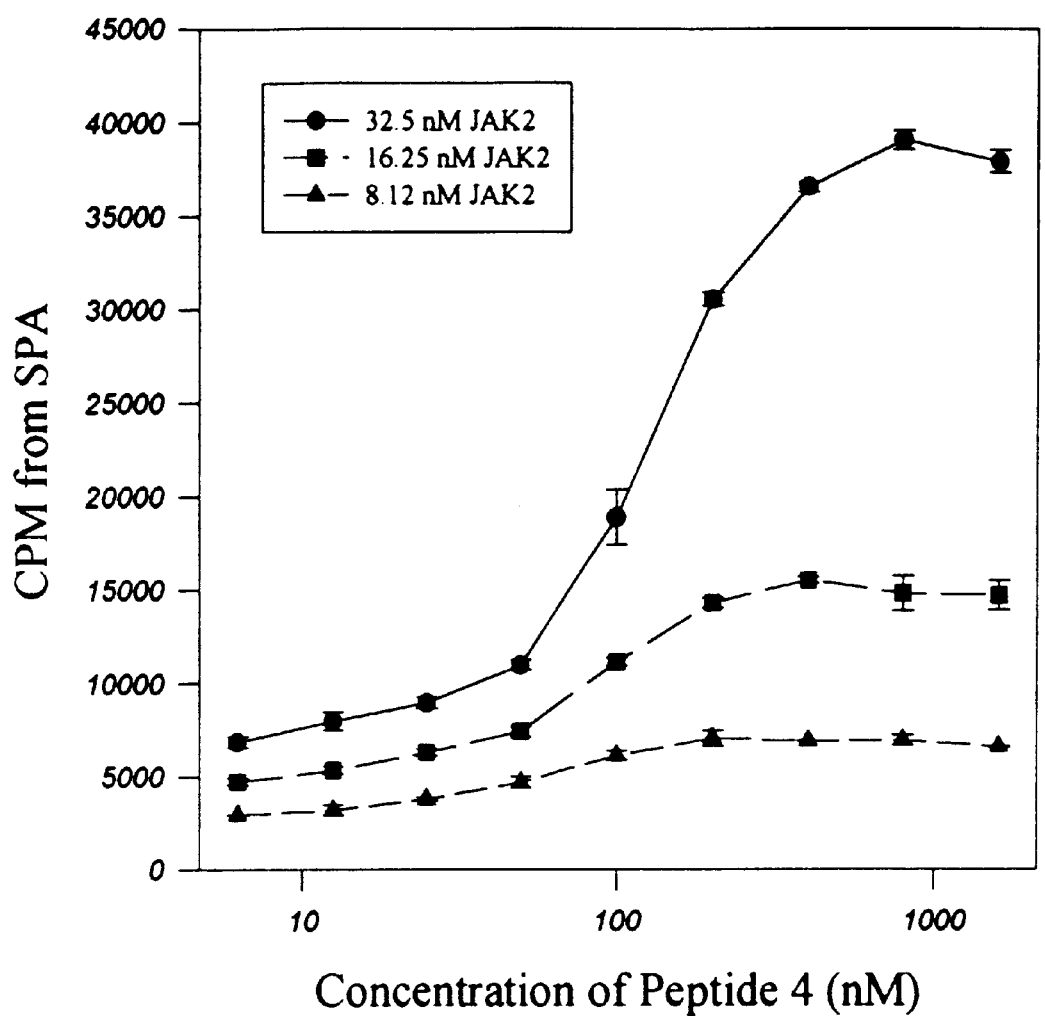
FIG. 14 illustrates results of SPA in which peptide 4 [SEQ ID NO:14] was titered (6.25 to 1600 nM) using three different concentrations of labeled JAK2 (8.12 nM, 16.25 nM and 32.5 nM).

One assay was done to minimize the amount of peptide and JAK2 that could be used in the assay and still get a good signal. Three different amounts of JAK2 were titrated with varying amounts of peptide. The results are shown in FIG. 14. The signal obtained decreases significantly when the final concentration of JAK2 in the assay decreases from 32.5 nM to 16.25 nM. So the least amount of JAK2 that can be used under these conditions is 0.86 µg or 6.5 pmole of JAK2 per reaction. That is 82 µg of JAK2 per plate and 82 mg of JAK2 for one thousand plates. Therefore, the production of sufficient JAK2 to do high-throughput screening using this assay is feasible. However, even less JAK2 is required when κ-casein is used as described below. 40 pmole of peptide 4 (0.17 µg) per reaction is sufficient under the conditions of this assay to get a signal-to-noise ratio of 4.5. This may be optimized further with the use of κ-casein. Without optimization, the assay requires 16 µg of peptide per plate or 16 mg for one thousand plates to give a signal-to-noise ratio of 4.5. So without further optimization, this assay is feasible for high throughput screening from the perspective of the amounts of peptide and JAK2 needed for the assay.

Figure 15:
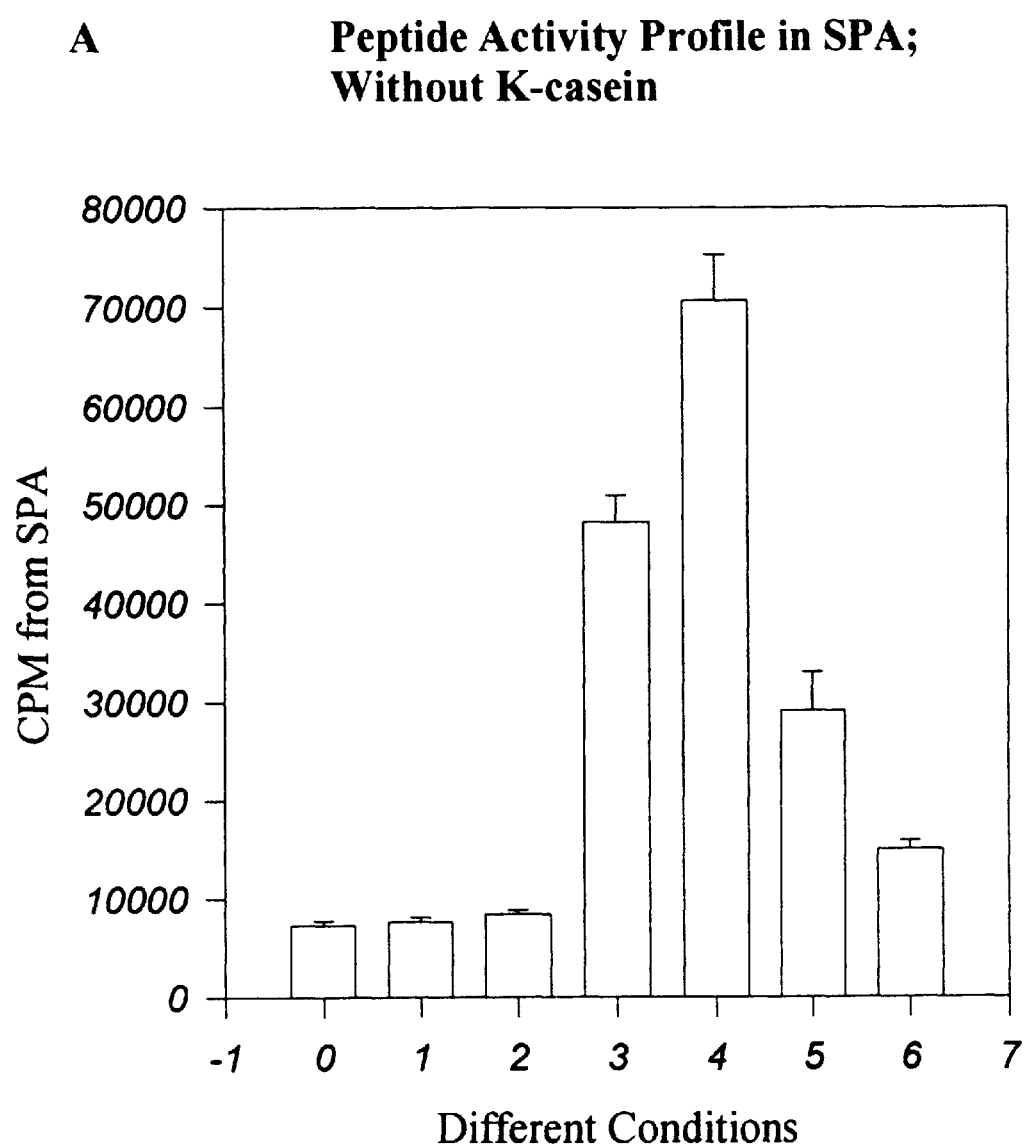
FIGS. 15 A and B illustrate the effect of κ-casein on signal-to-noise ratio in SPA. #0 is a beads only control, #1–6 are reactions with peptides 1–6 [SEQ ID NOS:11–16]. The reactions for graph A did not contain κ-casein and the reactions for graph B contained 1 mg/ml κ-casein in the step binding peptide to bead as described in Materials and Methods of Example 8.
Figure 15:
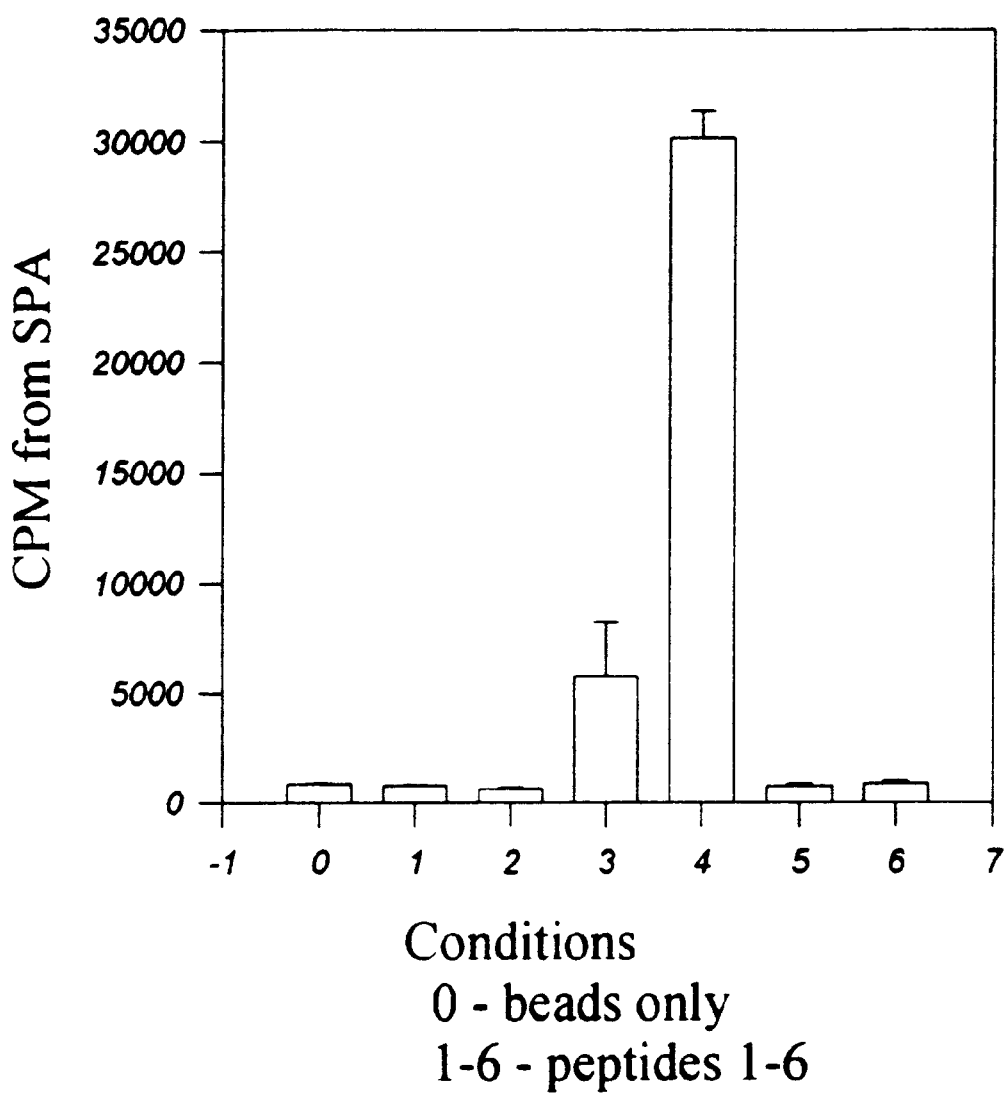
Figure 16:
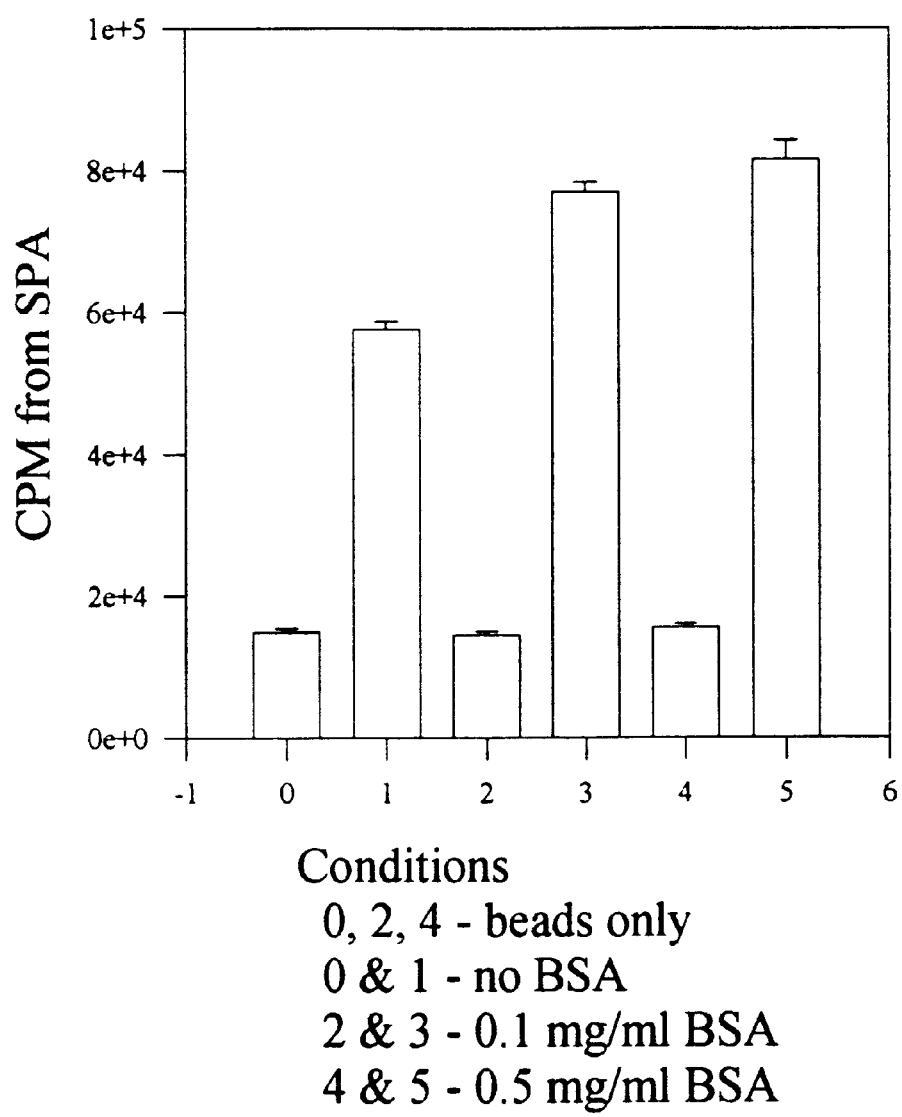
FIG. 16 illustrates the effect of BSA on signal-to-noise ratio in SPA. The reactions for #0, 2 and 4 in the graph are beads only controls. The reactions for #1, 3 and 5 had less than saturating peptide 4 [SEQ ID NO:14] bound to beads. #0 and 1 contained no BSA, #2 and 3 contained 0.1 mg/ml BSA and #4 and 5 contained 0.5 mg/ml BSA.

The use of blocking agents in the SPA was tested to further improve the signal-to-noise ratio. Two SPAs were done to test maximizing the amount of peptide on the beads with or without κ-casein. It was also found that when κ-casein was included throughout the assay using peptides 1 and 6 [SEQ ID NOS:11 and 16], very little signal was obtained (data not shown). So, to test the ability of κ-casein to block nonspecific binding to the bead, it was added during binding of excess peptide to the beads as described in Materials and Methods and washed away before the beads were used in the assay. The results of these two assays are shown in FIG. 15. They show the same activity profile of the peptides and demonstrate that κ-casein used in this way decreases both signal and background. The signal-to-noise ratio with peptide 4 [SEQ ID NO:14] and no κ-casein is 10 and with κ-casein is 35. Therefore, κ-casein improves the signal-to-noise ratio. BSA was also tested as a potential blocking agent using peptide 4 [SEQ ID NO: 14]. BSA was added to all stages of the reactions at either 0.1 mg/ml or 0.5 mg/ml. The results are shown in FIG. 16. The signal-to-noise ratio was increased from 4 for no additions to 5 with either concentration of BSA. BSA had a slight positive effect on the signal but had no effect on the background. At the assay pH of 8.0, BSA is negatively charged and κ-casein has a net neutral charge, suggesting that κ-casein may block background by blocking hydrophobic sites on the SPA beads.

2. Characterization of the Binding Observed in the SPA

Figure 17:
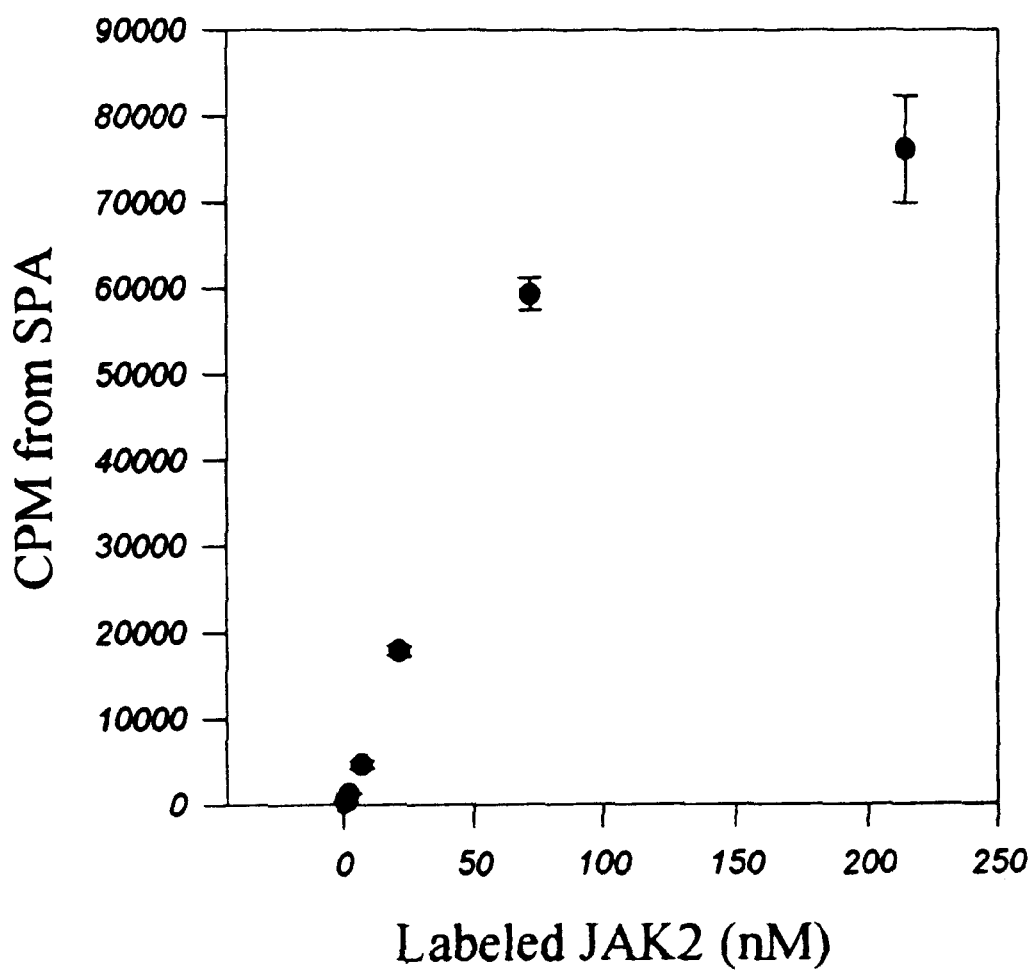
FIGS. 17 A and B illustrate binding curves using excess peptide 4 [SEQ ID NO:14] bound to beads in the presence of 1 mg/ml κ-casein. Different amounts of JAK2 were used: 0.72 to 214 nM in A and 5.5 to 33 nM in B.
Figure 17:
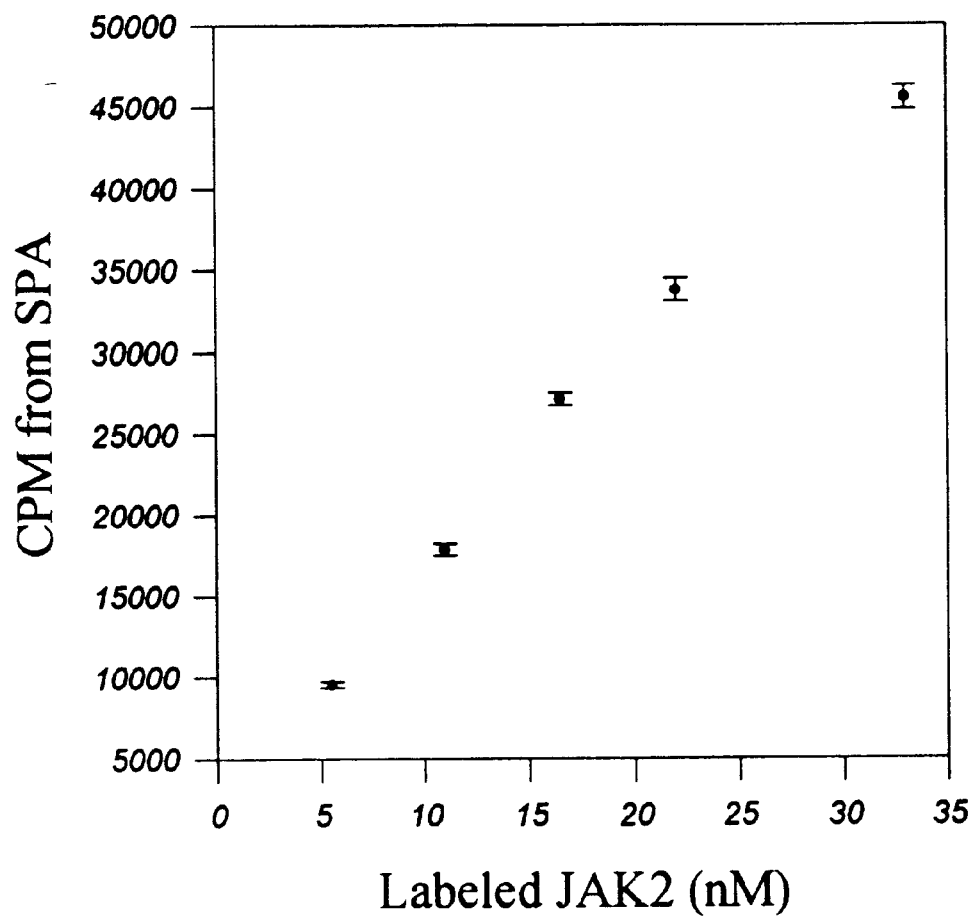

Panel A of FIG. 17 shows a binding curve using less than saturating peptide 4 [SEQ ID NO:14] and varying concentrations of labeled JAK2. The figure shows that the increase in signal with increase in JAK2 gives a very steep curve which indicates that the binding occurs with a very low apparent Kd. The curve also shows that the binding reaches saturation at about 40 pmole of JAK2 which correlates with the amount of peptide present on the beads. Another assay was done using less than saturating concentrations of JAK2. The results of that assay are shown in panel B of FIG. 17. The curve shows a linear increase in binding with increase in amount of JAK2. That again indicates that the binding is very strong. Also, it shows that with κ-casein present as little as 5.5 nM JAK2 gave a signal to noise ratio of 14. So even less JAK2 is required with κ-casein than without κ-casein as described above.

Despite its high solubility, JAK2 exhibited degrees of aggregation as measured by size exclusion chromatography (data not shown). To see whether more highly aggregated JAK2 could be separated by ultracentifugation from less aggregated or monomeric JAK2, a sample of freshly purified JAK2 at a defined concentration was centrifuged in an airfuge as described in Materials and Methods. Samples were taken at 7 different time points over a 6 hour period to assess the amount of JAK2 which remained in the supernatant phase. A determination of JAK2 remaining in the soluble phase was ascertained by ELISA as shown in table 2. After 1 hour at 164,000×g, 40 to 50% of the original JAK2 was detected, a value which remained relatively constant for up to 5 additional hours in this experiment. These data suggest that about half of the sample was of sufficient mass to precipitate almost immediately, while the remainder was of significantly lower aggregated state. Since the supernatant was removed from below the meniscus by pipetting, a determination of the molecular weight could not be established in this experiment.

Figure 18:
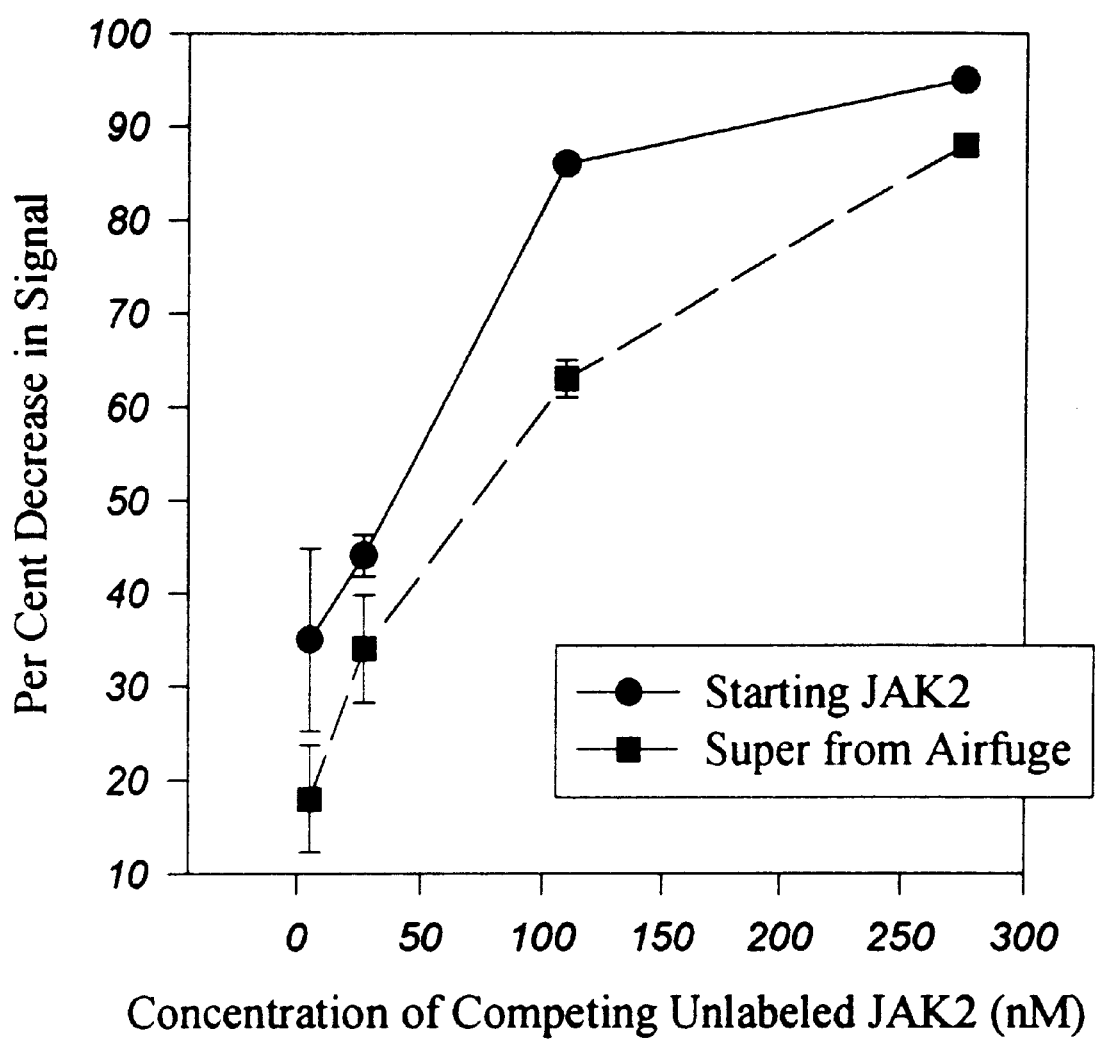
FIG. 18 illustrates graphically the competition of airfuged JAK2 fractions with labeled JAK2 in the SPA. Different amount of either JAK2 before airfuge (starting JAK2) or supernatant after airfuge of JAK2 for 6 hours (super from airfuge) were mixed with labeled JAK2 in a SPA and the resulting percent decrease in signal is shown on the graph.

While the amount of precipitate produced in the above experiment was not established, it was believed that because only 50% remained soluble as defined by ELISA, that the other 50% had precipitated. A SPA was done to test the supernatant after 1 hour of ultracentrifugation versus the original JAK2 solution to see how removing the highest aggregated material by precipitation affected the outcome of the SPA assay. Different amounts of either starting material or supernatant were used to compete for binding with labeled JAK2 by mixing unlabeled and labeled JAK2 and adding that to peptide 4 [SEQ ID NO: 14] bound to SPA beads. The percentage decrease in the signal was determined; the results are shown in FIG. 18. The JAK2 from the supernatant competed less effectively than the starting material. These data imply that the less aggregated JAK2 has a higher apparent Kd than the more aggregated JAK2. The lower apparent affinity most likely results from decreased avidity, because the less aggregated protein remaining in the supernatant would have fewer $\beta_c$ binding sites per aggregate. Alternatively, it is possible that the binding sites on the highly aggregated form of JAK2 have higher affinity for the $\beta_c$ peptide. To avoid problems related to high avidity resulting from JAK2 aggregation, one could biotinylate the aggregate and radiolabel the $\beta_c$ peptide, thus reversing the roles of each component in the scintillation proximity assay.

Figure 19:
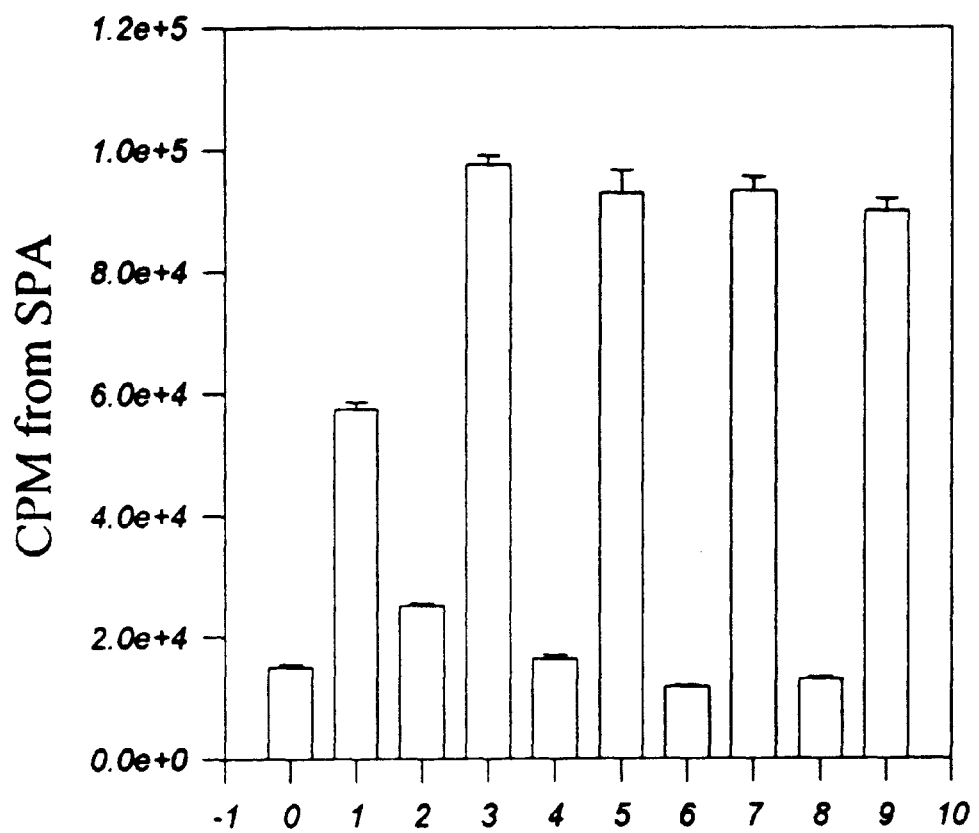
FIGS. 19 A and B illustrate the effect of various detergents and DTT on signal-to-noise ratio in the SPA. All reactions containing peptide 4 [SEQ ID NO:14] used less than saturating amount of peptide. For A, #0 is a beads only control and #1 is a peptide 4 [SEQ ID NO:14] positive control. Different detergents were added to the reactions #2–9 in A. #2 and 3 contained 0.01% Triton. #4 and 5 contained 0.003% Tween 20. #6 and 7 contained 0.0025% Brij 35. #8 and 9 contained 0.01% digitonin. For B, #0 is a beads only control and #1 is a peptide 4 [SEQ ID NO:14] positive control. 0.0025% Brij 35 was used in reactions #2–5. 0.1 mM DTT was used in reactions #2 and 3 and 1 mM DTT was used in reactions #4 and 5.
Figure 19:
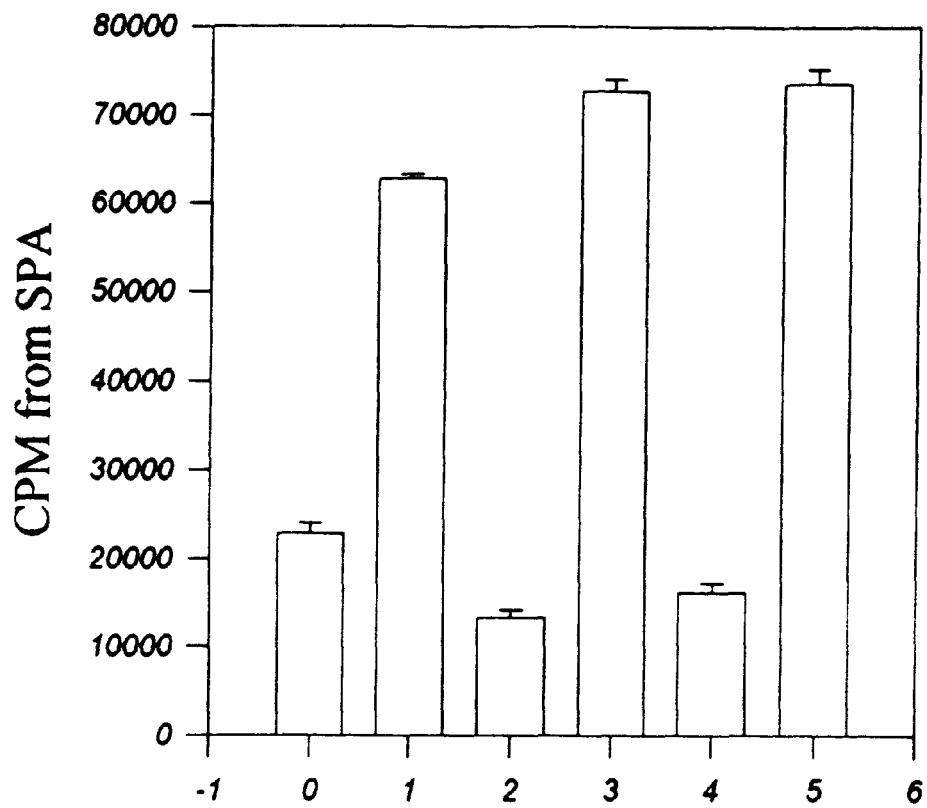

Assays were done to test whether inclusion of detergent or dithiothreitol in the SPA would have an effect on the signal by disrupting the JAK2 aggregate. An assumption was made that disruption of the aggregate would result in a weaker signal because fewer binding sites would be available on a single JAK2 entity to bind peptides on a bead, leading to decreased avidity effects. Four detergents were tested as shown in panel A of FIG. 19. The opposite effect was seen with the detergents producing an increase in signal and, with Brij 35, a decrease in background as well, improving the signal-to-noise ratio but presumably not disrupting the JAK2 aggregate. Without some biochemistry along with the SPA, it is not possible to determine what is happening with the detergents or search for a detergent or condition that disrupts the aggregate of JAK2. A second SPA using Brij 35 and two concentrations of dithiothreitol is shown in panel B of FIG. 19. Again, signal was increased and background decreased with no obvious additional effect of the dithiothreitol.

Figure 20:
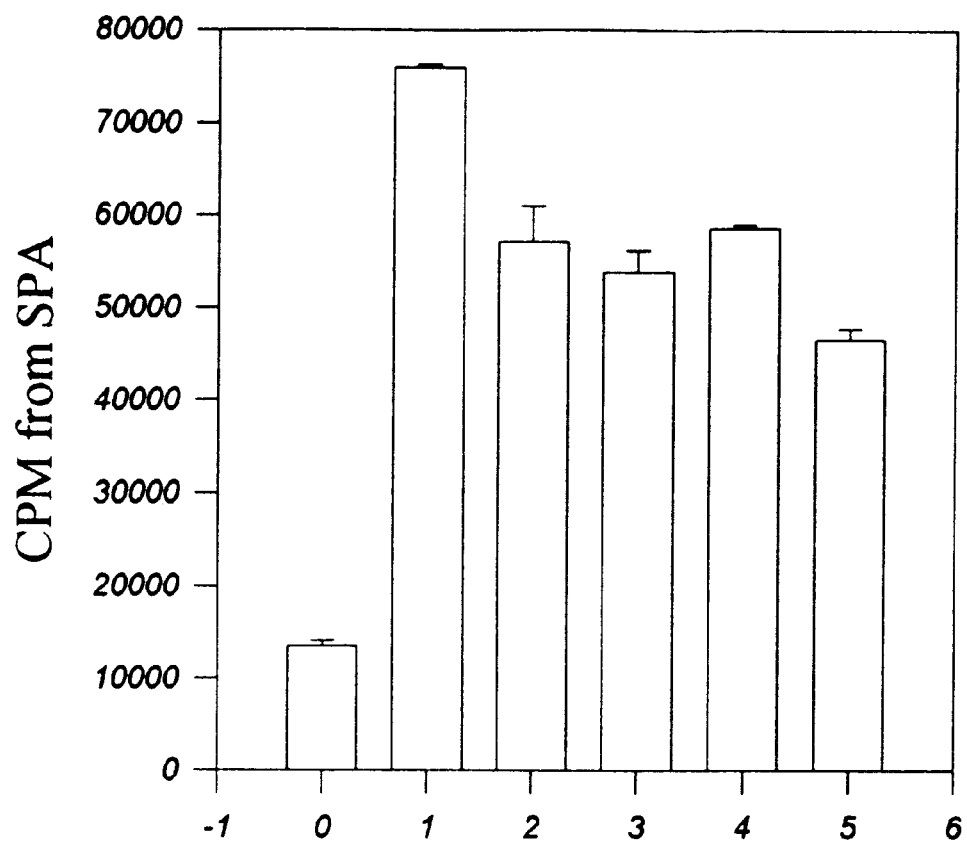
FIGS. 20 A and B illustrate a test of the ability of streptavidin-peptide 4 complexes to compete for binding of 3H-JAK2 to peptide 4-coated SPA beads. For A, #0 is a beads only control. In all reactions with peptide bound to beads, excess peptide 4 [SEQ ID NO:14] was bound to beads before adding soluble samples. The reaction in #1 is peptide 4 [SEQ ID NO:14] bound to beads only, no added peptide 4 [SEQ ID NO:14] or streptavidin. #2 contained soluble peptide 4/streptavidin at a ratio of 1:1. #3 contained soluble peptide 4/streptavidin at a ratio of 4:1. #4 contained 20 μM peptide 4 added as soluble peptide 4. #5 contained 20 μM streptavidin. The reactions for A did not contain κ-casein. For B, 0 is a beads only control. In all reactions with peptide bound to beads, excess peptide 4 was bound to beads in the presence of 1 mg/ml κ-casein (as described in Materials and Methods of Example 8) before adding soluble samples. The reaction in #1 is peptide 4 bound to beads only, no added peptide 4 or streptavidin. #2 contained peptide 1/streptavidin at a ratio of 4:1 and #3 contained peptide 4/streptavidin at a ratio of 4:1.
Figure 20:
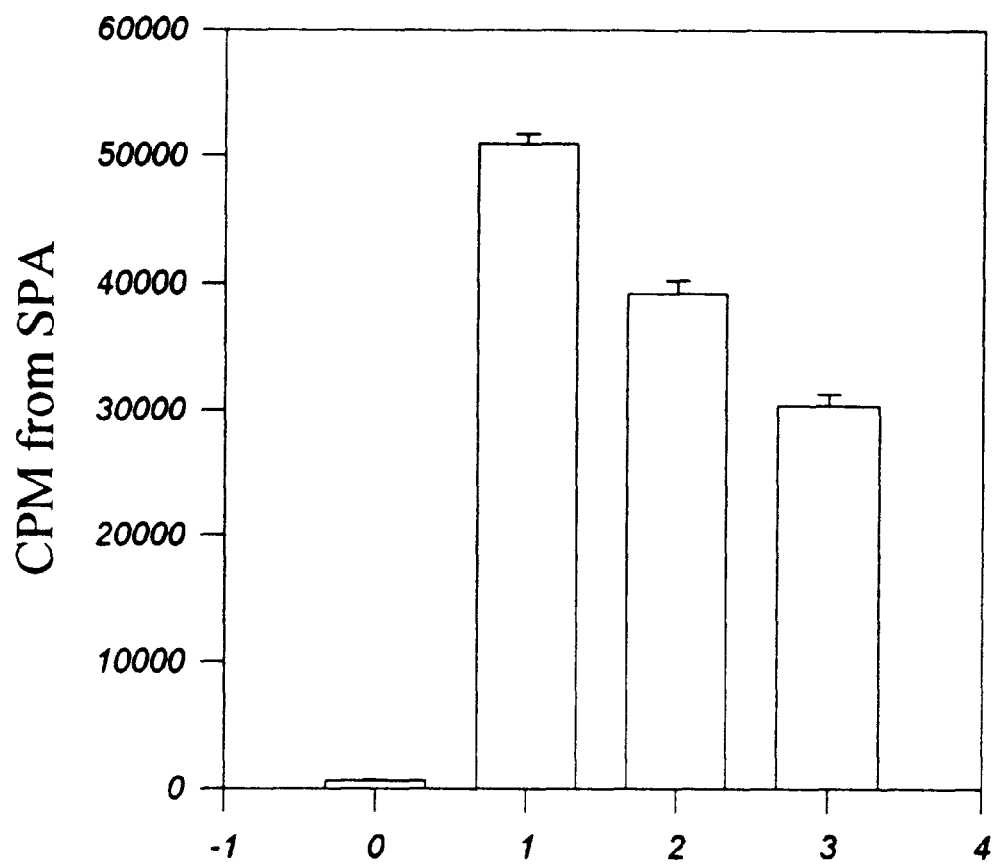

The ability of excess peptide 4 [SEQ ID NO: 14] to compete for binding of JAK2 was tested. Biotinylated peptide 4 was bound to streptavidin in solution to mimic the conditions of the peptide 4 bound to the beads. It was used at a ratio of 1:1 (peptide 4: streptavidin) and at a ratio of 4:1 to see whether having multiple peptides on one streptavidin molecule might do a better job of binding JAK2 and therefore of competing. The results shown in panel A of FIG. 20 show that only minimal, if any, competition was seen. Use of streptavidin alone decreases the signal to a greater extent than streptavidin with peptide 4 [SEQ ID NO:14] bound. This could be due to the free streptavidin pulling some of the peptide 4 [SEQ ID NO: 14] off the bead. The conclusion is that peptide 4 [SEQ ID NO: 14] in solution, whether bound to streptavidin or not, competes poorly with peptide 4 [SEQ ID NO: 14] on the SPA beads for binding JAK2. The interpretation of these results is that many peptides are bound on the surface of the bead by the JAK2 aggregate resulting in a very strong binding that peptide in solution does not mimic. Another SPA was done using peptide 4 [SEQ ID NO:14] or peptide 1 [SEQ ID NO:11] bound to streptavidin at a ratio of 4:1. In comparing peptide 4 [SEQ ID NO:14] to peptide 1 [SEQ ID NO:11], we are comparing an active peptide to an inactive peptide. The results are shown in panel B of FIG. 20. These results indicate that peptide 4 [SEQ ID NO: 14] in solution does compete for binding JAK2 but very weakly. The decrease in signal with peptide 1 [SEQ ID NO:11] bound to streptavidin is likely the result of the availability of sites on streptavidin to bind some of the peptide 4 [SEQ ID NO:14] that was on the beads because not all the sites will be occupied by peptide 1. The conclusion again is that peptide 4 [SEQ ID NO:14] in solution binds JAK2 very poorly and this implies that if monomers of JAK2 were to bind peptide 4 [SEQ ID NO:14] on beads, the binding would actually be weak.

Figure 21:
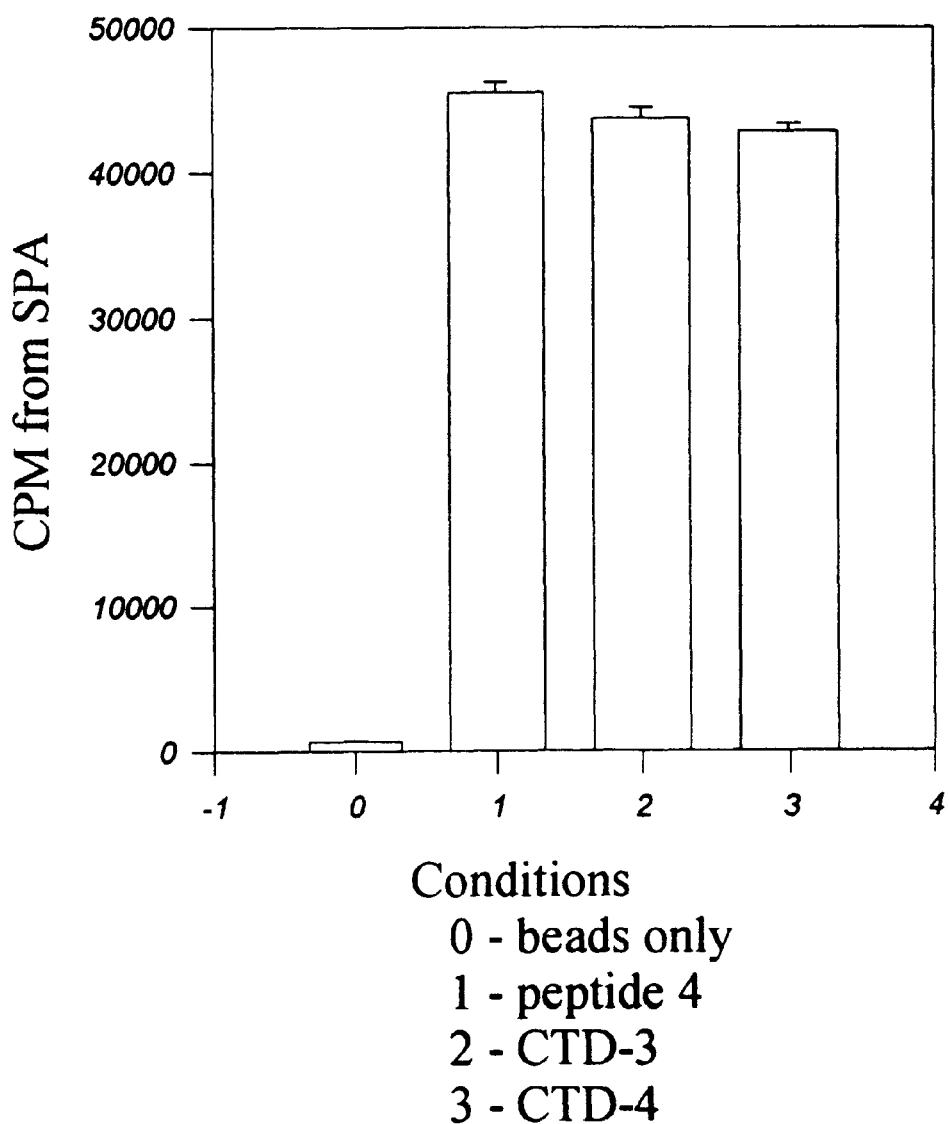
FIGS. 21 A and B illustrate the effects of C-terminal deletions of $\beta_c$ peptides on binding of $^3$H-JAK2. For A, #0 is a beads only control. In A, peptide 4 was used in reaction #1, CTD-3 [SEQ ID NO:17] in reaction #2 and CTD-4 [SEQ ID NO:18] in reaction #3. Excess peptides were bound to beads in the presence of 1 mg/ml κ-casein. 32.5 nM labeled JAK2 was used in each reaction. For B, #0 is a beads only control. In B, peptide 4 was used in reaction #1 and peptide CTD-5 [SEQ ID NO:19] in reaction #2. Excess peptides were bound to beads in the presence of 1 mg/ml κ-casein. 10 nM labeled JAK2 was used in each reaction.
Figure 21:
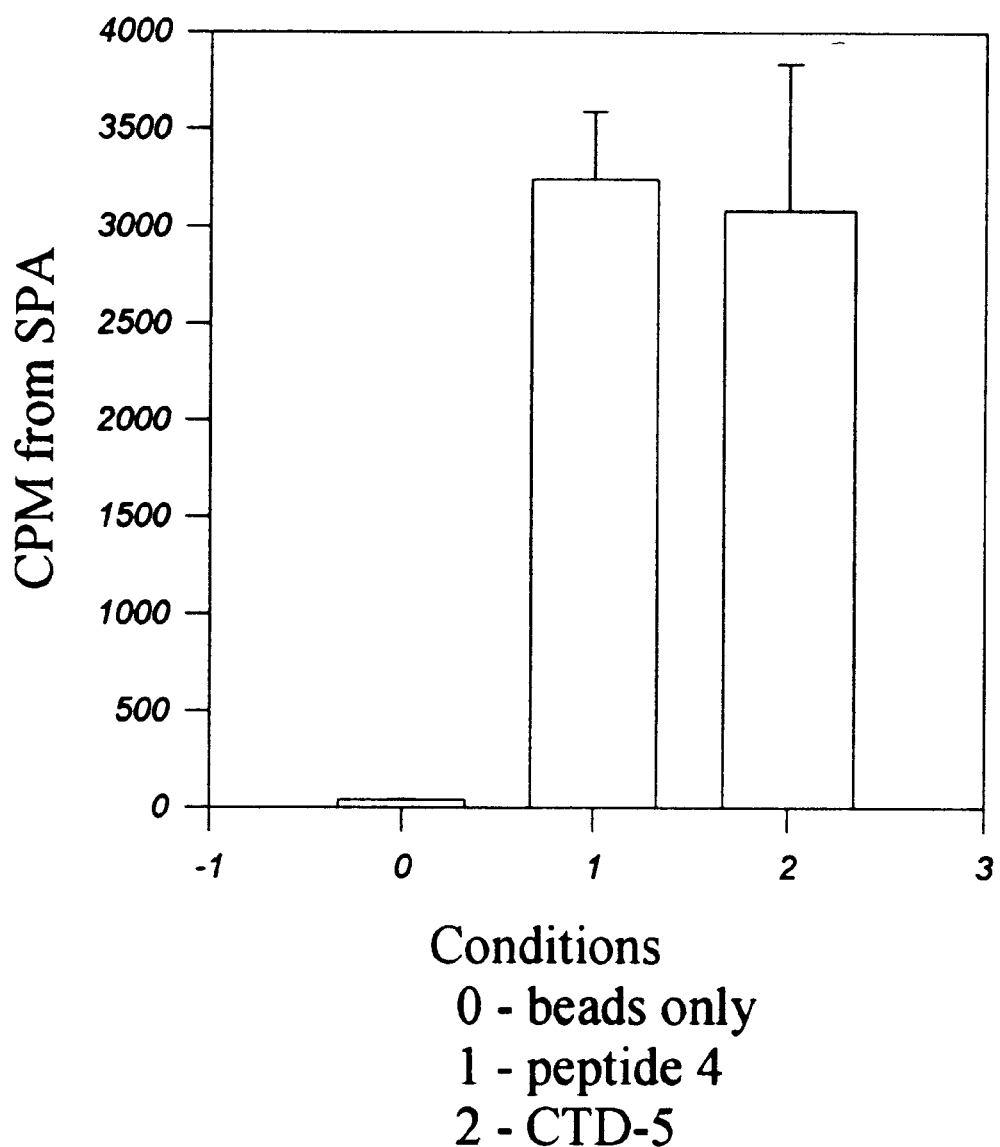

A membrane proximal region of $\beta_c$ including amino acids 458 to 517 has been shown to be essential in the binding of the receptor to JAK2, specifically, two prolines (PXP) and two hydrophobic residues at −1 and −5 relative to the first proline (Rao, 1995, Zhao, 1995). This includes a region known as Box 1 which contains amino acids that are conserved between receptors that bind JAK2 (Tanner, 1995, Jiang, 1996). Peptide 4 [SEQ ID NO:14] binds better than peptide 3 [SEQ ID NO:13] in the SPA. This indicates that amino acids 451 to 457 (amino acids N-terminal of the Box 1 region described in the literature) may contribute to binding JAK2. To determine which amino acids at the C-terminus of peptide 4 [SEQ ID NO:14] are essential for binding, three peptides were designed as shown in table 1 that have increasing deletions of amino acids from the carboxy terminus of peptide 4 [SEQ ID NO:14]. In CTD-3 [SEQ ID NO:17], the second conserved proline of Box 1 (Tanner, 1995) is intact along with three additional amino acids on the C-terminal side of it. In CTD-4 [SEQ ID NO:18], that conserved proline is deleted. In peptide CTD-5 [SEQ ID NO:19], both conserved prolines have been deleted. The results of SPAs using these peptides are shown in FIG. 21. There appeared to be a slight decrease in the activity of CTD-4 [SEQ ID NO:18], however, CTD-5 [SEQ ID NO:19] was as active as peptide 4 [SEQ ID NO:14]. This suggests that the conserved prolines are not necessary for JAK2 binding in vitro, although they may play a role in signal transduction in vivo. Other deletions or mutations may help to further define the binding site in $\beta_c$.

3. ELISA Results

Figure 24:
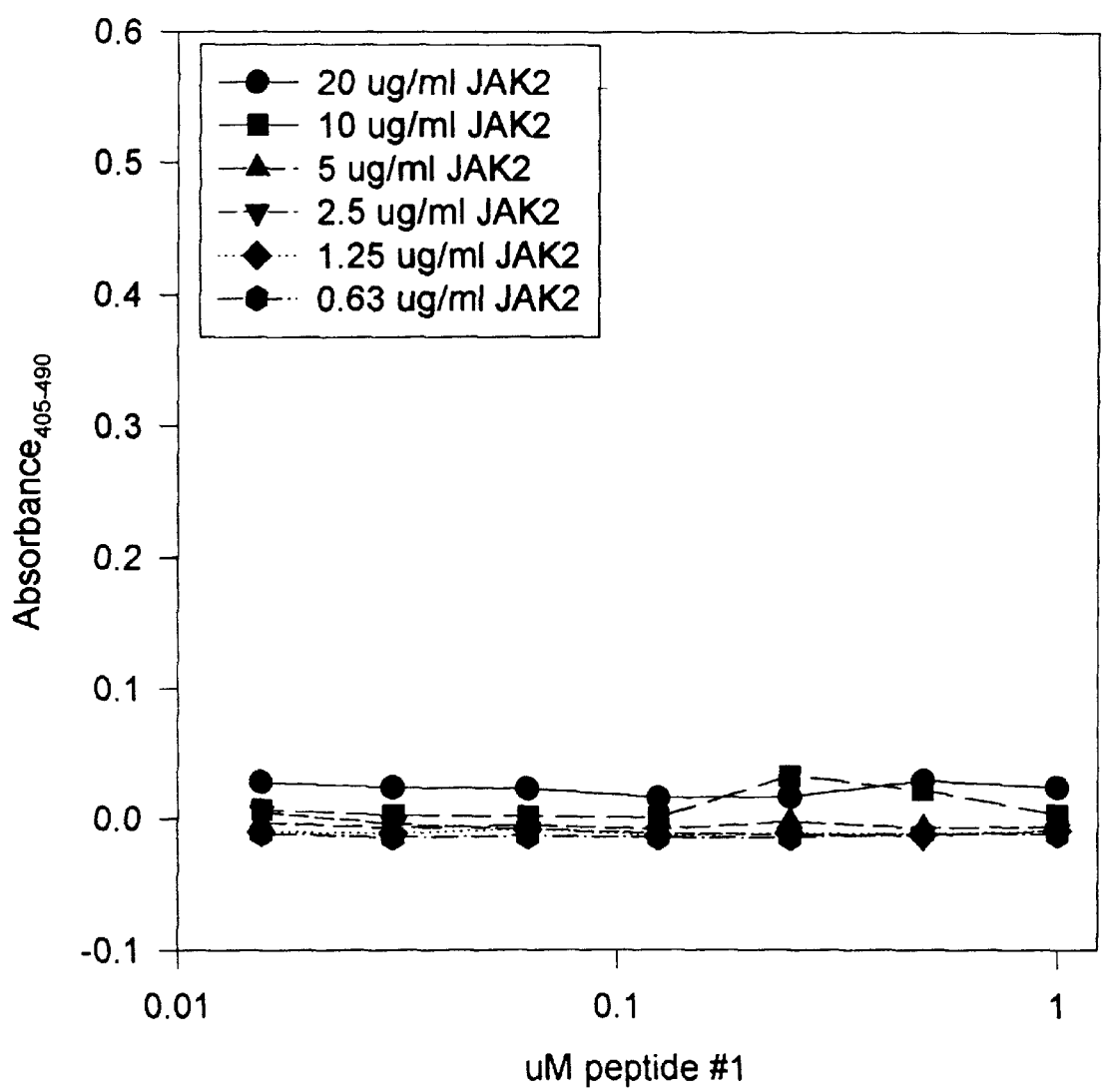
FIGS. 24 A–F illustrates the ELISA binding of JAK2 to immobilized $\beta_c$ peptides. Various concentrations of JAK2 bound to peptides immobilized on streptavidin coated 96-well plates showed different degrees of binding.
Figure 24:
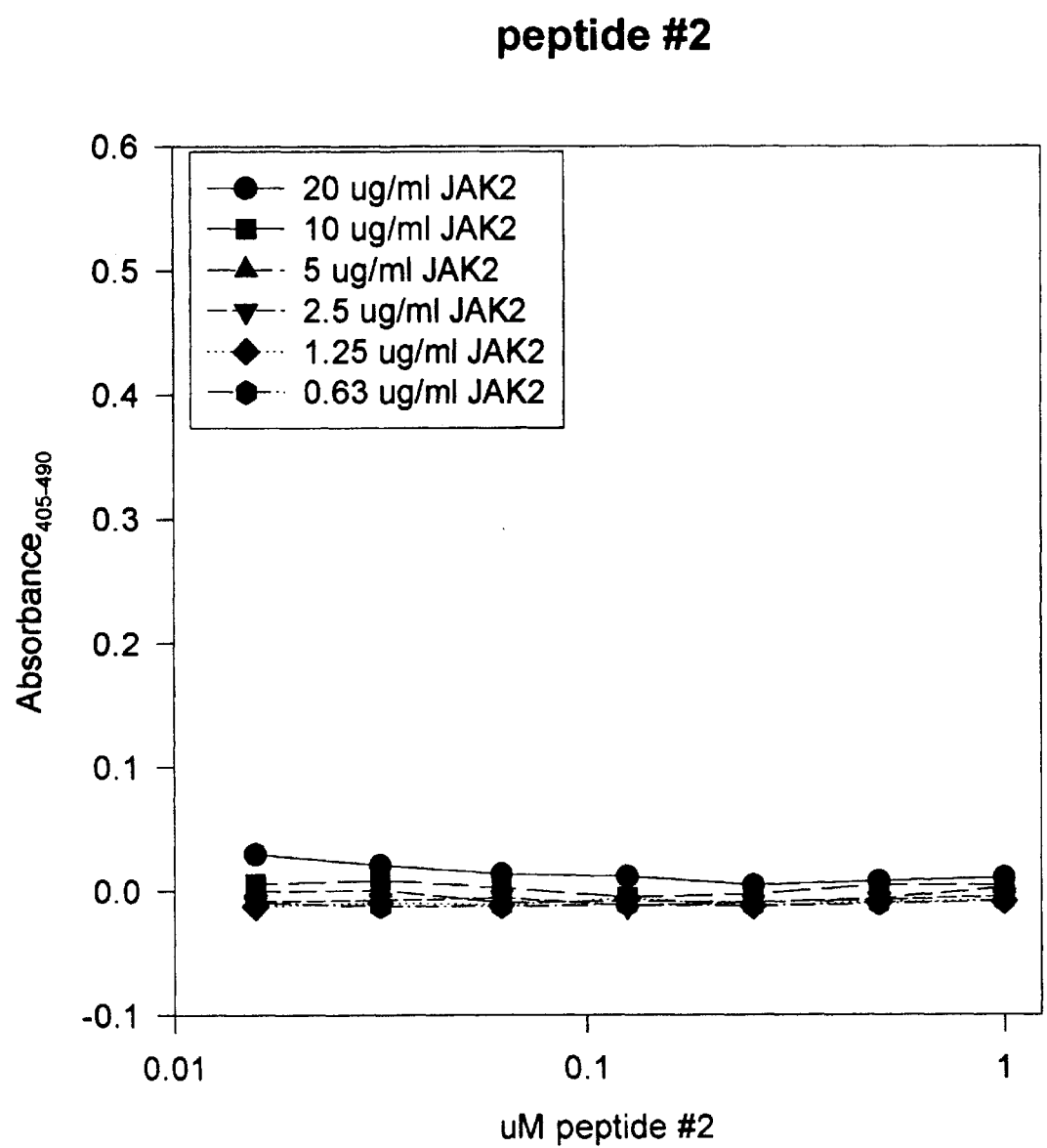
Figure 24:
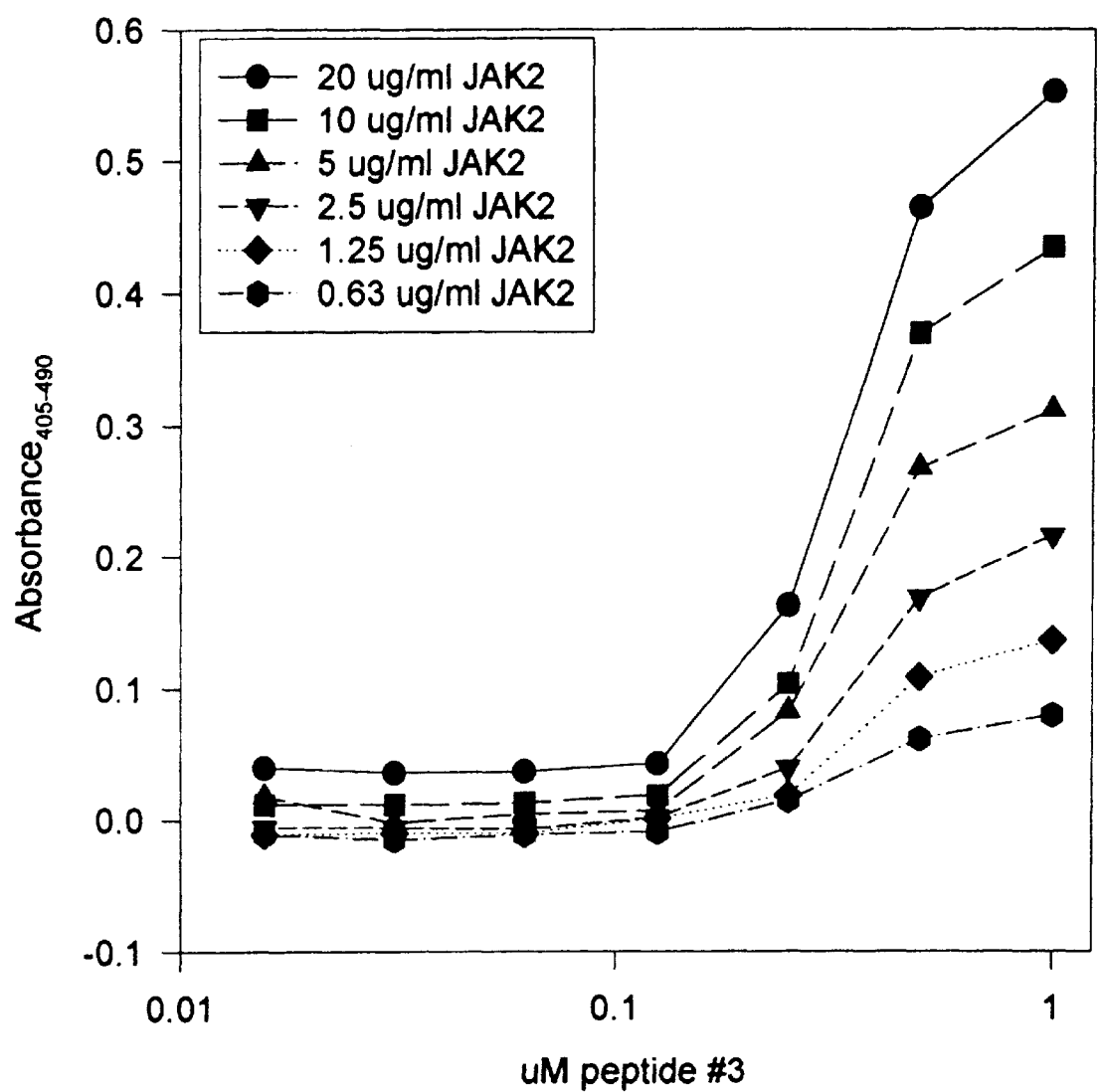
Figure 24:
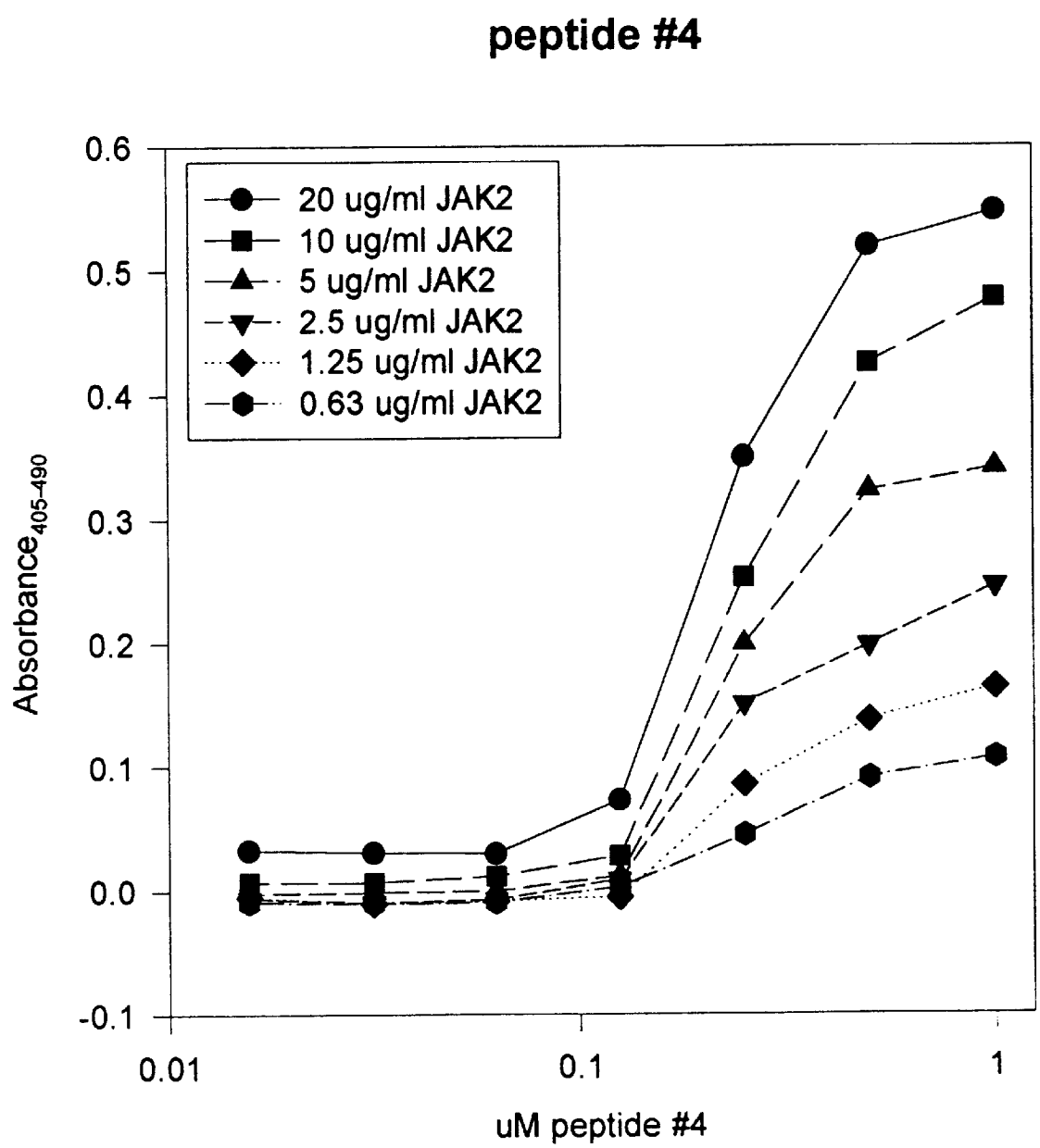
Figure 24:
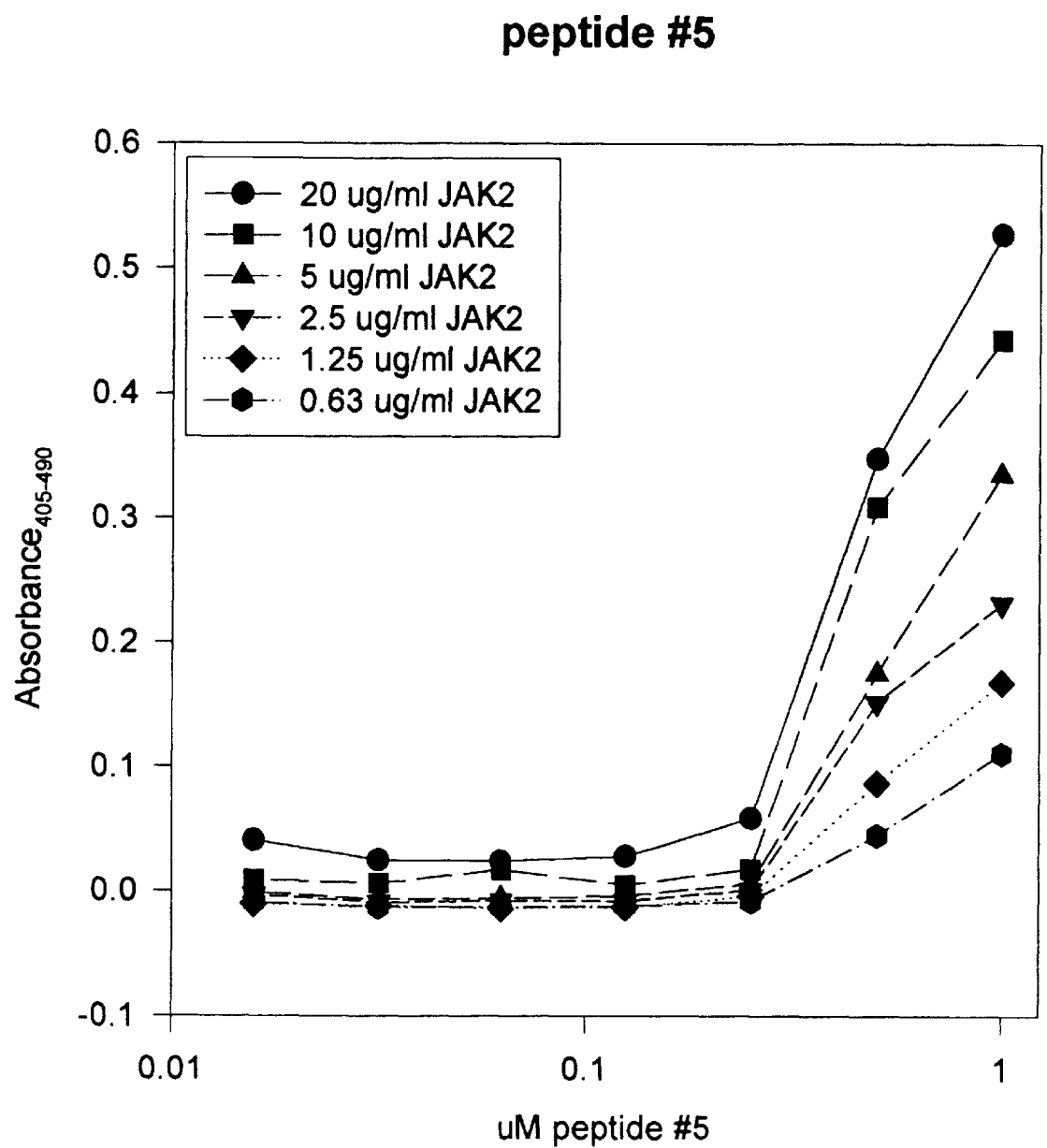
Figure 24:
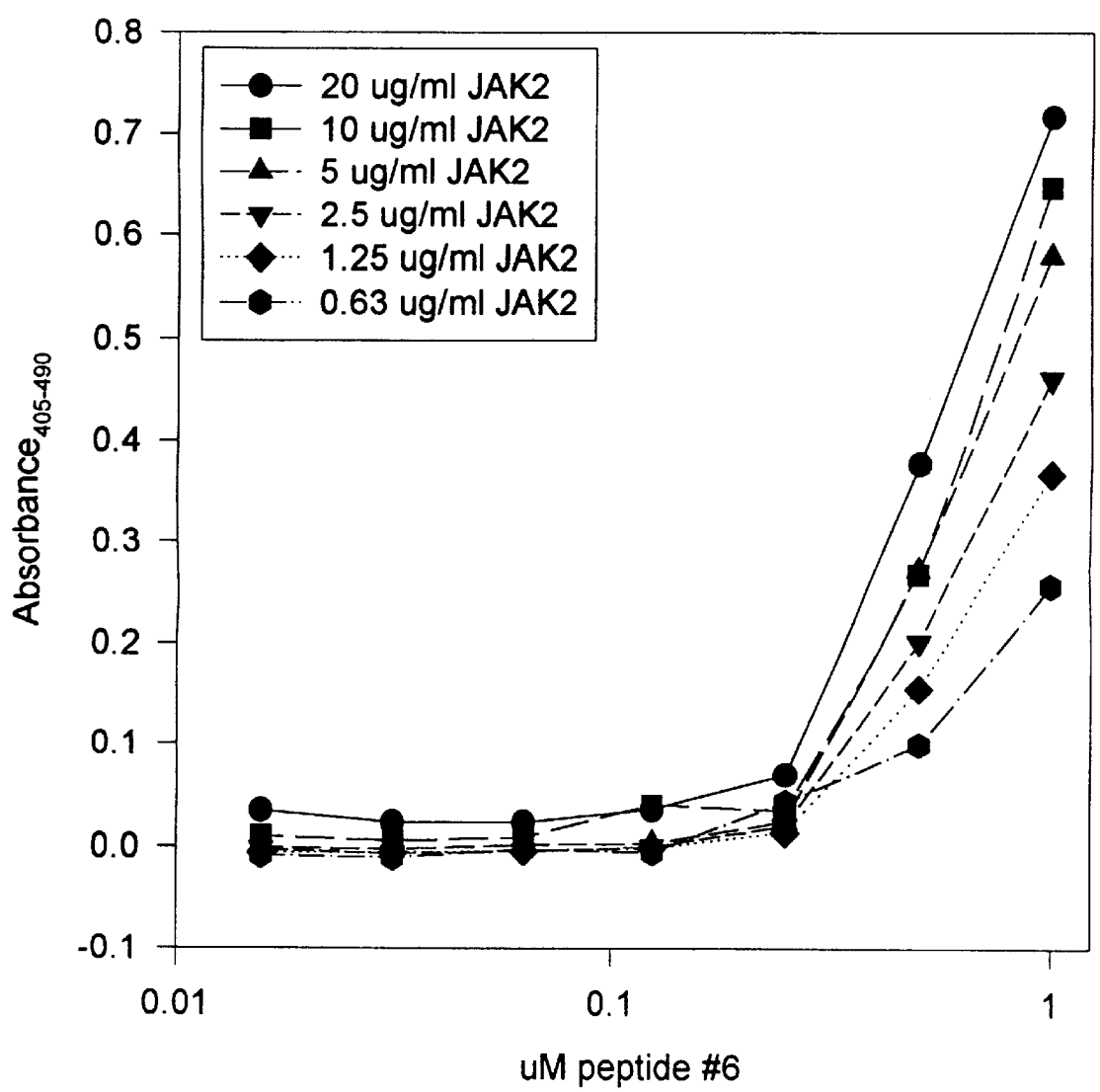

The ELISA assay worked best when the biotinylated $\beta_c$ peptides were immobilized on a streptavidin 96-well plate and the JAK2 was allowed to bind. A dual titration of $\beta_c$ peptides vs. JAK2 was performed (FIG. 24). Peptide 1 [SEQ ID NO:11] (FIG. 24 A) and peptide 2 [SEQ ID NO:12] (FIG. 24 B) gave no binding activity whereas peptides 3–6 [SEQ ID NOS:13–16] (FIGS. 24 C–F) captured JAK2 in the plate. Because 0.4 $\mu$M peptide was calculated to saturate the number of biotin binding sites in each well, it was expected that the amount of JAK2 binding should saturate at this quantity of peptide. This was seen with peptides 3 and 4 [SEQ ID NOS:13 and 14] (FIGS. 24 C and D) but peptides 5 and 6 [SEQ ID NOS:15 and 16] (FIGS. 24 E and F) did not show saturation. Thus, peptides 3 and 4 [SEQ ID NOS:13 and 14] appear optimal for use in the ELISA. Noteably, these peptides were also the two most optimal in the SPA.

In any assay, all or part of human JAK2 containing at least the N-terminal 294 amino acids is expressed in a host cell such as *E. coli*, insect cells (e.g., Sf21), or mammalian cells (e.g., Chinese hamster ovary cells) and then purified. For a scintillation proximity assay (such as taught in U.S. Pat. No. 4,568,649), the protein is labeled with a radioisotope such as $^{125}$I or $^3$H. Then an affinity tag, such as biotin, is bound to a portion of the $\beta_c$ subunit containing the JAK2-binding domain, such as any of the GST fusion proteins described in Example 7 or peptides described in Example 8. Binding is detected by incubating the biotinylated $\beta_c$ subunit with radiolabeled JAK2 in the presence of scintillant-containing beads coated with streptavidin and quantifying the amount of scintillation in an appropriate detector. Non-specific binding is quantified by substituting GST for GST-$\beta_c$ fusion protein in the assay. The ability of compounds to disrupt JAK2/$\beta_c$ binding can be quantified by performing the assay in the presence and absence of various compounds and measuring changes in scintillation. Alternatively, the JAK2 protein can be biotinylated and the $\beta_c$ protein can be radiolabeled in the running of this assay.

A similar assay that makes use of differences in sizes of two proteins is a fluorescence polarization assay. In this case, the smaller of the two proteins (e.g., 13 amino acids of $\beta_c$) is labeled with a fluorescent molecule and incubated with a much larger protein (e.g., 294 or more amino acids of JAK2). Binding of the larger protein to the smaller protein changes the rate of rotation of the latter and therefore changes the polarization of light emitted from the fluorescent tag following excitation with the appropriate wavelength. This change in polarization can be measured in an appropriate detector. The ability of compounds to disrupt JAK2/$\beta_c$ binding can be quantified by performing the assay in the presence and absence of various compounds and measuring changes in fluorescence polarization.

Throughout this disclosure, restriction and DNA-modifying enzymes were from GibcoBRL, Gaithersburg, Md., and all other reagents were from Sigma, St. Louis, Mo., unless otherwise indicated.

REFERENCES

1. National Heart, Lung, and Blood Institute. Guidelines for the diagnosis and management of asthma. National Asthma Education Program Expert Panel Report. *Pediatric Asthma, Allergy, and Immunology* 1991;5:57
2. Howarth P. "The airway inflammatory response in allergic asthma and its relationship to clinical disease." *Allergy* 1995;50 (suppl. 22):13–21.
3. Teixeira M M, Williams T J, Hellewell P G. "Mechanisms and pharmacological manipulation of eosinophil accumulation in vivo." *Trends Pharmacol Sci* 1995;16:418–23.
4. Bousquet J, Chanez P, Lacoste J Y, Barneon G, Ghavanian N, Enander I, et al. "Eosinophilic inflammation in asthma." *N Engl J Med* 1990;323:1033–9.
5. Seminario M-C, Gleich G J. "The role of eosinophils in the pathogenesis of asthma." *Curr Opinion Immunol* 1994;6:860–4.
6. Robinson D S, Ying S, Bentley A M, Meng Q, North J, Durham S R, et al. "Relationships among numbers of bronchoalveolar lavage cells expressing messenger ribonucleic acid for cytokines, asthma symptoms, and airway methacholine responsiveness in atopic asthma." *J Allergy Clin Immunol* 1993;92:397–403.
7. Wallaert B, Desreumaux P, Copin M C, Tillie I, Benard A, Colombel J F, et al. "Immunoreactivity for interleukin 3 and 5 and granulocyte/macrophage colony-stimulating factor of intestinal mucosa in bronchial asthma." *J Exp Med* 1995;182:1897–904.
8. Hoshi H, Ohno I, Honma M, Tanno Y, Yamauchi K, Tamura G, et al. "IL-5, IL-8 and GM-CSF immunostaining of sputum cells in bronchial asthma and chronic bronchitis." *Clin Exp Allergy* 1995;25:720–8.
9. Sakamoto K M, Mignacca R C, Gasson J C. "Signal transduction by granulocyte-macrophage colony-stimulating factor and interleukin-3 receptors." *Receptors Channels* 1994;2:175–81.
10. Yamaguchi Y, Hayashi Y, Sugama Y, Miura Y, Kasahara T, Kitamura S, et al. "Highly purified murine interleukin 5 (IL-5) stimulates eosinophil function and 30 prolongs in vitro survival." *J Exp Med* 1988;167:1737–42.
11. Yamaguchi Y, Suda T, Ohta S, Tominaga K, Miura Y, Kasahara T. "Analysis of the survival of mature human eosinophils: interleukin-5 prevents apoptosis in mature human eosinophils." *Blood* 1991;78:2542–7.
12. Sehmi R, Wardlaw A J, Cromwell O, Kurihara K, Waltmann P, Kay A B. "Interleukin-5 selectively enhances the chemotactic response of eosinophils obtained from normal but not eosinophilic subjects." *Blood* 1992;79:2952–9.

13. Tomioka K, MacGlashan D W, Jr., Lichtenstein L M, Bochner B S, Schleimer R P. "GM-CSF regulates human eosinophil responses to F-Met peptide and platelet activating factor." *J Immunol* 1993; 151:4989–97.
14. Collins P D, Marleau S, Griffiths-Johnson D A, Jose P J, Williams T J. "Cooperation between interleukin-5 and the chemokine eotaxin to induce eosinophil accumulation in vivo." *J Exp Med* 1995;182:1169–74.
15. Griffiths-Johnson D A, Collins P D, Rossi A G, Jose P J, Williams T J. "The chemokine, eotaxin, activates guinieapig eosinophils in vitro and causes their accumulation into the lung in vivo." *Biochem Biophys Res Comm* 1993;197 (3):1167–72.
16. Mauser P J, Pitman A, Witt A, Fernandez X, Zurcher J, Kung T, et al. "Inhibitory effect of the TRFK-5 anti-IL-5 antibody in a guinea pig model of asthma." *Am Rev Respir Dis* 1993;148:1623–7.
17. Kung T T, Stelts D M, Zurcher J A, Adams G K, III, Egan R W, Kreutner W, et al. "Involvement of IL-5 in a murine model of allergic pulmonary inflammation: prophylactic and therapeutic effect of an anti-IL-5 antibody." *Am J Respir Cell Mol Biol* 1995;13:360–5.
18. Mauser P J, Pitman A M, Fernandez X, Foran S K, Adams G K, III, Kreutner W, et al. "Effects of an antibody to interleukin-5 in a monkey model of asthma." *Am J Respir Crit Care Med* 1995;152:467–72.
19. Devos R, Plaetinck G, Cornelis S, Guisez Y, Van der Heyden J, Tavernier J. "Interleukin-5 and its receptor: a drug target for eosinophilia associated with chronic allergic disease." *J Leukoc Biol* 1995;57:813–9.
20. Miyajima A, Mui A L-F, Ogorochi T, Sakamaki K. "Receptors for granulocyte-macrophage colony-stimulating factor, interleukin-3, and interleukin-5." *Blood* 1993;82:1960–74.
21. Pazdrak K, Stafford S, Alam R. "The activation of the JAK-STAT1 signaling pathway by IL-5 in eosinophils." *J Immunol* 1995;155:397–402.
22. Bates M E, Bertics P J, Busse W W. "IL-5 activates a 45-kilodalton mitogen-activated protein (MAP) kinase and JAK-2 tyrosine kinase in human eosinophils." *J Immunol* 1996;156:711–8.
23. Silvennoinen O, Witthuhn B A, Quelle F W, Cleveland J L, Yi T, Ihle J N. "Structure of the murine JAK2 protein-tyrosine kinase and its role in interleukin 3 signal transduction." *Proc Natl Acad Sci USA* 1993;90:8429–33.
24. Sato N, Sakamaki K, Terada N, Arai K, Miyajima A. "Signal transduction by the high-affinity GM-CSF receptor: two distinct cytoplasmic regions of the common b subunit responsible for different signaling." *EMBO J* 1993;12:4181–9.
25. Brizzi M F, Zini M G, Aronica M G, Blechman J M, Yarden Y, Pegoraro L. "Convergence of signaling by interleukin-3, granulocyte-macrophage colony-stimulating factor, and mast cell growth factor on JAK2 tyrosine kinase." *J Biol Chem* 1994;269:31680–4.
26. Hayashida K, Kitamura T, Gorman D M, Arai K-I, Yokota T, Miyajima A. "Molecular cloning of a second subunit of the receptor for human granulocyte-macrophage colony-stimulating factor (GM-CSF): reconstitution of a high-affinity GM-CSF receptor." *Proc Natl Acad Sci USA* 1990;87:9655–9.
27. Quelle F W, Sato N, Witthuhn B A, Inhorn R C, Eder M, Miyajima A, et al. "JAK2 associates with the bc chain of the receptor for granulocyte-macrophage colony-stimulating factor, and its activation requires the membrane-proximal region." *Mol Cell Biol* 1994;14:4335–41.
28. Ihle J N. "Cytokine receptor signalling." *Nature* 1995;377:591–4.
29. Duhé R J, Farrar W L. "Characterization of active and inactive forms of the JAK2 protein-tyrosine kinase produced via the baculovirus expression vector system." *J Biol Chem* 1995;270:23084–9.
30. Ihle J N, Witthuhn B A, Quelle F W, Yamamoto K, Thierfelder W E, Kreider B, et al. "Signaling by the cytokine receptor superfamily: JAKs and STATs." *Trends Biochem Sci* 1994;19:222–7.
31. Ihle J N. "STATs: signal transducers and activators of transcription." *Cell* 1996;84:331–4.
32. Caldenhoven E, van Dijk T, Raaijmakers J A M, Lammers J-W J, Koenderman L, de Groot R P. "Activation of the STAT3/Acute phase response factor transcription factor by interleukin-5." *J Biol Chem* 1995;270:25778–84.
33. Mui A L-F, Wakao H, Harada N, O'Farrell A-M, Miyajima A. "Interleukin-3, granulocyte-macrophage colony-stimulating factor, and interleukin-5 transduce signals through two forms of STAT5." *J Leukoc Biol* 1995;57:799–803.
34. Sakamaki K, Miyajima I, Kitamura T, Miyajima A. "Critical cytoplasmic domains of the common b subunit of the human GM-CSF, IL-3 and IL-5 receptors for growth signal transduction and tyrosine phosphorylation." *EMBO J* 1992;11:3541–9.
35. Möröy T, Grzeschiczek A, Petzold S, Hartmann K-U. "Expression of a Pim-1 transgene accelerates lymphoproliferation and inhibits apoptosis in lpr/lpr mice." *Proc Natl Acad Sci USA* 1993;90:10734–8.
36. Sakamaki K, Yonehara S. "Serum alleviates the requirement of the granulocyte-macrophage colony-stimulating factor (GM-CSF)-induced Ras activation for proliferation of BaF3 cells." *FEBS Lett* 1994;353:133–7.
37. Tanner J W, Chen W, Young R L, Longmore G D, Shaw A S. "The conserved Box 1 motif of cytokine receptors is required for association with JAK kinases." *J Biol Chem* 1995;270:6523–30.
38. Zhuang H, Patel S V, He T-C, Sonsteby S K, Niu Z, Wojchowski. D M. "Inhibition of erythropoietin-induced mitogenesis by a kinase-deficient form of JAK2." *J Biol Chem* 1994;269:21411–4.
39. Frank S J, Yi W, Zhao Y, Goldsmith J F, Gilliland G, Jiang J, et al. "Regions of the JAK2 tyrosine kinase required for coupling to the growth hormone receptor." *J Biol Chem* 1995;270:14776–85.
40. Zhao Y, Wagner F, Frank S J, Kraft A S. "The amino-terminal portion of the JAK2 protein kinase is necessary for binding and phosphorylation of the granulocyte-macrophage colony-stimulating factor receptor bc chain". *J Biol Chem* 1995;270:13814–8.
41. Harpur A G, Andres A-C, Ziemiecki A, Aston R R, Wilks A F. "JAK2, a third member of the JAK family of protein tyrosine kinases." *Oncogene* 1992;7:1347–53.
42. Zhuang H, Niu Z, He T-C, Patel S V, Wojchowski D M. "Erythropoietin-dependent inhibition of apoptosis is supported by carboxyl-truncated receptor forms and blocked by dominant-negative forms of JAK2." *J Biol Chem* 1995;270:14500–4.
44. Laemmli U K. "Cleavage of structural proteins during the assembly of the head of bacteriophage T4." *Nature* 1970;227:680–5.
45. Towbin H, Staehelin T, Bordon J. "Electrophoretic transfer of proteins from polyacrylamide gels to nitrocellulose sheets: procedure and some applications." *Proc Natl Acad Sci* 1979;76:4350–4.
46. Kitamura T, Tange T, Terasawa T, Chiba S, Kuwaki T, Miyagawa K, et al. "Establishment and characterization of a unique human cell line that proliferates dependently on GM-CSF, IL-3, or erythropoietin." *J Cell Phys* 1989;140:323–34.
47. Vinella D, D'Ari R. "Thermoinducible filamentation in *Escherichia coli* due to an altered RNA polymerase beta subunit is suppressed by high levels of ppGpp." *J Bacteriol* 1994;176:966–72.
48. Ohlendieck K, Ervasti J M, Snook J B, Campbell K P. "Dystrophin-glycoprotein complex is highly enriched in isolated skeletal muscle sarcolemma." *J Cell Biol* 1991;112:135–48.
49. Duhe R J, Rui H, Greenwood J D, Garvey K & Farrar W L. "Cloning of the gene encoding rat JAK2, a protein tyrosine kinase." *Gene* 158: 281–286 (1995).
50. Altschul, S F, Gish W, Miller W, Myers E W, Lipman D J. "Basic local alignment search tool. *J Mol Biol* 215:403–410 (1990).
51. O'Reilly D R, Miller L K, Luckow V A. "Baculovirus expression vectors: a laboratory manual." New York: W. H. Freeman and Company, 1992.
52. Kummer U, Thiel E. Doxiadis I, Eulitz M, Sladoljev S, Thierfelder S. "Tritium radiolabeling of antibodies to high specific activity with N-succinimidyl[2,3-$^3$]propionate: use in detecting monoclonal antibodies. *J Imm Methods* 42:367–374, 1981.
53. Barany G. Merrifield R B in The Peptides. Gross E. Meinhofer J. editors, Vol 2, 1979, pp. 1–284.
54. Peeters P, Raynaud S D, Cools J, Wlodarska I. Grosgeorge J, Philip P, Monpoux F, Van Rompaey L, Baens M, Van den Berghe H and Marynen P. "Fusion of TEL, the ETS-varian gene 6 (ETV6), to the receptor-associated kinase JAK2 as a result of t(9;12) in a lymphoid and t(9;15;12) in a myeloid leukemia." *Blood* 90:2535–2540, 1997.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
        (A) LENGTH: 1302 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
ATCTACGGGT ACAGGCTGCG CAGAAAGTGG GAGGAGAAGA TCCCCAACCC CAGCAAGAGC      60

CACCTGTTCC AGAACGGGAG CGCAGAGCTT TGGCCCCCAG GCAGCATGTC GGCCTTCACT     120

AGCGGGAGTC CCCCACACCA GGGGCCGTGG GGCAGCCGCT TCCCTGAGCT GGAGGGGGTG     180

TTCCCTGTAG GATTCGGGGA CAGCGAGGTG TCACCTCTCA CCATAGAGGA CCCCAAGCAT     240

GTCTGTGATC CACCATCTGG GCCTGACACG ACTCCAGCTG CCTCAGATCT ACCCACAGAG     300

CAGCCCCCCA GCCCCCAGCC AGGCCCGCCT GCCGCCTCCC ACACACCTGA GAAACAGGCT     360

TCCAGCTTTG ACTTCAATGG GCCCTACCTG GGGCCGCCCC ACAGCCGCTC CCTACCTGAC     420

ATCCTGGGCC AGCGGGAGCC CCCACAGGAG GGTGGGAGCC AGAAGTCCCC ACCTCCAGGG     480

TCCCTGGAGT ACCTGTGTCT GCCTGCTGGG GGGCAGGTGC AACTGGTCCC TCTGGCCCAG     540

GCGATGGGAC CGGGACAGGC CGTGGAAGTG GAGAGAAGGC CGAGCCAGGG GGCTGCAGGG     600

AGTCCCTCCC TGGAGTCCGG GGGAGGCCCT GCCCCTCCTG CTCTTGGGCC AAGGGTGGGA     660

GGACAGGACC AAAAGGACAG CCCTGTGGCT ATACCCATGA GCTCTGGGGA CACTGAGGAC     720

CCTGGAGTGG CCTCTGGTTA TGTCTCCTCT GCAGACCTGG TATTCACCCC AAACTCAGGG     780

GCCTCGTCTG TCTCCCTAGT TCCCTCTCTG GGCCTCCCCT CAGACCAGAC CCCCAGCTTA     840

TGTCCTGGGC TGGCCAGTGG ACCCCCTGGA GCCCCAGGCC CTGTGAAGTC AGGGTTTGAG     900
```

```
GGCTATGTGG AGCTCCCTCC AATTGAGGGC CGGTCCCCCA GGTCACCAAG GAACAATCCT    960

GTCCCCCCTG AGGCCAAAAG CCCTGTCCTG AACCCAGGGG AACGCCCGGC AGATGTGTCC   1020

CCAACATCCC CACAGCCCGA GGGCCTCCTT GTCCTGCAGC AAGTGGGCGA CTATTGCTTC   1080

CTCCCCGGCC TGGGGCCCGG CCCTCTCTCG CTCCGGAGTA AACCTTCTTC CCCGGGACCC   1140

GGTCCTGAGA TCAAGAACCT AGACCAGGCT TTTCAAGTCA AGAAGCCCCC AGGCCAGGCT   1200

GTGCCCCAGG TGCCCGTCAT TCAGCTCTTC AAAGCCCTGA AGCAGCAGGA CTACCTGTCT   1260

CTGCCCCCTT GGGAGGTCAA CAAGCCTGGG GAGGTGTGTT GA                      1302

(2) INFORMATION FOR SEQ ID NO:2:

(i) SEQUENCE CHARACTERISTICS:
        (A) LENGTH: 433 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ile Tyr Gly Tyr Arg Leu Arg Arg Lys Trp Glu Glu Lys Ile Pro Asn
1               5                   10                  15

Pro Ser Lys Ser His Leu Phe Gln Asn Gly Ser Ala Glu Leu Trp Pro
            20                  25                  30

Pro Gly Ser Met Ser Ala Phe Thr Ser Gly Ser Pro His Gln Gly
        35                  40                  45

Pro Trp Gly Ser Arg Phe Pro Glu Leu Glu Gly Val Phe Pro Val Gly
    50                  55                  60

Phe Gly Asp Ser Glu Val Ser Pro Leu Thr Ile Glu Asp Pro Lys His
65                  70                  75                  80

Val Cys Asp Pro Pro Ser Gly Pro Asp Thr Thr Pro Ala Ala Ser Asp
                85                  90                  95

Leu Pro Thr Glu Gln Pro Pro Ser Pro Gln Pro Gly Pro Pro Ala Ala
            100                 105                 110

Ser His Thr Pro Glu Lys Gln Ala Ser Ser Phe Asp Phe Asn Gly Pro
        115                 120                 125

Tyr Leu Gly Pro Pro His Ser Arg Ser Leu Pro Asp Ile Leu Gly Gln
    130                 135                 140

Pro Glu Pro Pro Gln Glu Gly Gly Ser Gln Lys Ser Pro Pro Pro Gly
145                 150                 155                 160

Ser Leu Glu Tyr Leu Cys Leu Pro Ala Gly Gly Gln Val Gln Leu Val
                165                 170                 175

Pro Leu Ala Gln Ala Met Gly Pro Gly Gln Ala Val Glu Val Glu Arg
            180                 185                 190

Arg Pro Ser Gln Gly Ala Ala Gly Ser Pro Ser Leu Glu Ser Gly Gly
        195                 200                 205

Gly Pro Ala Pro Pro Ala Leu Gly Pro Arg Val Gly Gly Gln Asp Gln
    210                 215                 220

Lys Asp Ser Pro Val Ala Ile Pro Met Ser Ser Gly Asp Thr Glu Asp
225                 230                 235                 240

Pro Gly Val Ala Ser Gly Tyr Val Ser Ser Ala Asp Leu Val Phe Thr
                245                 250                 255

Pro Asn Ser Gly Ala Ser Ser Val Ser Leu Val Pro Ser Leu Gly Leu
            260                 265                 270
```

```
Pro Ser Asp Gln Thr Pro Ser Leu Cys Pro Gly Leu Ala Ser Gly Pro
            275                 280                 285

Pro Gly Ala Pro Gly Pro Val Lys Ser Gly Phe Glu Gly Tyr Val Glu
            290                 295                 300

Leu Pro Pro Ile Glu Gly Arg Ser Pro Arg Ser Pro Arg Asn Asn Pro
305                 310                 315                 320

Val Pro Pro Glu Ala Lys Ser Pro Val Leu Asn Pro Gly Glu Arg Pro
            325                 330                 335

Ala Asp Val Ser Pro Thr Ser Pro Gln Pro Glu Gly Leu Leu Val Leu
            340                 345                 350

Gln Gln Val Gly Asp Tyr Cys Phe Leu Pro Gly Leu Gly Pro Gly Pro
            355                 360                 365

Leu Ser Leu Arg Ser Lys Pro Ser Ser Pro Gly Pro Gly Pro Glu Ile
            370                 375                 380

Lys Asn Leu Asp Gln Ala Phe Gln Val Lys Lys Pro Pro Gly Gln Ala
385                 390                 395                 400

Val Pro Gln Val Pro Val Ile Gln Leu Phe Lys Ala Leu Lys Gln Gln
            405                 410                 415

Asp Tyr Leu Ser Leu Pro Pro Trp Glu Val Asn Lys Pro Gly Glu Val
            420                 425                 430

Cys
```

(2) INFORMATION FOR SEQ ID NO:3:

(i) SEQUENCE CHARACTERISTICS:
        (A) LENGTH: 62 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg Lys Trp Glu Glu Lys Ile Pro Asn Pro Ser Lys Ser His Leu Phe
1               5                   10                  15

Gln Asn Gly Ser Ala Glu Leu Trp Pro Pro Gly Ser Met Ser Ala Phe
            20                  25                  30

Thr Ser Gly Ser Pro Pro His Gln Gly Pro Trp Gly Ser Arg Phe Pro
            35                  40                  45

Glu Leu Glu Gly Val Phe Pro Val Gly Phe Gly Asp Ser Glu
            50                  55                  60
```

(2) INFORMATION FOR SEQ ID NO:4:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

```
ATGGGAATGG CCTGCCTTAC AATGACAGAA ATGGAGGGAA CATCCACCTC TTCTATATAT    60

CAGAATGGTG ATATTTCTGG AAATGCCAAT TCTATGAAGC AAATAGATCC AGTTCTTCAG   120

GTGTATCTTT ACCATTCCCT TGGGAAATCT GAGGCAGATT ATCTGACCTT TCCATCTGGG   180

GAGTATGTTG CAGAAGAAAT CTGTATTGCT GCTTCTAAAG CTTGTGGTAT CACACCTGTG   240

TATCATAATA TGTTTGCTTT AATGAGTGAA ACAGAAAGGA TCTGGTATCC ACCCAACCAT   300
```

-continued

```
GTCTTCCATA TAGATGAGTC AACCAGGCAT AATGTACTCT ACAGAATAAG ATTTTACTTT      360

CCTCGTTGGT ATTGCAGTGG CAGCAACAGA GCCTATCGGC ATGGAATATC TCGAGGTGCT      420

GAAGCTCCTC TTCTTGATGA CTTTGTCATG TCTTACCTCT TTGCTCAGTG GCGGCATGAT      480

TTTGTGCACG GATGGATAAA AGTACCTGTG ACTCATGAAA CACAGGAAGA ATGTCTTGGG      540

ATGGCAGTGT TAGATATGAT GAGAATAGCC AAAGAAAACG ATCAAACCCC ACTGGCCATC      600

TATAACTCTA TCAGCTACAA GACATTCTTA CCAAAATGTA TTCGAGCAAA GATCCAAGAC      660

TATCATATTT TGACAAGGAA GCGAATAAGG TACAGATTTC GCAGATTTAT TCAGCAATTC      720

AGCCAATGCA AAGCCACTGC CAGAAACTTG AAACTTAAGT ATCTTATAAA TCTGGAAACT      780

CTGCAGTCTG CCTTCTACAC AGAGAAATTT GAAGTAAAAG AACCTGGAGG TGGTCCTTCA      840

GGTGAGGAGA TTTTTGCAAC CATTATAATA ACTGGAAACG GT                        882
```

(2) INFORMATION FOR SEQ ID NO:5:

(i) SEQUENCE CHARACTERISTICS:
        (A) LENGTH: 294 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Gly Met Ala Cys Leu Thr Met Thr Glu Met Glu Gly Thr Ser Thr
1               5                   10                  15

Ser Ser Ile Tyr Gln Asn Gly Asp Ile Ser Gly Asn Ala Asn Ser Met
            20                  25                  30

Lys Gln Ile Asp Pro Val Leu Gln Val Tyr Leu Tyr His Ser Leu Gly
        35                  40                  45

Lys Ser Glu Ala Asp Tyr Leu Thr Phe Pro Ser Gly Tyr Val Ala
    50                  55                  60

Glu Glu Ile Cys Ile Ala Ala Ser Lys Ala Cys Gly Ile Thr Pro Val
65                  70                  75                  80

Tyr His Asn Met Phe Ala Leu Met Ser Glu Thr Glu Arg Ile Trp Tyr
                85                  90                  95

Pro Pro Asn His Val Phe His Ile Asp Glu Ser Thr Arg His Asn Val
            100                 105                 110

Leu Tyr Arg Ile Arg Phe Tyr Phe Pro Arg Trp Tyr Cys Ser Gly Ser
        115                 120                 125

Asn Arg Ala Tyr Arg His Gly Ile Ser Arg Gly Ala Glu Ala Pro Leu
    130                 135                 140

Leu Asp Asp Phe Val Met Ser Tyr Leu Phe Ala Gln Trp Arg His Asp
145                 150                 155                 160

Phe Val His Gly Trp Ile Lys Val Pro Val Thr His Glu Thr Gln Glu
                165                 170                 175

Glu Cys Leu Gly Met Ala Val Leu Asp Met Met Arg Ile Ala Lys Glu
            180                 185                 190

Asn Asp Gln Thr Pro Leu Ala Ile Tyr Asn Ser Ile Ser Tyr Lys Thr
        195                 200                 205

Phe Leu Pro Lys Cys Ile Arg Ala Lys Ile Gln Asp Tyr His Ile Leu
    210                 215                 220

Thr Arg Lys Arg Ile Arg Tyr Arg Phe Arg Phe Ile Gln Gln Phe
225                 230                 235                 240
```

Ser Gln Cys Lys Ala Thr Ala Arg Asn Leu Lys Leu Lys Tyr Leu Ile
            245                 250                 255

Asn Leu Glu Thr Leu Gln Ser Ala Phe Tyr Thr Glu Lys Phe Glu Val
            260                 265                 270

Lys Glu Pro Gly Gly Gly Pro Ser Gly Glu Glu Ile Phe Ala Thr Ile
            275                 280                 285

Ile Ile Thr Gly Asn Gly
            290

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCGAATTCAT CTACGGGTAC AGGCTG                                      26

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TAGCGGCCGC TCAACACACC TCCCCAGG                                    28

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGGAATTCAT GGGAATGGCC TGCCTTACAA TGACAGAA                      38

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

TAGCGGCCGC ACCGTTTCCA GTTATTATAA TGGTTGCAA                   39

(2) INFORMATION FOR SEQ ID NO:10:

(i) SEQUENCE CHARACTERISTICS:
        (A) LENGTH: 16 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:10:

Arg Arg Lys Trp Glu Glu Lys Ile Pro Asn Pro Ser Lys Ser His Leu
1               5                   10                  15

(2) INFORMATION FOR SEQ ID NO:11:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:11:

Glu Lys Ile Pro Asn Pro Ser Lys Ser His Leu Phe Gln Asn Gly Ser
1               5                   10                  15

Ala Glu Leu Trp Pro
            20

(2) INFORMATION FOR SEQ ID NO:12:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:12:

Arg Lys Trp Glu Glu Lys Ile Pro Asn Pro Ser Lys Ser His Leu Phe
1               5                   10                  15

Gln Asn Gly Ser Ala Glu Leu Trp Pro
            20                  25

(2) INFORMATION FOR SEQ ID NO:13:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:13:

Tyr Arg Leu Arg Arg Lys Trp Glu Glu Lys Ile Pro Asn Pro Ser Lys
1               5                   10                  15

Ser His Leu Phe Gln Asn Gly Ser Ala Glu Leu Trp Pro
            20                  25

(2) INFORMATION FOR SEQ ID NO:14:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:14:

-continued

```
Gly Ile Tyr Gly Tyr Arg Leu Arg Arg Lys Trp Glu Lys Ile Pro
1               5                   10                  15

Asn Pro Ser Lys Ser His Leu Phe Gln Asn Gly Ser Ala Glu Leu Trp
                20                  25                  30

Pro
```

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Phe Cys Gly Ile Tyr Gly Tyr Arg Leu Arg Arg Lys Trp Glu Lys
1               5                   10                  15

Ile Pro Asn Pro Ser Lys Ser His Leu Phe Gln Asn Gly Ser Ala Glu
                20                  25                  30

Leu Trp Pro
        35
```

(2) INFORMATION FOR SEQ ID NO:16:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Leu Ala Leu Arg Phe Cys Gly Ile Tyr Gly Tyr Arg Leu Arg Arg Lys
1               5                   10                  15

Trp Glu Glu Lys Ile Pro Asn Pro Ser Lys Ser His Leu Phe Gln Asn
                20                  25                  30

Gly Ser Ala Glu Leu Trp Pro
        35
```

(2) INFORMATION FOR SEQ ID NO:17:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

```
Gly Ile Tyr Gly Tyr Arg Leu Arg Arg Lys Trp Glu Glu Lys Ile Pro
1               5                   10                  15

Asn Pro Ser Lys Ser
                20
```

(2) INFORMATION FOR SEQ ID NO:18:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Gly Ile Tyr Gly Tyr Arg Leu Arg Arg Lys Trp Glu Glu Lys Ile Pro
1               5                   10                  15

Asn (2) INFORMATION FOR SEQ ID NO:19:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:19:

Gly Ile Tyr Gly Tyr Arg Leu Arg Arg Lys Trp Glu Glu
1               5                   10

(2) INFORMATION FOR SEQ ID NO:20:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (xi) SEQUENCE DESCRIPTION: SEQ ID NO:20:

Asp Tyr Lys Asp Asp Asp Asp Lys
1               5

(2) INFORMATION FOR SEQ ID NO:21:

(i) SEQUENCE CHARACTERISTICS:
            (A) LENGTH: 3435 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:21:

| | | | | | |
|---|---|---|---|---|---|
| CCCGGGGGAA | TGGCCTGCCT | TACGATGACA | GAAATGGAGG | GAACATCCAC | CTCTTCTATA | 60 |
| TATCAGAATG | GTGATATTTC | TGGAAATGCC | AATTCTATGA | AGCAAATAGA | TCCAGTTCTT | 120 |
| CAGGTGTATC | TTTACCATTC | CCTTGGGAAA | TCTGAGGCAG | ATTATCTGAC | CTTTCCATCT | 180 |
| GGGGAGTATG | TTGCAGAAGA | AATCTGTATT | GCTGCTTCTA | AAGCTTGTGG | TATCACACCT | 240 |
| GTGTATCATA | ATATGTTTGC | TTTAATGAGT | GAAACAGAAA | GGATCTGGTA | TCCACCCAAC | 300 |
| CATGTCTTCC | ATATAGATGA | GTCAACCAGG | CATAATGTAC | TCTACAGAAT | AAGATTTTAC | 360 |
| TTTCCTCGTT | GGTATTGCAG | TGGCAGCAAC | AGAGCCTATC | GGCATGGAAT | ATCTCGAGGT | 420 |
| GCTGAAGCTC | CTCTTCTTGA | TGACTTTGTC | ATGTCTTACC | TCTTTGCTCA | GTGGCGGCAT | 480 |
| GATTTTGTGC | ATGGATGGAT | AAAAGTACCT | GTGACTCATG | AAACACAGGA | AGAATGTCTT | 540 |
| GGGATGGCAG | TGTTAGATAT | GATGAGAATA | GCCAAAGAAA | ACGATCAAAC | CCCACTGGCC | 600 |
| ATCTATAACT | CTATCAGCTA | CAAGACATTC | TTACCAAAAT | GTATTCGAGC | AAAGATCCAA | 660 |
| GACTATCATA | TTTTGACAAG | GAAGCGAATA | AGGTACAGAT | TCGCAGATT | TATTCAGCAA | 720 |

```
TTCAGCCAAT GCAAAGCCAC TGCCAGAAAC TTGAAACTTA AGTATCTTAT AAATCTGGAA      780

ACTCTGCAGT CTGCCTTCTA CACAGAGAAA TTTGAAGTAA AGAACCTGG AAGTGGTCCT      840

TCAGGTGAGG AGATTTTTGC AACCATTATA ATAACTGGAA ACGGTGGAAT TCAGTGGTCA      900

AGAGGGAAAC ATAAAGAAAG TGAGACACTG ACAGAACAGG ATTTACAGTT ATATTGCGAT      960

TTTCCTAATA TTATTGATGT CAGTATTAAG CAAGCAAACC AAGAGGGTTC AAATGAAAGC     1020

CGAGTTGTAA CTATCCATAA GCAAGATGGT AAAAATCTGG AAATTGAACT AGCTCATTA     1080

AGGGAAGCTT TGTCTTTCGT GTCATTAATT GATGGATATT ATAGATTAAC TGCAGATGCA     1140

CATCATTACC TCTGTAAAGA AGTAGCACCT CCAGCCGTGC TTGAAAATAT ACAAAGCAAC     1200

TGTCATGGCC CAATTTCGAT GGATTTTGCC ATTAGTAAAC TGAAGAAAGC AGGTAATCAG     1260

ACTGGACTGT ATGTACTTCG ATGCAGTCCT AAGGACTTTA ATAAATATTT TTTGACTTTT     1320

GCTGTCGAGC GAGAAAATGT CATTGAATAT AAACACTGTT TGATTACAAA AAATGAGAAT     1380

GAAGAGTACA ACCTCAGTGG GACAAAGAAG AACTTCAGCA GTCTTAAAGA TCTTTTGAAT     1440

TGTTACCAGA TGGAAACTGT TCGCTCAGAC AATATAATTT TCCAGTTTAC TAAATGCTGT     1500

CCCCCAAAGC CAAAAGATAA ATCAAACCTT CTAGTCTTCA GAACGAATGG TGTTTCTGAT     1560

GTACCAACCT CACCAACATT ACAGAGGCCT ACTCATATGA ACCAAATGGT GTTTCACAAA     1620

ATCAGAAATG AAGATTTGAT ATTTAATGAA AGCCTTGGCC AAGGCACTTT TACAAAGATT     1680

TTTAAAGGCG TACGAAGAGA AGTAGGGAGAC TACGGTCAAC TGCATGAAAC AGAAGTTCTT     1740

TTAAAAGTTC TGGATAAAGC ACACAGAAAC TATTCAGAGT CTTTCTTTGA AGCAGCAAGT     1800

ATGATGAGCA AGCTTTCTCA CAAGCATTTG GTTTTAAATT ATGGAGTATG TGTCTGTGGA     1860

GACGAGAATA TTCTGGTTCA GGAGTTTGTA AAATTTGGAT CACTAGATAC ATATCTGAAA     1920

AAGAATAAAA ATTGTATAAA TATATTATGG AAACTTGAAG TTGCTAAACA GTTGGCATGG     1980

GCCATGCATT TTCTAGAAGA AAACACCCTT ATTCATGGGA ATGTATGTGC CAAAAATATT     2040

CTGCTTATCA GAGAAGAAGA CAGGAAGACA GGAAATCCTC CTTTCATCAA ACTTAGTGAT     2100

CCTGGCATTA GTATTACAGT TTTGCCAAAG GACATTCTTC AGGAGAGAAT ACCATGGGTA     2160

CCACCTGAAT GCATTGAAAA TCCTAAAAAT TTAAATTTGG CAACAGACAA ATGGAGTTTT     2220

GGTACCACTT TGTGGGAAAT CTGCAGTGGA GGAGATAAAC CTCTAAGTGC TCTGGATTCT     2280

CAAAGAAAGC TACAATTTTA TGAAGATAGG CATCAGCTTC CTGCACCAAA GTGGGCAGAA     2340

TTAGCAAACC TTATAAATAA TTGTATGGAT TATGAACCAG ATTTCAGGCC TTCTTTCAGA     2400

GCCATCATAC GAGATCTTAA CAGTTTGTTT ACTCCAGATT ATGAACTATT AACAGAAAAT     2460

GACATGTTAC CAAATATGAG GATAGGTGCC CTAGGGTTTT CTGGTGCCTT TGAAGACCGG     2520

GATCCTACAC AGTTTGAAGA GAGACATTTG AAATTTCTAC AGCAACTTGG CAAGGGTAAT     2580

TTTGGGAGTG TGGAGATGTG CCGGTATGAC CCTCTACAGG ACAACACTGG GGAGGTGGTC     2640

GCTGTAAAAA AGCTTCAGCA TAGTACTGAA GAGCACCTAA GAGACTTTGA AAGGGAAATT     2700

GAAATCCTGA ATCCCTACA GCATGACAAC ATTGTAAAGT ACAAGGGAGT GTGCTACAGT     2760

GCTGGTCGGC GTAATCTAAA ATTAATTATG GAATATTTAC CATATGGAAG TTTACGAGAC     2820

TATCTTCAAA AACATAAAGA ACGGATAGAT CACATAAAAC TTCTGCAGTA CACATCTCAG     2880

ATATGCAAGG GTATGGAGTA TCTTGGTACA AAAAGGTATA TCCACAGGGA TCTGGCAACG     2940

AGAAATATAT TGGTGGAGAA CGAGAACAGA GTTAAAATTG GAGATTTTGG GTTAACCAAA     3000

GTCTTGCCAC AAGACAAAGA ATACTATAAA GTAAAGAAC CTGGTGAAAG TCCCATATTC     3060

TGGTATGCTC CAGAATCACT GACAGAGAGC AAGTTTTCTG TGGCCTCAGA TGTTTGGAGC     3120
```

-continued

```
TTTGGAGTGG TTCTGTATGA ACTTTTCACA TACATTGAGA GAGTAAAAG TCCACCAGCG    3180

GAATTTATGC GTATGATTGG CAATGACAAA CAAGGACAGA TGATCGTGTT CCATTTGATA    3240

GAACTTTTGA AGAATAATGG AAGATTACCA AGACCAGATG GATGCCCAGA TGAGATCTAT    3300

ATGATCATGA CAGAATGCTG GAACAATAAT GTAAATCAAC GCCCCTCCTT TAGGGATCTA    3360

GCTCTTCGAG TGGATCAAAT AAGGGATAAC ATGGCTGGAG ATTATAAAGA TGATGATGAT    3420

AAAAATTAGC CCGGG                                                     3435
```

(2) INFORMATION FOR SEQ ID NO:22:

(i) SEQUENCE CHARACTERISTICS:
        (A) LENGTH: 1139 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:22:

```
Met Ala Cys Leu Thr Met Thr Glu Met Glu Gly Thr Ser Thr Ser Ser
 1               5                  10                  15

Ile Tyr Gln Asn Gly Asp Ile Ser Gly Asn Ala Asn Ser Met Lys Gln
                20                  25                  30

Ile Asp Pro Val Leu Gln Val Tyr Leu Tyr His Ser Leu Gly Lys Ser
            35                  40                  45

Glu Ala Asp Tyr Leu Thr Phe Pro Ser Gly Glu Tyr Val Ala Glu Glu
        50                  55                  60

Ile Cys Ile Ala Ala Ser Lys Ala Cys Gly Ile Thr Pro Val Tyr His
65                  70                  75                  80

Asn Met Phe Ala Leu Met Ser Glu Thr Glu Arg Ile Trp Tyr Pro Pro
                85                  90                  95

Asn His Val Phe His Ile Asp Glu Ser Thr Arg His Asn Val Leu Tyr
               100                 105                 110

Arg Ile Arg Phe Tyr Phe Pro Arg Trp Tyr Cys Ser Gly Ser Asn Arg
           115                 120                 125

Ala Tyr Arg His Gly Ile Ser Arg Gly Ala Glu Ala Pro Leu Leu Asp
       130                 135                 140

Asp Phe Val Met Ser Tyr Leu Phe Ala Gln Trp Arg His Asp Phe Val
145                 150                 155                 160

His Gly Trp Ile Lys Val Pro Val Thr His Glu Thr Gln Glu Glu Cys
                165                 170                 175

Leu Gly Met Ala Val Leu Asp Met Met Arg Ile Ala Lys Glu Asn Asp
               180                 185                 190

Gln Thr Pro Leu Ala Ile Tyr Asn Ser Ile Ser Tyr Lys Thr Phe Leu
           195                 200                 205

Pro Lys Cys Ile Arg Ala Lys Ile Gln Asp Tyr His Ile Leu Thr Arg
       210                 215                 220

Lys Arg Ile Arg Tyr Arg Phe Arg Arg Phe Ile Gln Gln Phe Ser Gln
225                 230                 235                 240

Cys Lys Ala Thr Ala Arg Asn Leu Lys Leu Lys Tyr Leu Ile Asn Leu
                245                 250                 255

Glu Thr Leu Gln Ser Ala Phe Tyr Thr Glu Lys Phe Glu Val Lys Glu
               260                 265                 270

Pro Gly Ser Gly Pro Ser Gly Glu Glu Ile Phe Ala Thr Ile Ile Ile
           275                 280                 285
```

-continued

```
Thr Gly Asn Gly Gly Ile Gln Trp Ser Arg Gly Lys His Lys Glu Ser
    290                 295                 300
Glu Thr Leu Thr Glu Gln Asp Leu Gln Leu Tyr Cys Asp Phe Pro Asn
305                 310                 315                 320
Ile Ile Asp Val Ser Ile Lys Gln Ala Asn Gln Glu Gly Ser Asn Glu
                325                 330                 335
Ser Arg Val Val Thr Ile His Lys Gln Asp Gly Lys Asn Leu Glu Ile
            340                 345                 350
Glu Leu Ser Ser Leu Arg Glu Ala Leu Ser Phe Val Ser Leu Ile Asp
        355                 360                 365
Gly Tyr Tyr Arg Leu Thr Ala Asp Ala His His Tyr Leu Cys Lys Glu
    370                 375                 380
Val Ala Pro Pro Ala Val Leu Glu Asn Ile Gln Ser Asn Cys His Gly
385                 390                 395                 400
Pro Ile Ser Met Asp Phe Ala Ile Ser Lys Leu Lys Lys Ala Gly Asn
                405                 410                 415
Gln Thr Gly Leu Tyr Val Leu Arg Cys Ser Pro Lys Asp Phe Asn Lys
            420                 425                 430
Tyr Phe Leu Thr Phe Ala Val Glu Arg Glu Asn Val Ile Glu Tyr Lys
        435                 440                 445
His Cys Leu Ile Thr Lys Asn Glu Asn Glu Glu Tyr Asn Leu Ser Gly
    450                 455                 460
Thr Lys Lys Asn Phe Ser Ser Leu Lys Asp Leu Leu Asn Cys Tyr Gln
465                 470                 475                 480
Met Glu Thr Val Arg Ser Asp Asn Ile Ile Phe Gln Phe Thr Lys Cys
                485                 490                 495
Cys Pro Pro Lys Pro Lys Asp Lys Ser Asn Leu Leu Val Phe Arg Thr
            500                 505                 510
Asn Gly Val Ser Asp Val Pro Thr Ser Pro Thr Leu Gln Arg Pro Thr
        515                 520                 525
His Met Asn Gln Met Val Phe His Lys Ile Arg Asn Glu Asp Leu Ile
    530                 535                 540
Phe Asn Glu Ser Leu Gly Gln Gly Thr Phe Thr Lys Ile Phe Lys Gly
545                 550                 555                 560
Val Arg Arg Glu Val Gly Asp Tyr Gly Gln Leu His Glu Thr Glu Val
                565                 570                 575
Leu Leu Lys Val Leu Asp Lys Ala His Arg Asn Tyr Ser Glu Ser Phe
            580                 585                 590
Phe Glu Ala Ala Ser Met Met Ser Lys Leu Ser His Lys His Leu Val
        595                 600                 605
Leu Asn Tyr Gly Val Cys Val Cys Gly Asp Glu Asn Ile Leu Val Gln
    610                 615                 620
Glu Phe Val Lys Phe Gly Ser Leu Asp Thr Tyr Leu Lys Lys Asn Lys
625                 630                 635                 640
Asn Cys Ile Asn Ile Leu Trp Lys Leu Glu Val Ala Lys Gln Leu Ala
                645                 650                 655
Trp Ala Met His Phe Leu Glu Glu Asn Thr Leu Ile His Gly Asn Val
            660                 665                 670
Cys Ala Lys Asn Ile Leu Leu Ile Arg Glu Glu Asp Arg Lys Thr Gly
        675                 680                 685
Asn Pro Pro Phe Ile Lys Leu Ser Asp Pro Gly Ile Ser Ile Thr Val
    690                 695                 700
```

-continued

```
Leu Pro Lys Asp Ile Leu Gln Glu Arg Ile Pro Trp Val Pro Glu
705                 710                 715                 720

Cys Ile Glu Asn Pro Lys Asn Leu Asn Leu Ala Thr Asp Lys Trp Ser
                725                 730                 735

Phe Gly Thr Thr Leu Trp Glu Ile Cys Ser Gly Asp Lys Pro Leu
            740                 745                 750

Ser Ala Leu Asp Ser Gln Arg Lys Leu Gln Phe Tyr Glu Asp Arg His
            755                 760                 765

Gln Leu Pro Ala Pro Lys Trp Ala Glu Leu Ala Asn Leu Ile Asn Asn
        770                 775                 780

Cys Met Asp Tyr Glu Pro Asp Phe Arg Pro Ser Phe Arg Ala Ile Ile
785                 790                 795                 800

Arg Asp Leu Asn Ser Leu Phe Thr Pro Asp Tyr Glu Leu Leu Thr Glu
                805                 810                 815

Asn Asp Met Leu Pro Asn Met Arg Ile Gly Ala Leu Gly Phe Ser Gly
                820                 825                 830

Ala Phe Glu Asp Arg Asp Pro Thr Gln Phe Glu Glu Arg His Leu Lys
        835                 840                 845

Phe Leu Gln Gln Leu Gly Lys Gly Asn Phe Gly Ser Val Glu Met Cys
    850                 855                 860

Arg Tyr Asp Pro Leu Gln Asp Asn Thr Gly Glu Val Val Ala Val Lys
865                 870                 875                 880

Lys Leu Gln His Ser Thr Glu Glu His Leu Arg Asp Phe Glu Arg Glu
                885                 890                 895

Ile Glu Ile Leu Lys Ser Leu Gln His Asp Asn Ile Val Lys Tyr Lys
                900                 905                 910

Gly Val Cys Tyr Ser Ala Gly Arg Arg Asn Leu Lys Leu Ile Met Glu
            915                 920                 925

Tyr Leu Pro Tyr Gly Ser Leu Arg Asp Tyr Leu Gln Lys His Lys Glu
        930                 935                 940

Arg Ile Asp His Ile Lys Leu Leu Gln Tyr Thr Ser Gln Ile Cys Lys
945                 950                 955                 960

Gly Met Glu Tyr Leu Gly Thr Lys Arg Tyr Ile His Arg Asp Leu Ala
                965                 970                 975

Thr Arg Asn Ile Leu Val Glu Asn Glu Asn Arg Val Lys Ile Gly Asp
            980                 985                 990

Phe Gly Leu Thr Lys Val Leu Pro Gln Asp Lys Glu Tyr Tyr Lys Val
        995                 1000                1005

Lys Glu Pro Gly Glu Ser Pro Ile Phe Trp Tyr Ala Pro Glu Ser Leu
    1010                1015                1020

Thr Glu Ser Lys Phe Ser Val Ala Ser Asp Val Trp Ser Phe Gly Val
1025                1030                1035                1040

Val Leu Tyr Glu Leu Phe Thr Tyr Ile Glu Lys Ser Lys Ser Pro Pro
                1045                1050                1055

Ala Glu Phe Met Arg Met Ile Gly Asn Asp Lys Gln Gly Gln Met Ile
                1060                1065                1070

Val Phe His Leu Ile Glu Leu Leu Lys Asn Asn Gly Arg Leu Pro Arg
            1075                1080                1085

Pro Asp Gly Cys Pro Asp Glu Ile Tyr Met Ile Met Thr Glu Cys Trp
        1090                1095                1100

Asn Asn Asn Val Asn Gln Arg Pro Ser Phe Arg Asp Leu Ala Leu Arg
1105                1110                1115                1120

Val Asp Gln Ile Arg Asp Asn Met Ala Gly Asp Tyr Lys Asp Asp Asp
```

Asp Lys Asn (2) INFORMATION FOR SEQ ID NO:23:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GGATCCCCCG GGGGAATGGC CTGCCTTACG ATGAC                            35

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

CATCAAGAAG AGGAGCTTCA GCAC                                        24

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GTTTTCTGGT GCCTTTGAAA GACCG                                    25

(2) INFORMATION FOR SEQ ID NO:26:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

CGCTATGGAT CCCCCGGGCT AATTTTTATC ATCATCATCT TTATAATCTC CAGCCATGTT      60

ATCCCTTATT TG                                                                   72

(2) INFORMATION FOR SEQ ID NO:27:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

-continued

```
GATTACGCCG ACCAGCTGAA TAGCACACTC CCTTGTAC                              38
```

(2) INFORMATION FOR SEQ ID NO:28:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
GCTATGACGT CGCATCCACG CGTACGTAAG C                                     31
```

(2) INFORMATION FOR SEQ ID NO:29:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
GATGATGATA AAAATTAGCC CGGCCGCTGC AGATCTGATC C                          41
```

(2) INFORMATION FOR SEQ ID NO:30:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
GTAAGGCAGG CCATTCCCCC GGCCGCTCCG GAATTCTAG                             39
```

TABLE 1

| Name Used in Report | SEQ ID NO: | Sequence |
|---|---|---|
| | | Box 1 Domain, $\beta_c$: RRKWEEKIPNPSKSHL |
| | | SEQ ID NO:10 |
| peptide 1 | 11 | EKIPNPSKSHLFQNGSAELWP |
| peptide 2 | 12 | RKWEEKIPNPSKSHLFQNGSAELWP |
| peptide 3 | 13 | YRLRRKWEEKIPNPSKSHLFQNGSAELWP |
| peptide 4 | 14 | GIYGYRLRRKWEEKIPNPSKSHLFQNGSAELWP |
| peptide 5 | 15 | FCGIYGYRLRRKWEEKIPNPSKSHLFQNGSAELWP |
| peptide 6 | 16 | LALRFCGIYGYRLRRKWEEKIPNPSKSHLFQNGSAELWP |
| CTD-3 | 17 | GIYGYRLRRKWEEKIPNPSKS |
| CTD-4 | 18 | GIYGYRLRRKWEEKIPN |
| CTD-5 | 19 | GIYGYRLRRKWEE |

TABLE 2

| Hours | % JAK2 Remaining |
|---|---|
| 0 | 100 |
| 1 | 46.0 |
| 2 | 39.6 |
| 3 | 32.5 |
| 4 | 43.7 |
| 5 | 44.1 |
| 6 | 41.3 |

What is claimed is:

1. A method of screening for compounds useful for inhibiting JAK2/Cytokine receptor binding, said method comprising:

(a) contacting a first molecule comprising at least the N-terminal 294 residues of JAK2 protein as shown in (SEQ ID NO:5) with a second molecule comprising at least 13 membrane-proximal cytoplasmic amino acids of $\beta_c$ subunit of the IL-3, IL-5 and GM-CSF receptors as shown in (SEQ ID NO:2) in the presence of a candidate compound; and (b) detecting whether a complex forms between said first and second molecules to determine whether said candidate compound inhibits the formation of said complex.

2. The method of claim 1, further comprising prior to said contacting step, the step of labeling said second molecule with a fluorescent molecule.

3. The method of claim 2, wherein said detection step comprises measuring changes in fluorescence polarization.

4. The method of claim 1, further comprising prior to said contacting step, the steps of labeling said first molecule with a radioisotope and said second molecule with an affinity tag.

5. The method of claim 4, wherein said detection step comprises:

incubating said labeled first molecule with said second molecule on a scintillant-containing substrate; and measuring changes in scintillation.

6. The method of claim 1, further comprising prior to said contacting step, the steps of labeling said first molecule with an affinity tag and said second molecule with a radioisotope.

7. The method of claim 6, wherein said detection step comprises:

incubating said labeled first molecule with said second molecule on a scintillant-containing substrate; and measuring changes in scintillation.

8. The method of claim 1, further comprising prior to said contact step, the step of immobilizing said first molecule to a solid support.

9. The method of claim 8, wherein said detection step comprises:

incubating said second molecule with said immobilized first molecule;

determining whether said second molecule is bound to said immobilized first molecule by enzyme-linked immunoabsorbant assay.

10. The method of claim 1, further comprising prior to said contact step, the step of immobilizing said second molecule to a solid support.

11. The method of claim 10, wherein said detection step comprises:

incubating said first molecule with said immobilized second molecule;

determining whether said first molecule is bound to said immobilized second molecule by enzyme-linked immunoabsorbant assay.

12. A method for screening compounds useful for inhibiting JAK2/Cytokine receptor binding, said method comprising:

(a) contacting a first molecule comprising at least the N terminal 294 residues of JAK2 protein as shown in (SEQ ID NO: 5) with a second molecule comprising a polypeptide selected from the group consisting of polypeptides represented by SEQ ID NO: 13, SEQ ID NO: 14, SEQ ID NO: 15, SEQ ID NO: 17, SEQ ID NO: 18 and SEQ ID NO: 19 in the presence of a candidate compound; and (b) detecting whether a complex forms between said first and second molecules to determine whether said candidate compound inhibits the formation of said complex.

13. The method of claim 12, further comprising prior to said contacting step, the step of labeling said second molecule with a fluorescent molecule.

14. The method of claim 13, wherein said detection step comprises measuring changes in fluorescence polarization.

15. The method of claim 12, further comprising prior to said contacting step, the steps of labeling said first molecule with a radioisotope and said second molecule with an affinity tag.

16. The method of claim 15, wherein said detection step comprises:

Incubating said labeled first molecule with said second molecule on a scintillant-containing substrate; and measuring changes in scintillation.

17. The method of claim 12, further comprising prior to said contacting step, the steps of labelling said first molecule with an affinity tag and said second molecule with a radioisotope.

18. The method of claim 17, wherein said detection step comprises:

Incubating said labeled first molecule with said second molecule on a scintillant-containing substrate; and:

measuring changes in scintillation.

19. The method of claim 12, further comprising prior to said contacting step, the step of immobilizing said first molecule to a solid support.

20. The method of claim 19, wherein said detection step comprises;

incubating said second molecule with said immobilized first molecule; and determining whether said second molecule is bound to said immobilized first molecule by enzyme-linked immunosorbent assay.

21. The method of claim 12, further comprising prior to said contact step, the step of immobilizing said second molecule to a solid support.

22. The method of claim 21, wherein said detection step comprises:

incubating said first molecule with said immobilized second molecule;

determining whether said first molecule is bound to said immobilized second molecule by enzyme linked immunoabsorbant assay.

* * * * *